US009764007B2

(12) United States Patent
Fang et al.

(10) Patent No.: US 9,764,007 B2
(45) Date of Patent: *Sep. 19, 2017

(54) CLASS OF THERAPEUTIC PROTEIN BASED MOLECULES

(71) Applicant: Ansun Biopharma, Inc., San Diego, CA (US)

(72) Inventors: Fang Fang, San Diego, CA (US); Michael P. Malakhov, San Diego, CA (US)

(73) Assignee: Ansun Biopharma, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/954,467

(22) Filed: Nov. 30, 2015

(65) Prior Publication Data

US 2016/0184407 A1     Jun. 30, 2016

Related U.S. Application Data

(63) Continuation of application No. 14/274,912, filed on May 12, 2014, now Pat. No. 9,212,353, which is a continuation of application No. 13/970,229, filed on Aug. 19, 2013, now Pat. No. 8,722,869, which is a continuation of application No. 12/861,392, filed on Aug. 23, 2010, now Pat. No. 8,512,710, which is a continuation of application No. 10/939,262, filed on Sep. 10, 2004, now Pat. No. 7,807,174.

(60) Provisional application No. 60/561,749, filed on Apr. 13, 2004, provisional application No. 60/580,084, filed on Jun. 16, 2004.

(51) Int. Cl.

| C12N 9/36 | (2006.01) |
|---|---|
| A61K 38/47 | (2006.01) |
| C12N 9/24 | (2006.01) |
| C07K 14/47 | (2006.01) |
| C07K 14/52 | (2006.01) |
| C07K 14/54 | (2006.01) |
| C07K 14/775 | (2006.01) |
| C07K 14/81 | (2006.01) |
| A61K 48/00 | (2006.01) |
| C12N 7/00 | (2006.01) |
| C12N 15/86 | (2006.01) |
| A61K 47/48 | (2006.01) |
| C07K 14/475 | (2006.01) |
| A61K 39/00 | (2006.01) |
| A61K 38/00 | (2006.01) |

(52) U.S. Cl.
CPC ........ *A61K 38/47* (2013.01); *A61K 47/48246* (2013.01); *A61K 48/0008* (2013.01); *C07K 14/47* (2013.01); *C07K 14/4703* (2013.01); *C07K 14/475* (2013.01); *C07K 14/4711* (2013.01); *C07K 14/521* (2013.01); *C07K 14/522* (2013.01); *C07K 14/5421* (2013.01); *C07K 14/775* (2013.01); *C07K 14/8117* (2013.01); *C07K 14/8128* (2013.01); *C12N 7/00* (2013.01); *C12N 9/2402* (2013.01); *C12N 9/2405* (2013.01); *C12N 15/86* (2013.01); *C12Y 302/01018* (2013.01); *A61K 38/00* (2013.01); *A61K 39/00* (2013.01); *C07K 2319/00* (2013.01); *C07K 2319/01* (2013.01); *C07K 2319/33* (2013.01); *C12N 2750/14143* (2013.01); *C12N 2750/14145* (2013.01); *C12N 2760/16111* (2013.01)

(58) Field of Classification Search
CPC ...................... C12Y 302/01018; C12N 9/2402
USPC ........................................................ 435/206
See application file for complete search history.

(56) References Cited

U.S. PATENT DOCUMENTS

| 3,439,089 A | 4/1969 | Cherkas et al. |
|---|---|---|
| 5,532,215 A | 7/1996 | Lezdey et al. |
| 5,643,758 A | 7/1997 | Guan et al. |
| 5,985,859 A | 11/1999 | Luo |
| 6,251,392 B1 | 6/2001 | Hein et al. |

(Continued)

FOREIGN PATENT DOCUMENTS

| WO | WO93/03708 | 3/1993 |
|---|---|---|
| WO | WO98/31817 | 7/1998 |

(Continued)

OTHER PUBLICATIONS

Achyuthan and Achyuthan "Comparative enzymology, biochemistry and pathophysiology of human exo-a-sialidases (neuraminidases)," *Comparative Biochemistry & Physiology part B* 129:29-64 (2001).

(Continued)

*Primary Examiner* — Tekchand Saidha
(74) *Attorney, Agent, or Firm* — Fish & Richardson P.C.

(57) ABSTRACT

The present invention provides new compositions and methods for preventing and treating pathogen infection. In particular, the present invention provides compounds having an anchoring domain that anchors the compound to the surface of a target cell, and a therapeutic domain that can act extracellularly to prevent infection of a target cell by a pathogen, such as a virus. The present invention also comprises therapeutic compositions having sialidase activity, including protein-based compounds having sialidase catalytic domains. Compounds of the invention can be used for treating or preventing pathogen infection, and for treating and reducing allergic and inflammatory responses. The invention also provides compositions and methods for enhancing transduction of target cells by recombinant viruses. Such compositions and methods can be used in gene therapy.

16 Claims, 13 Drawing Sheets

(56) References Cited

U.S. PATENT DOCUMENTS

Figure 1:
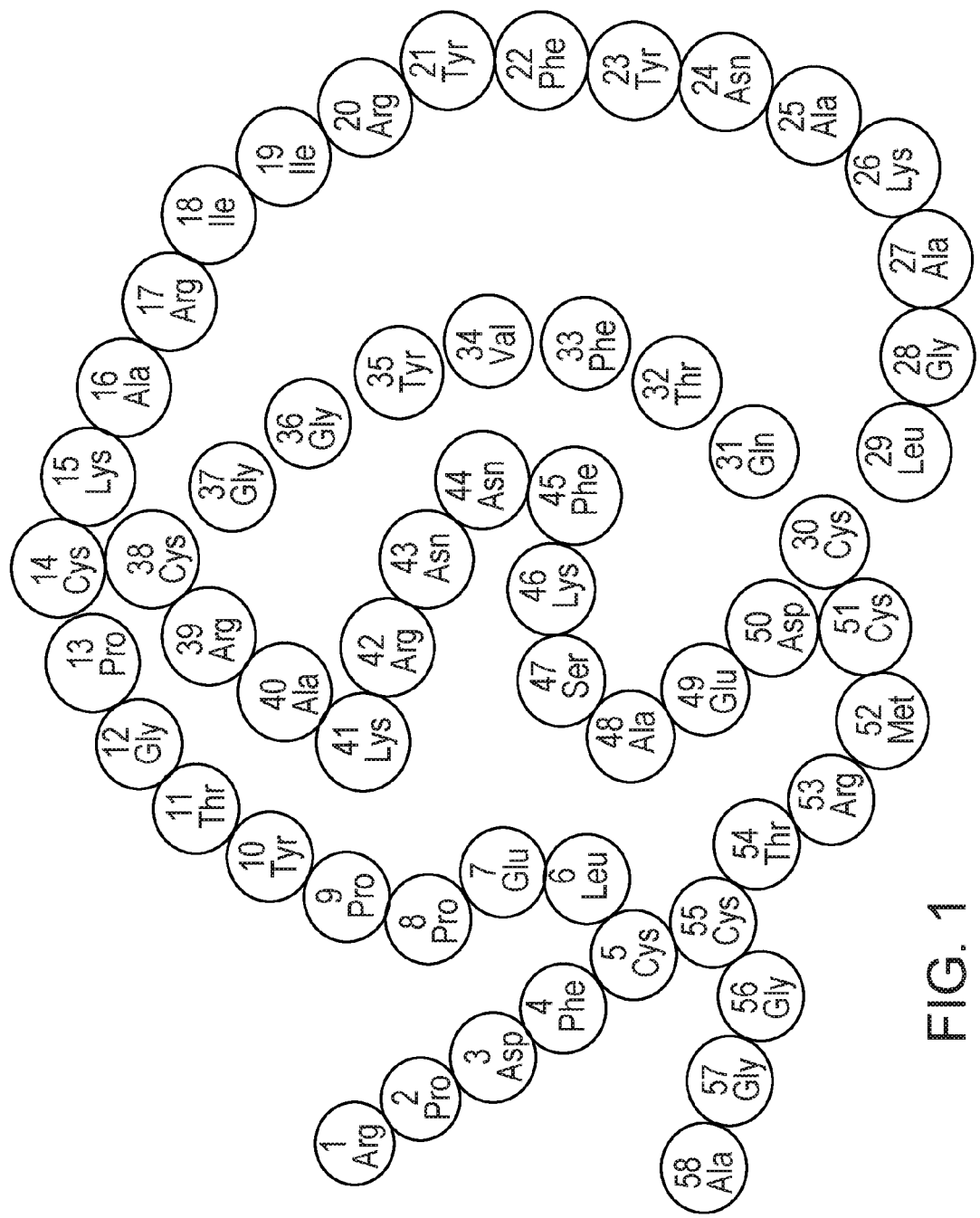
Figure 8:
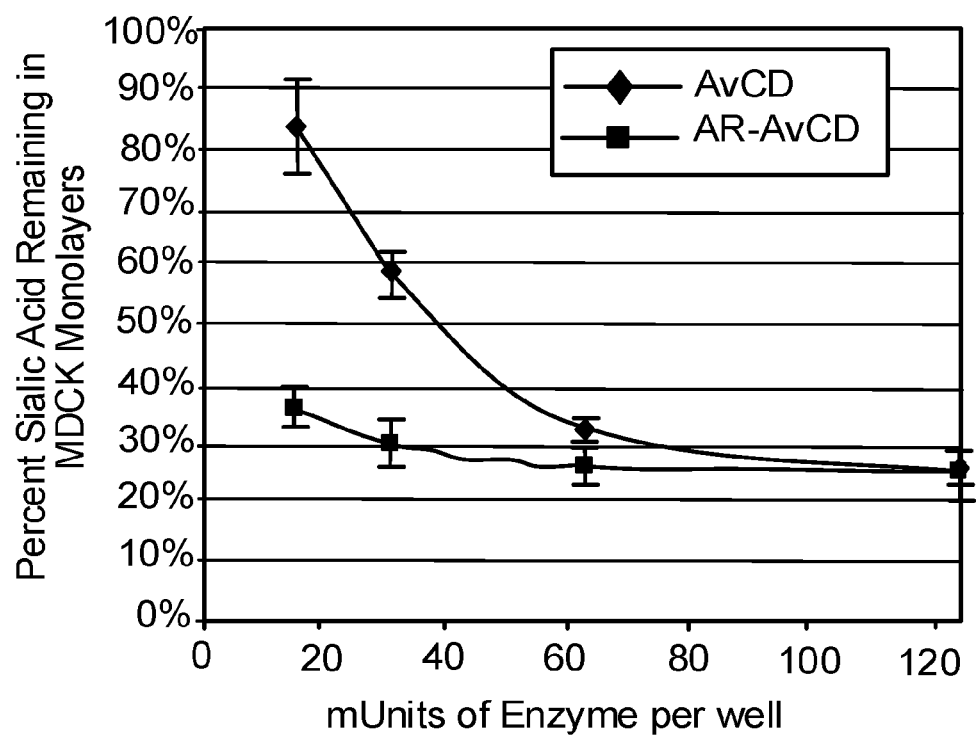

| | | | |
|---|---|---|---|
| 6,440,419 | B1 | 8/2002 | Hein et al. |
| 6,737,511 | B1 | 5/2004 | Youle et al. |
| 6,855,801 | B1 | 2/2005 | San Antonio et al. |
| 7,807,174 | B2* | 10/2010 | Fang .............. C12Y 302/01018 424/192.1 |
| 8,084,036 | B2* | 12/2011 | Yu .......................... A61K 38/47 424/192.1 |
| 8,512,710 | B2* | 8/2013 | Fang .............. C12Y 302/01018 424/192.1 |
| 2002/0025320 | A1 | 2/2002 | Boyaka et al. |
| 2005/0004020 | A1 | 1/2005 | Yu et al. |
| 2005/0112751 | A1 | 5/2005 | Fang et al. |
| 2007/0190163 | A1 | 8/2007 | Malaknov et al. |
| 2008/0075708 | A1 | 3/2008 | Yu et al. |

FOREIGN PATENT DOCUMENTS

| | | |
|---|---|---|
| WO | WO2004/047735 | 6/2004 |
| WO | WO2006/031291 | 3/2006 |

OTHER PUBLICATIONS

Ada et al., Purification and properties of neuraminidase from *Vibrio cholera*, J Gen Microbiol 24:409 (1961).

Ah-Tse et al., "Virus-Receptor Interactions of Human Parainfluenza Viruses Types 1,2 and 3," *Microbial Pathogenesis*, 27: 329-336 (1999).

Ahmed et al., "Attachment of moraxella catarrhalis to pharyngeal epithelial cells is mediated by a glycosphingolipid receptor," *FEMS Microbiology Letters*, 135:305-309 (1996).

Air and Laver, "Red cells bound to influenza virus N9 neuraminidase are not released by the N9 neuraminidase activity," *Virology*, 211:278-284 (1995).

Alvarez et al., "Improving protein pharmacokinetics by genetic fusion to simple amino acid sequences," *Journal of Biological Chemistry*, 279:3375-3381 (2004).

Andersson et al., "Inhibition of attachment of *Streptococcus pneumoniae* and *Haemophilus influenzae* by human milk and receptor oligosaccharides," *Journal of Infectious Diseases*, 153:232-237 (1986).

Anderson et al., "Mucins and Mucoids in Relation to Influenza Virus Action. VI. General Discussion," *Walter and Eliza Hall Institute of Medical Research, Melbourne*, 403-411 (1948).

Anderson, "Mucins and Mucoids in Relation to Influenza Virus Action, 1. Inactivation by RDE and by Viruses of the Influenza Group, of the Serum Inhibitor of Haemagglutination," *Walter and Eliza Hall Institute of Medical Research, Melbourne*, 347-354 (1948).

Andrews et al., "Community-acquired pneumonia," *Current Opinion in Pulmonary Medicine*, 9:175-180 (2003).

Angata et al., "1-type lectins," *Biochimica et Biophysica Acta*, 1572:294-316 (2002).

Auerswald et al., "Expression, isolation and characterization of recombinant [Arg15,Glu52] Aprotinin," *Biological Chemistry Hoppe-Seyler*, 369:Supp1:27-35 (1988).

Baker et al., "Glycosphingolipid receptors for pseudomonas aeruginosa," *Infection and Immunity*, 58:2361-2366 (1990).

Ball, "Epidemiology and treatment of chronic bronchitis and its exacerbations," *Chest*, 108:43S-52S (1995).

Bals et al., "Transduction of well-differentiated airway epithelium by recombinant adeno-associated virus is limited by vector entry," *Journal of Virology*, 73:6085-6088 (1999).

Barbey-Morel et al., "Role of respiratory tract proteases in infectivity of influenza A virus," *Journal of Infectious Diseases*, 155:667-672 (1987).

Barthelson et al., "Adherence of *Streptococcus pneumoniae* to respiratory epithelial cells is inhibited by sialylated oligosaccharides," *Infection and Immunity*, 66:1439-1444 (1998).

Bartlett et al. "Community-acquired pneumonia in adults: Guidelines for management," *The Infectious Diseases Society of America Clinical Infectious Diseases*, 26:811-838 (1998).

Belser et al., "DAS181, A novel sialidase fusion protein, protects mice from lethal avian influenza H5N1 virus infection" *Journal of Infectious Disease*, 196:1493-1499 (2007).

Belshe, R. et al., "Genetic basis of resistance to rimantadine emerging during treatment of influenza virus infection," *Journal of Virology*, 62:1508-1512 (1988).

Benet et al., *Pharmacological Basis of Therapeutics*, 8th ed., Eds. Goodman and Gillman, p. 1-32, (1990).

Bergelson et al., "Role of gangliosides in reception of influenza virus," *European Journal of Biochemistry*, 128(2-3):467-474 (1982).

Bessette "Efficient folding of proteins with multiple disulfide bonds in the *Escherichia coli* cytoplasm." *Proceedings of the National Academy of Sciences of the United States of America*, 96(24):13703-13708 (1999).

Beswick et al., "Comparative studies of glycosaminoglycan involvement in Chlamydia pneumoniae and C trachomatis invasion of host cells," *Journal of Infectious Diseases*, 187:1291-1300 (2003).

Byron et al., "Drug Delivery Via the Respiratory Tract," *Journal of Aerosol Medicine*, 7(1):49-75 (1994).

Callan, "Cleavage of influenza A virus H1 hemagglutinin by swine respiratory bacterial proteases," *Journal of Virology*, 71(10):7579-7585 (1997).

Cardin et al., "Molecular modeling of protein-glycosaminoglycan interactions," *Arteriosclerosis* 9:21-32 (1989).

Cechecchi et al., "Heparan sulfate glycosaminoglycans are receptors sufficient to mediate the initial binding of adenovirus types 2 and 5," *J. Virol.*, 75:8772-80 (2001).

Cocchiara et al., "Inhibitory effect of neuraminidase on SP-induced histamine release and TNF-alpha mRNA in rat mast cells: Evidence of a receptor-independent mechanism," *Journal of Neuroimmunology*, 75:9-18 (1997).

Comelli et al., "Identification and expression of Neu4, a novel murine sialidase," *Gene*, 321:155-161 (2003).

Connor et al., "Receptor specificity in human, avian, and equine H2 and H3 influenza virus isolates," *Virology*, 205:17-23 (1994).

Copley, R., "Sialidase-like Asp-boxes:sequence-similar structures within different protein folds," *Protein Sciences*, 10(2):285-292 (2001).

Corfield et al., "The release of N-acetyl- and N-glycolloyl-neuraminic acid from soluble complex carbohydrates and erythrocytes by bacterial, viral and mammalian sialidases," *Biochemical Journal*, 197(2):293-299 (1981).

Cowley and Gorman, "Effects of proteolytic enzymes on the infectivity, haemagglutinating activity and protein composition of bluetongue virus type 20," *Veterinary Microbiology*, 22(2-3):137-152 (1990).

Crennell et al., "Crystal structure of a bacterial sialidase (from *Salmonella typhimurium* LT2) shows the same fold as an influenza virus neuraminidase." *Proceedings of the National Academy of Sciences of the United States of America*, 90:9852-9856 (1993).

Crennell et al., "Crystal structure of vibrio *Cholerae neuraminidase* reveals dual lectin-like domains in addition to the catalytic domain," *Structure* 2:535-544 (1994).

Crocker and Varki, "Siglecs, sialic acids and innate immunity," *Trends in Immunology*, 22:337-342 (2001).

Cundell et al., "Relationship between colonial morphology and adherence of *Streptococcus pneumoniae,*" *Infection and Immunity*, 63:757-761 (1995).

Cundell, D. and E. Tuomanen, "Receptor specificity of adherence of *Streptococcus pneumoniae* to human type-II pneumocytes and vascular endothelial cells in vitro," *Microbial Pathogenesis*, 17:361-374 (1994).

Drzeniek, "Substrate specificity of neuraminidases," *Histochemical Journal*, 5(3):271-290 (1973).

Els et al., "Sialic acid is cleaved from glycoconjugates at the cell surface when influenza virus neuraminidases are expressed from recombinant vaccinia viruses," *Virology* 170(1):346-351 (1989).

(56) References Cited

OTHER PUBLICATIONS

Endo et al., "Growth of influenza A virus in primary, differentiated epithelial cells derived from adenoids," *Journal of Virology*, 70(3):2055-2058 (1996).
Ernst et al., "Enzymatic degradation of glycosaminoglycans," *Critical Re.v Biochem. Mol. Biol.*, 30:387-444 (1995).
Faden, "The microbiologic and immunologic basis for recurrent otitis media in children," *European Journal of Pediatrics*, 160:407-413 (2001).
Fakih et al., "Specific binding of haemophilus influenzae to minor gangliosides of human respiratory epithelial cells," *Infection and Immunity*, 65:1695-1700 (1997).
Fiers et al., "Soluble recombinant influenza vaccines", Phil. Trans R. Soc. London, 356:1961-1963 (2001).
File, T., "The epidemiology of respiratory tract infections," Seminars in Respiratory Infections, 15:184-194 (2000).
Finlay and Falkow, "Common Themes in Microbial Pathogenicity," *Microbiological Reviews*, 210-230 (1989).
Flotte et al., "Stable in vivo expression of the cystic fibrosis transmembrane conductance regulator with an adeno-associated virus vector," *Proceedings of the National Academy of Sciences of the United States of America*, 90:10613-10617 (1993).
Flotte, T. and B. Carter, "Adeno-associated virus vectors for gene therapy of cystic fibrosis," *Methods in Enzymology*, 292:717-732 (1998).
Fritz et al., "Biochemistry and applications of aprotinin, the kallikrein inhibitor from bovine organs" *Arzneimittel-Forschung*, 33(4):479-494 (1983).
Fukudome et al., "Comparison of human, simian, and bovine rotaviruses for requirement of sialic acid in hemagglutination and cell adsorption," *Virology*, 172(1):196-205 (1989).
Garcia-Rodriguez et al., "Dynamics of nasopharyngeal colonization by potential respiratory pathogens," *Journal of Antimicrobial Chemotherapy*, 50(S2):59-73 (2002).
Garten et al., "Proteolytic activation of the influenza virus hemagglutinin: the structure of the cleavage site and the enzymes involved in cleavage," *Virology*, 115(2):361-374 (1981).
Gaskell et al., "The three domains of a bacterial sialidase: A beta-propeller, an immunoglobulin module and a galactose-binding jelly-roll," *Structure*, 3:1197-1205 (1995).
Genbank Accession Protein No. A49227 (2 pgs.) (accessed on Sep. 19, 2007).
GenBank Accession Protein No. AAH09799 (3 pgs.) (accessed on Sep. 19, 2007).
Genbank CoreNucleotide Accession No. D01045 (4 pgs.) (accessed on Feb. 1, 2007).
Genbank CoreNucleotide Accession No. L06898 (4 pgs.) (accessed on Sep. 19, 2007).
Genbank CoreNucleotide Accession No. NM080741 (4 pgs.) (accessed on Apr. 20, 2007).
Genbank CoreNucleotide Accession No. X62276 (4 pgs.) (accessed on Feb. 1, 2007).
Genbank CoreNucleotide Accession No. X87369 (6 pgs.) (accessed on Feb. 1, 2007).
Genbank CoreNucleotide Accession No. Y16535 (4 pgs.) (accessed on Feb. 1, 2007).
GenBank Accession Protein No. AAA21932.1.
Goger et al., "Different affinities ofglycosaminoglycan oligosaccharides for monomeric and dimericinterleukin-8: a model for chemokine regulation atinflammatory sites," *Biochemistry*, 41:1640-1646 (2002).
Gotoh et al., "An endoprotease homologous to the blood clotting factor X as a determinant of viral tropism in chick embryo," *EMBO Journal*, 9:4189-4195 (1990).
Gottschalk, A., Chemistry of virus receptors, p. 51-61. In F. Burnet and W. Stanley (eds.), *The Viruses; biochemical, biological and biophysical properties*, Academic Press, Inc., New York, NY, (1959).

Granoff & Webster, R. G., ed. "Influenza Viruses (Orthomyxoviridae)," *Encyclopedia of Virology: 2nd Edition*, vol. 2:824-841 (1999).
Griffin et al., Effects of hexose starvation and the role of sialic acid in influenza virus release, *Virology*, 125(2):324-334 (1983).
Guibinga et al., "Cell surface heparin sulfate is a receptor for attachment of envelope protein-free retrovirus-like particles and VSV-G pseudotyped MLV-derived retrovirus vectors to target cells." *Molecular Therapeutics*, 5:538-46 (2002).
Gust et al., "Planning for the next pandemic," *Reviews in Medical Virology*, 11:59-70 (2001).
Halbert et al., "Efficient mouse airway transduction following recombination between AAV vectors carrying parts of a larger gene," *Nature Biotechnology*, 20:697-701 (2002).
Halbert et al., "Successful readministration of adeno-associated virus vectors to the mouse lung requires transient immunosuppression during the initial exposure," *Journal of Virology*, 72:9795-9805 (1998).
Hayden, F., "Amantadine and rimantadine-mechanisms," *Antiviral Drug Resistance* (ed., D. Richman), 59-77, Chichester, UK: John Wiley & Sons Ltd. (1996).
Hazlett et al., "In vivo identification of sialic acid as the ocular receptor for Pseudomonas aeruginosa," *Infection and Immunity*, 51:687-689 (1986).
Hirel et al., Extent of N-terminal methionine excision from *Escherichia coli* proteins is governed by the side-chain length of the penultimate amino acid, Proceedings of the National Academy of Sciences of the United States of America, 86:8247-8251 (1989).
Hirmo et al., "Adhesion of Helicobacter pylori strains to alpha-2,3-linked sialic acids," *Glycoconjugate Journal*, 13:1005-1011 (1996).
Hosoya et al., "Effects of protease inhibitors on replication ofvarious myxoviruses," *Antimicrobial Agents and Chemotherapy*, 36:1432-1436 (1992).
Ishibashi et al., "Probiotics and safety," *The American Journal of Clinical Nutrition*, 73: 465S-470S (2001).
Ito, "Interspecies transmission and receptor recognition of influenza a virus," *Microbiology and Immunology*, 44(6):423-430 (2000).
Janakiraman et al., "Structure of influenza virus neuraminidase B/lee/40 complexed with sialic acid and a dehydro analog at 1.8-A resolution: implications for the catalytic mechanism," *Biochemistry* 33:8172-8179 (1994).
Jarreau et al., "Effects of neuraminidase on airway reactivity in the guinea pig," *American Review of Respiratory Disease*, 145:906-910 (1992).
Johnson et al., "Heparan Sulfate is Essential to Amphiregulin-induced Mitogenic Signaling by the Epidermal Growth Factor Receptor", *Journal of Biological Chemistry*, 269(43):27149-27154 (1994).
Jones et al., Journal of Neuropathology and Experimental Neurology, 57(2): 140-157 (1998).
Jones et al., "Caprine Mucopolysaccharidosis-IIID: Clinical, Biochemical, Morphological and Immunohistochemical Characteristics", *Journal of Neuropathology and Experimental Neurology*, 57(2): 148-157 (1998).
Kai et al., "The influence of neuraminidase treatment on tracheal smooth muscle contraction," *European Journal of Pharmacology*, 220:181-185 (1992).
Karlsson, "Meaning and therapeutic potential of microbial recognition of host glycoconjugates," *Molecular Microbiology*, 29:1-11 (1998).
Karp et al., "An in vitro model of differentiated human airway epithelia methods for establishing primary cultures," *Methods in Molecular Biology*, 188:115-137 (2002).
Kawakami, K., "Attachment of nontypable Haemophilus influenzae to human pharyngeal epithelial cells mediated by a ganglioside receptor," *Microbiology and Immunology*, 42:697-702 (1998).
Kido et al., "Cellular proteases involved in the pathogenicity of enveloped animal viruses, human immunodeficiency virus, influenza virus A and sendai virus," *Advances in Enzyme Regulation*, 36:325-347 (1996).
Kido et al., Cellular proteinases and viral infection: influenza virus, sendai virus and HIV-1, pp. 205-217 In B Dunn (ed.), *Proteases of Infectious Agents*, Academic Press, New York, NY, (1999).

(56) References Cited

OTHER PUBLICATIONS

Klenk et al., "Host cell proteases controlling virus pathogenicity," *Trends in Microbiology*, 2:39-43 (1994).

Klenk et al., "The molecular biology of influenza virus pathogenicity," *Advances in Virus Research*, 34:247-281 (1988).

Kreisel et al., "Different half-lives of the carbohydrate and protein moieties of a 110,000-dalton glycoproteins isolated from plasma membranes of rat liver," *Proceedings of the National Academy of Sciences of the United States of America*, 77:1828-1831 (1980).

Krunkosky et al., "Effects of TNF-b on expression of ICAM-1 in human airway epithelial cells in vitro," *American Journal of Respiratory Cell and Molecular Biology*, 22:685-692 (2000).

Kruse et al., "Expression and Purification of a Recombinant 'Small' Sialidase from Clostridium perfingens A99", *Protein Expr Purif.*, 7(4):415-22 (1996).

Lanzrein, M. et al., "Entry and uncoating of enveloped viruses," *Biochem. J.*, 302:313-320 (1994).

Lazarowitz et al., "Proteolytic cleavage by plasmin of the HA polypeptide of influenza virus: host cell activation of serum plasminogen," *Virology*, 56:172-180 (1973).

Le Calvez et al., "Biochemical prevention and treatment of viral infections-a new paradigm in medicine for infectious diseases," *Virology Journal*, 1:12 (2004).

Lee, M. and A. Lander, "Analysis of affinity and structural selectivity in the binding of proteins to glycosaminoglycans: development of a sensitive electrophoretic approach," *Proceedings of the National Academy of Sciences of the United States of America*, 88:2768-2772 (1991).

Loomes et al., "Erythrocyte receptors for Mycoplasma pneumoniae are sialylated oligosaccharides of Ii antigen type," *Nature*, 307:560-563 (1994).

Loveless et al., "Sialo-Oligosaccharide Receptors for Mycoplasma pneumoniae and Related Oligosaccharides of Poly-N-Acetyllactosamine Series Are Polarized at the Cilia and Apical-Microvillar Domains of the Ciliated Cells in Human Bronchial Epithelium" *Infection and Immunity*, 57(4):1285-1289 (1989).

Lyczak, J., "Lung infections associated with cystic fibrosis," *Clinical Microbiology Reviews*, 15:194-222 (2002).

MacEachran et al., "Adhesion of Pseudomonas aeruginosa to human buccal spithelial cells: evidence for two classes of receptors," *Canadian J. Microbiol.*, 31:563-569 (1985).

Macfarlane, J., "An overview of community acquired pneumonia with lessons learned from the British Thoracic Society Study," *Seminars in Respiratory Infections*, 9:153-165 (1994).

Malakhov et al., "Sialidase fusion protein as a novel broad-spectrum inhibitor of influenza virus infection," *Antimicrobial Agents and Chemotherapy*, 50(4):1470-1479 (2006).

Marcus et al. "Adherence of Pseudomonas aeruginosa to Tracheal Epithelium", *Infection and Immunity*, 57:1050-1053 (1989).

Martinez, I. and J. Melero, "Binding of human respiratory syncytial virus to cells: implication of sulfated cell surface proteoglycans," *Journal of General Virology*, 81:2715-2722 (2000).

Matrisovich et al., "Natural and synthetic sialic acid-containing inhibitors of influenza virus receptor binding," *Rev. Med. Virol.*, 13(2):85-97 (2003).

Matrosovich et al., "Natural and synthetic sialic acid-containing inhibitors of influenza virus receptor binding," *Rev. Med. Virol.*, 13(2):85-97 (2003).

Matsushima et al., "Etiology and management of community-acquired pneumonia in Asia," *Current Opinion in Infectious Diseases*, 15:157-162 (2002).

Mbaki, et al., "Correlation between Branhamella catarrhalis adherence to oropharyngeal cells and seasonal incidence of lower respiratory tract infections," *Tohoku Journal of Experimental Medicine*, 153:111-121 (1987).

Meltzer et al., "The economic impact of pandemic influenza in the United States: priorities for intervention," *Emerging Infectious Diseases*, 5:659-671 (1999).

Mendel et al., "Oral administration of a prodrug of the influenza virus neuraminidase inhibitor GS 4071 protects mice and ferrets against influenza infection," *Antimicrobial Agents and Chemotherapy*, 42:640-646 (1998).

Meuller T.D., et al., Structure, binding and antagonists in the IL-4/IL-13 receptor system. *Biochimica et Biophysica Acta*, 1592:237-250 (2002).

Meyer et al., "On the role of sialic acid in the rheological properties of mucus," *Biochimica et Biophysica Acta*, 392:223-232 (1975).

Miller-Podraza et al., "Recognition of glycoconjugates by Helicobacter pylori Comparison of two sialic acid-dependent specificities based on haemagglutination and binding to human erythrocyte glycoconjugates," *Glycoconjugate Journal*, 4:467-471 (1997).

Milner et al., "Identification of a sialidase encoded in the human major histocompatibility complex," *Journal of Biochemistry*, 272:4549-4558 (1997).

Monti et al., "Expression of a novel human sialidase encoded by the NEU2 gene," *Glycobiology*, 9:1313-1321 (1999).

Monti et al., "Identification and expression of NEU3, a novel human sialidase associated to the plasma membrane," *Biochemical Journal*, 349:343-351 (2000).

Monti et al., "Molecular cloning and characterization of NEU4, the fourth member of the human sialidase gene family," *Genomics*, 83(3):445-453 (2004).

Monti et al., "Recent development in mammalian sialidase molecular biology," *Neurochemical Research*, 27:646-663 (2002).

Moscona et al., "Analysis of Human Parainfluenza Virus 3 Receptor Binding Variants: Evidence for the Use of a Specific Sialic Acid-Containing Receptor", *Microbial Pathogenesis*, 20:179-184 (1996).

Moscona, "Entry of Parainfluenza Virus into Cells as a Target for Interrupting Childhood Respiratory Disease," *The Journal of Clinical Investigation*, 115(7):1688-1698 (2005).

Moscona et al., "Fusion Properties of Cells Persistently Infected with Human Parainfluenza Virus Type 3: Participation of Hemagglutinin-Neuraminidase in Membrane Fusion," *Journal of Virology*, 65(6):2773-2777 (1991).

Moscona et al., "Fusion Properties of Cells Infected with Human Parainluenza Virus Type 3: Receptor Requirements for Viral Spread and Virus-Mediated Membrane Fusion", *Journal of Virology*, 66(11):6280-6287 (1992).

Meuller et al., "Structure, binding and antagonists in the IL-4/IL-13 receptor system," *Biochim.. Biophys. Acta.*, 1592:237-250 (2002).

Murakami et al., "Mini-plasmin found in the epithelial cells of bronchioles triggers infection by broad-spectrum influenza A viruses and Sendai virus," *European Journal of Biochemistry*, 268:2847-2855 (2001).

Nakayama, K., "Furin:a mammalian subtilisin/kex2p- like endoprotease involved in process of a wide variety of precursor proteins," *Biochemical Journal*, 327:625-635 (1997).

NCBI Protein AAH09799 (3 pgs.) (accessed on Sep. 19, 2007).

Neumann, G., et al., "Generation of Influenza A viruses entirely from cloned cDNAs," *Proceedings of the National Academy of Sciences of the United States of America*, 96:9345-9350 (1999).

Ovcharenko, A. and O. Zhirnov, "Aprotinin aerosol treatment of influenza and paramyxovirus bronchopneumonia of mice," *Antiviral Research*, 23:107-118 (1994).

Palermo et al., "Human Parainfluenza Virus Infection of the Airway Epithelium: Viral Hemagglutinin-Neuraminidase Regulates Fusion Protein Activation and Modulates Infectivity," *Journal of Virology*, 83(13):6900-6908 (2009).

Park et al., "Exploitation of syndecan-1 shedding by Pseudomonas aeruginosa enhances virulence," *Nature*, 411:98-102 (2001).

Plowman, G. D., "The Amphiregulin Gene Encodes a Novel Epidermal Growth Factor-Related Protein with Tumor-Inhibitory Activity," *Molecular and Cellular Biology*, 10(5):1969-1981 (1990).

Potier, M., "Fluorometric assay of neuraminidase with a sodium (4-methylumbelliferyl-alpha-D-N-acetylneuraminate) substrate," *Analytical Biochemistry*, 94:287-296 (1979).

Powell et al,, Attachment of Mycoplasma pneumoniae to Respiratory Epithelium:, *Infection and Immunity*, 13(3):959-966 (1976).

(56) References Cited

OTHER PUBLICATIONS

Pshezhetsky et al., "Cloning, expression and chromosomal mapping of human lysosomal sialidase and characterization of mutations in sialidosis," *Nature Genetics*, 15:316-320 (1997).
Ramphal, R. and M. Pyle "Evidence for mucins and sialic acid as receptors for Pseudomonas aeruginosa in the lower respiratory tract," *Infection and Immunity*, 41:339-344 (1983).
Reuman et al., "Assessment of signs of influenza illness in the ferret model," *Journal of Virological Methods*, 24:27-34 (1989).
Roberts et al., "Regulation of Lymphocyte Proliferation After Influenza Virus Infection of Human Mononuclear Leukocytes", *Journal of Medical Virology*, 27:179-187 (1989).
Roggentin et al., "Diversity in the properties of two sialidase isoenzymes produced by Clostridium perfringens spp," Biological Chemistry Hoppe-Seyler, 376:569-575 (1995).
Roggentin et al., "The sialidase superfamily and its spread by horizontal gene transfer," *Molecular Microbiology*, 9:915-921 (1993).
Root et al., "Targeting therapeutics to an exposed and conserved binding element of the Hiv-1 fusion protein," *Proceedings of the National Academy of Sciences of the United States of America*, 100(9):5016-5021 (2003).
Rosenberg, A. (Ed.), Biology of the Sialic Acids, Plenum Press, New York, N.Y., 270-273, (1995).
Saiman et al., "Comparison of Adherence of Pseudomonas aeruginosa to respiratory Epithelial Cells from Cystic Fibrosis Patients and Healthy Subjects", *Infection and Immunity*, 60:2808-2814 (1992).
Sakurada et al., "Cloning, expression and characterization of the Micromonospora viridifaciens neuraminidase gene in Streptomyces lividans," *Journal of Bacteriology*, 174:6896-6903 (1992).
Schauer, R., (ed.), Sialic Acids Chemistry, Metabolism and Function, Springer-Verlag, Wien, New York, p. 233 (1982).
Schauer, R., "Chemistry, metabolism, and biological functions of sialic acids," *Advances in Carbohydrate Chemistry and Biochemistry*, 40:131-235 (1982).
Scheiblauer et al., "Interactions between bacteria and influenza A virus in the development of influenza pneumonia," *Journal of Infectious Diseases*, 166:783-791 (1992).
Schultze et al., "The S protein of bovine coronavirus is a hemagglutinin recognizing 9-O-acetylated sialic acid as a receptor determinant," *Journal of Virology*, 65:6232-6237 (1991).
Simon et al., "Inhibition of Helicobacter pylori binding to gastrointestinal epithelial cells by sialic acid-containing oligosaccharides," *Infection and Immunity*, 65:750-757 (1997).
Sinn et al., "Measles virus preferentially transduces the basolateral surface of well-differentiated human airway epithelia," *Journal of Virology*, 76:2403-2409 (2002).
Skehel et al., "Receptor binding and membrane fusion in virus entry: the influenza hemagglutinin." *Annu Rev Biochem*, 69:531-569 (2000).
Smith, H. and Sweet, C., "Lessons for human influenza from pathogenicity studies with ferrets," *Reviews of Infectious Diseases*, 10:56-75 (1988).
Sobeslaysky et al., "Adsorption of Mycoplasma pneumoniae to Neuraminic Acid Receptors of Various Cells and Possible Role in Virulence," *Journal of Bacteriology*, 96(3):695-705 (1968).
Solzbacher et al., "Mucin in middle ear effusions inhibits attachment of Haemophilus influenzae to mucosal epithelial cells," *European Archives of Oto-Rhino-Laryngology*, 260:141-147 (2003).
Soriano, F. and V. Rodriguez-Cerrato, "Pharmacodynamic and kinetic basis for the selection of pneumococcal resistance in the upper respiratory tract," *Journal of Antimicrobial Chemotherapy*, 50(S2):51-58 (2002).
Stenton, G., et al., "Proteinase-activated receptor (PAR)-1 and -2 agonists induce mediator release from mast cells by pathways distinct from PAR-1 and PAR-2," *Journal of Pharmacology and Experimental Therapeutics*, 302:466-474 (2002).
Stray, S., et al., "Influenza virus infection of desialylated cells," *Glycobiology*, 10(7):649-658 (2000).

Sutter, V., "Anaerobes as normal oral flora," *Reviews of Infectious Diseases*, 6:S62-S66 (1984).
Suzuki et al., "Receptor Specificities of Human Respiroviruses", *Journal of Virology*, 75(10):4604-4613 (2001).
Tashiro et al., "Inhibitory effect of a protease inhibitor, leupeptin, on the development of influenza pneumonia, mediated by concomitant bacteria," *Journal of General Virology*, 68:2039-2043 (1987).
Tashiro, M., "Synergistic role of staphylococcal proteases in the induction of influenza virus pathogenecity," *Virology*,157:421-430 (1987).
Teufel et al., "Properties of sialidase isolated from *Actinomyces viscosus* DSM43798," *Biological Chemistry Hoppe Seyler*, 370:435-443 (1989).
Thomas, R. and T. Brooks, "Oligosaccharide receptor mimics inhibit *Legionella pneumophila* attachment to human respiratory epithelial cells," *Microbial Pathogenesis*, 36:83-92 (2004).
Thorne, et al., "The Heparin-Binding Domain of Amphiregulin Necessitates the Precursor Pro-Region for Growth Factor Secretion," *Mol. Cell. Biol.*, 14:1635-1646 (1994).
Tobita et al., "Plaque assay and primary isolation of influenza A viruses in an established line of canine kidney cells (MDCK) in the presence of trypsin," *Medical Microbiology and Immunology*, 162:9-14 (1975).
Tringali et al., "Properties of recombinant human cytosolic sialidase HsNEU2. The enzyme hydrolyzes monomerically dispersed GM1 ganglioside molecules," *Journal of Biological Chemistry*, 279(5):3169-3179 (2004).
Umeda et al., "Activity of Human Erythrocyte Gangliosides as a Receptor to HVJ", *Virology* vol. 133:172-182 (1984).
van Alphen et al., "Blocking of fimbria-mediated adherence of *Haemophilus influenzae* by sialyl gangliosides," *Infection and Immunity*, 59:4473-4477 (1991).
Varshaysky, A., "The N-end rule: functions, mysteries, uses," *Proceedings of the National Academy of Sciences of the United States of America*, 93:12142-12149 (1996).
Venturi et al., "High level production of functional antibody Fab fragments in an oxidizing bacterial cytoplasm," *Journal of Molecular Biology*, 315:1-8 (2001).
Verrecchio et al., "Design of Peptides with High Affinities for Heparin and Endothelial Cell Proteoglycans," *J. Biol. Chem.*, 275:7701-7706 (2000).
Vimr, D., "Microbial sialidases: does bigger always mean better,?" *Trends in Microbiology*, 2:271-277 (1994).
Vishwanath et al., "Tracheobronchial Mucin Receptor for Pseudomonas auruginosa: Predominance of Amino Sugars in Binding Sites", *Infection and Immunity*, 48:331-335 (1985).
Vlasak et al., "Human and bovine coronaviruses recognize sialic acid-containing receptors similar to those of influenza C viruses", *Proceedings of the National Academy of Sciences of the United States of America*, 85:4526-4529 (1988).
Wada et al., "Cloning, expression, and chromosomal mapping of a human ganglioside sialidase," *Biochemical and Biophysical Research Communications*, 261:21-27 (1999).
Wagner, J., "Efficient and persistent gene transfer of AAV-CFTR in maxillary sinus," *Lancet,i* 351:1702-1703 (1998).
Wang et al., "Comparison of adenoviral and adeno-associated viral vectors for pancreatic gene delivery in vivo," *Human Gene Therapy*, 15:405-413 (2004).
Wang et al., "Human herpesvirus 8 envelope glycoproteins K8.1A interaction with the target cells involves heparan sulfate," *Journal of Virology*,75:7517-7527 (2001).
Wang et al., "Influence of cell polarity on retrovirus-mediated gene transfer to differentiated human airway epithelia," *Journal of Virology*, 72:9818-9826 (1998).
Wassilewa, L., "Cell receptor for paramyxoviruses," *Archives of Virology*, 54:299-305 (1977).
Weisgraber et al., "Human apoliproprotein E. Determination of the heparin binding sites of apolipoprotein E3," *Journal of Biological Chemistry*, 261(5):2068-2076 (1986).
Wills-Karp et al., "Interleukin-13 in asthma." *Curr. Opin. Pulm. Med.*, 9:21-27 (2003).

(56) References Cited

OTHER PUBLICATIONS

Witt, D. and A. Lander, "Differential binding of chemokines to glycosaminoglycan subpopulations," *Current Biology*, 4:394-400 (1994).
Wood, J., "Developing vaccines against pandemic influenza," *Philosophical Transactions of the Royal Society of London. Series B* 356:1953-1960 (2001).
Wuppermann et al., "Heparan sulfate-like glycosaminoglycan is a cellular receptor for Chlamydia pneumoniae," *Journal of Infectious Diseases*, 184:181-187 (2001).
Wybenga et al., "Glycophorin as a Receptor for Sendai Virus", *Biochemistry*, 35:9513-9518 (1996).
Xiang, Y. and B. Moss, "Molluscum contagiosum virus interleukin-18 (IL-18) binding protein is secreted as a full-length form that bind cell surface glycosaminoglycans through the C-terminal tail and a furin-cleaved form with only the IL-18 binding domain," *Journal of Virology*, 77:2623-2630 (2003).
Yeung, "Complete Nucleotide Sequence of the Actinomyces viscosus T14V Sialidase Gene: Presence of a Conserved Repeating Sequence among Strains of Actinomyces spp.", *Infection and Immunity*, 61(1):109-116 (1993).
Zambon, M., "The pathogenesis of influenza in humans," *Reviews in Medical Virology*, 11:227-241 (2001).
Zhang et al., "Respiratory syncytial virus infection of human airway epithelial cells is polarized, specific to ciliated cells, and without obvious cytopathology," *Journal of Virology*, 76:5654-5666 (2002).
Zhang, "Concerns of using Sialidase Fusion Protein as an experimental drug to Combat Seasonal and Pandemic Influenza", *Journal of Antimicrobial Chemotherapy Advance Access*, 66:426-428 (2008).
Zhang et al, "Infection of Ciliated Cells by Human Parainfluenza Virus Type 3 in an In Vitro Model of Human Airway Epithelium", *Journal of Virology*, 79(2):1113-1124 (2005).
Zhirnov et al., "A modified plaque assay method for accurate analysis of infectivity of influenza viruses with uncleaved hemagglutinin," *Archives of Virology*, 71:177-183 (1982).
Zhirnov et al., "Cleavage of influenza A virus hemagglutinin in human respiratory epithelium is cell associated and sensitive to exogenous antiproteases," *Journal of Virology*, 76:8682-8689 (2002).
Zhirnov et al., "High protection of animals lethally infected with influenza virus by aprotinin-rimantadine combination," *Journal of Medical Virology*, 21:161-167 (1987).
Zhirnov et al., "Myxovirus replication in chicken embryos can be suppressed by aprotinin due to the blockage of viral glycoprotein cleavage," *Journal of General Virology*, 66:1633-1638 (1985).
Zhirnov et al., "Protective effect of protease inhibitors in influenza virus infected animals," *Archives of Virology*, 73:263-272 (1982).
Zhirnov et al., "Suppression of influenza virus replication in infected mice by protease inhibitors," *Journal of General Virology*, 65:191-196 (1984).
Zhirnov, O., "Proteolytic activation of myxoviruses and a new strategy in the treatment of viral diseases," *Soviet Progress in Virology*, 4:9-21 (1983).
Zopf, D. and S. Roth, "Oligosaccharide anti-infective agents," *The Lancet*, 347:1017-1021 (1996).
First Federal Complaint, filed in the United States District Court, Southern District of California, dated Sep. 27, 2005; Case No. 05cv1855 BEN (BLM) *Perland Therapeutics, Inc.* vs. *NexBio, Inc.*, Fang Fang and Mang Yu a California Corporation.
Order granting motion to dismiss and denying plaintiffs motion to exercise supplemental jurisdiction, United States District Court, Southern District of California, dated Aug. 3, 2006; Case No. 05cv1855 BEN (BLM) *Perlan Therapeutics, Inc.* vs. *NexBio, Inc. et al.*

Judgment in a civil case, United States District Court; Southern District of California, dated Aug. 4, 2006; Case No. 05cv1855 BEN (BLM) *Perlan Therapuetics, Inc.* vs. *NexBio, Inc. et al.*
Second Federal Complaint, filed in the United States District Court, Southern District of California, dated Aug. 22, 2006; Case No. 06-CV-1701 WQH (LSP); *Perlan Therapeutics, Inc.* vs. *NexBio, Inc.* A California Corporation, Fanf Fang and Mang Yu.
Order dismissing case without prejudice, United States District Court, Southern District of California, dated Jan. 23, 2007, Case No. 06-CV-1701 WQH (LSP); *Perlan Therapeutics, Inc.* vs *NexBio, Inc.*, a California Corporation, Fang Fang and Mang Yu.
Order dismissing appeal, United States Court of Appeals for the Federal Circuit, dated Feb. 12, 2007; Case No. 05-CV-1855 BEN (BLM); *Perlan Therapeutics, Inc.* vs. *NexBio, Inc.*, a California Corporation, Fanf Fang and Mang Yu.
Second amended complaint for damages and other relief, filed in the Superior Court of the State of California for the County of San Diego dated Apr. 10, 2007; Case No. GIC 871276; *Perlan Therapeutics, Inc.* vs. *NexBio, Inc.*, a California Corporation, Fang Fang M.D. Ph.D., an individual, and MangYu, Ph.D., an individual.
Defendant NexBio, Inc.'s answer to plaintiff's Second Amended Complaint filed in the Superior Court of the State of California for the County of San Diego dated May 15, 2007; Case No. GIC 871276; *Perlan Therapeutics, Inc.* vs. *NexBio, Inc.*, a California Corporation, Fang Fang M.D. Ph.D., an individual, and Mang Yu, Ph.D., an individual.
Defendant Fang Fang M.D., Ph.D.'s, an individual, answer to plaintiff's Second Amended Complaint, filed in the Superior Court of the State of California for the County of San Diego, dated May 15, 2007; Case No. GIC 871276; *Perlan Therapeutics, Inc.* vs. *NexBio, Inc.*, a California Corporation, Fang Fang M.D. Ph.D., an individual, and Mang Yu, Ph.D., an individual.
Defendant Mang Yu, Ph.D.'s answer to plaintiff's Second Amended Complaint, filed in the Superior Court of the State of California for the County of San Diego, dated May 15, 2007; Case No. GIC 871276; *Perlan Therapeutics, Inc.* vs. *NexBio Inc.*, a California Corporation, Fang Fang M.D. Ph.D., an individual, and Mang Yu, Ph.D. an indivdual.
Non-final Office action dated Jun. 9, 2009 for U.S. Appl. No. 10/718,986.
Final Office action dated Oct. 28, 2008 for U.S. Appl. No. 10/718,986.
Non-final Office action dated Mar. 6, 2008 for U.S. Appl. No. 10/718,986.
Final Office action dated Sep. 27, 2007 for U.S. Appl. No. 10/718,986.
Non-final Office action dated Jan. 31, 2007 for U.S. Appl. No. 10/718,986.
Non-final Office action dated Apr. 21, 2009 for U.S. Appl. No. 10/939,262.
Final Office action dated Oct. 24, 2008 for U.S. Appl. No. 10/939,262.
Non-final Office action dated Mar. 26, 2008 for U.S. Appl. No. 10/939,262.
Non-final Office action dated May 22, 2007 for U.S. Appl. No. 10/939,262.
Non-final Office action dated Dec. 18, 2008 for U.S. Appl. No. 11/893,621.
Final Office action dated Sep. 24, 2009 for U.S. Appl. No. 10/893,621.
Non-final Office action dated Jul. 20, 2010 for U.S. Appl. No. 10/893,621.
Final Office action dated Mar. 24, 2011 for U.S. Appl. No. 10/893,621.
Advisory Action dated Jan. 28, 2010 for U.S. Appl. No. 10/718,986.
Final Office action dated May 16, 2010 for U.S. Appl. No. 10/718,986.

\* cited by examiner

PF4 (SEQ ID NO: 2):        $^{47}$NGRRICLDLQAPLYKKIIKKLLES$^{70}$

IL-8 (SEQ ID NO: 3):       $^{46}$GRELCLDPKENWVQRVVEKFLKRAENS$^{72}$

ATIII (SEQ ID NO: 4):      $^{118}$QIHFFFAKLNCRLYRKANKSSKLVSANRLFGDKS$^{151}$

ApoE (SEQ ID NO: 5):       $^{132}$ELRVRLASHLRKLRKRLLRDADDLQKRLAVYQAG$^{165}$

AAMP (SEQ ID NO: 6):       $^{17}$RRLRRMESESES$^{25}$

Amphiregulin (SEQ ID NO: 7): $^{125}$KRKKKGGKNGKNRRNRKKKNP$^{145}$

FIG. 2

```
NEU2(SEQ ID NO:8):   1  MASLPVLQKE  SVFQSGAHA-  -YRIPALLYL  PGQQSLLAFA  EQRASKKDEH
                                                YR+P+LL +   P           +LLAF EQR S    D E
NEU4(SEQ ID NO:9):   1  MGVPRTPSRT  VLFERERTGL  TYRVPSLLPV  PPGPTLLAFV  EQRLSPDDSH

NEU2:  49  AELIVLRRGD  YDAPTHQVQW  QAQEVVAQAR  LDGHRSMNPC  PLYDAQTGTL  FLFFIAIPGQ
           A +VLRRG                +W  A  ++  A            HRSMNPC P++DA TGT+  FLFFIA+ G
NEU4:  51  AHRLVLRRGT  LAGGSV---RW  GALHVLGTAA  LAEHRSMNPC  PVHDAGTGTV  FLFFIAVLGH

NEU2: 110  VTEQQQLQTR  ANVTRLCQVT  STDHGRTWSS  PRDLTDAAIG  PAYREWSTFA  VGPGHCLQLN
             E  Q+ T    N  RLC V    S D G +W S   RDLT+ AIG   A ++W+TFA  VGPGH +QL
NEU4: 109  TPEAVQIATG  RNAARLCCVA  SRDAGLSWGS  ARDLTEEAIG  GAVQDWATFA  VGPGHGVQLP

NEU2: 170  DRARSLVVPA  YAYRKLHP--  ---IQRPIPS  AFCFLSHDHG  RTWARGHFVA  QD-TLECQVA
               R L+VPA  Y  YR              I R P  +F F S DHG  RTW  G   V     +  ECQ+A
NEU4: 169  S-GR-LLVPA  YTYRVDRLEC  FGKICRTSPH  SFAFYSDDHG  RTWRCGGLVP  NLRSGECQLA

NEU2: 224  EVETGEQRVV  TL-NARSHLR  ARVQAQSTND  GLDFQESQLV  KKLVEPPPQG  CQGSVISFPS
             V+  G+              NARS L   +RVQA ST++  G F  ++ V   L E      G  CQGS++  FP
NEU4: 227  AVDGGQAGSF  LYCNARSPLG  SRVQALSTDE  GTSFLPAERV  ASLPETAW-G  CQGSIVGFPA

NEU2: 283  P---------  ----------  ----------  ----------  ----------  ----------

NEU4: 286  PAPNRPRDDS  WSVGPRSPLQ  PPLLGPGVHE  PPEEAAVDPR  GGQVPGGPFS  RLQPRGDGP

NEU2: 284  ----------  ----------  ---RSGPGSP  QWLLYTHPTH  SWQRADLGAY  LNPRPPAPEA
                                              WLLY+HP        R  +G    L+   P  P +
NEU4: 346  RQPGPRPGVSG  DVGSWTLALP  MPFAAPPQSP  TWLLYSHPVG  RRARLHMGIR  LSQSPLDPRS

NEU2: 321  WSEPVLLAKG  SCAYSDLQSM  GTGPDGSPLF  GCLYEANDY-  ---EEIVFLMF  TLKQAFPAEY
           W+EP ++ +               YSDL S+ G   P+G   +F  +CLYE                 +L++
NEU4: 406  WTEPWVIYEG  PSGYSDLASI  GPAPEGGLVF  ACLYESGART  SYDEISFCTF  SLREVLENVP

NEU2: 378  LPQ

NEU4: 466  ASPKPPNLGD  KPRGCCWPS
```

FIG. 3

Substrate Specificity of Bacteria and Fungal Sialidases

| Substrates | Sialidase activity* | | | | | |
|---|---|---|---|---|---|---|
| | Vibrio Cholerae (71Kd) | Clostridium perfringens | Clostridium perfringens (43Kd) | Arthrobacter ureafaciens | Salmonella typhimurium | Actinomyces viscosus |
| Oligo-and polysaccharides | | | | | | |
| II³Neu5AcLac | 100 | 100 | 100 | 100 | 100 | 100 |
| II⁶Neu5AcLac | 53 | 44 | 19 | 157 | 0.4 | 462 |
| Colominic acid (α2-8) | 30 | 33 | 4.0 | 63 | 0.1 | 300 |
| Glycoproteins | | | | | | |
| Fetuin (α2-3>α2-6) | 340 | 272 | 6.6 | 59 | 17 | — |
| α1-Acid glycoprotein (α2-6>α2-3) | 1000 | 555 | — | — | — | 761 |
| Submandibular gland mucin (α2-6) | 400 | 139 | 5.1 | — | — | 123 |
| Submaxillary gland mucin (α2-6) | — | — | — | 56 | — | — |
| Gangliosides | | | | | | |
| Gangliosides mixtures | (360) | (350) | 1.6 | 78 | 34 | 285 |
| Synthetic | | | | | | |
| 4MU-Neu5Ac | 1580 | 605 | 58 | — | 1050 | — |

* Each value represents a relative sialidase activity when activity directed toward II³Neu5AcLac is regard as 100.

FIG. 4

```
ccatggggcatcaccatcaccatcatctagagggagatcatccacaagctacaccagcacct
  M  G  H  H  H  H  H  L  E  G  D  H  P  Q  A  T  P  A  P
gcaccagatgctagcactgagctgccagcaagcatgtctcaggctcagcatcttgcagca
 A  P  D  A  S  T  E  L  P  A  S  M  S  Q  A  Q  H  L  A  A
aatacggctactgataattatcgcattccagcgattacaaccgctccgaatggtgattta
 N  T  A  T  D  N  Y  R  I  P  A  I  T  T  A  P  N  G  D  L
ctgattagctatgatgaacggccgaaggacaatggaaatggtggttccgatgcccctaac
 L  I  S  Y  D  E  R  P  K  D  N  G  G  S  D  A  P  N
ccgaatcatattgttcagcgtcgctccacagatggcggtaaaacttggagcgcgccaacc
 P  N  H  I  V  Q  R  R  S  T  D  G  G  K  T  W  S  A  P  T
tatattcatcagggtacggagactggcaagaaagtgggatattccgacccctcttatgtg
 Y  I  H  Q  G  T  E  T  G  K  K  V  G  Y  S  D  P  S  Y  V
gtggatcatcaaaccggtacaatcttcaattttcatgtgaaatcatacgatcagggctgg
 V  D  H  Q  T  G  T  I  F  N  F  H  V  K  S  Y  D  Q  G  W
ggaggtagccgtgggggaacagacccggaaaaccgcggattattcaggcagaggtgtct
 G  G  S  R  G  G  T  D  P  E  N  R  G  I  I  Q  A  E  V  S
acgagcacggataatggatggacgtggacacatcgcaccatcaccgcggatattacgaaa
 T  S  T  D  N  G  W  T  W  T  H  R  T  I  T  A  D  I  T  K
gataaaccgtggaccgcgcgttttgcggcgtccggccaaggcattcagatccagcatggg
 D  K  P  W  T  A  R  F  A  A  S  G  Q  G  I  Q  I  Q  H  G
ccgcatgccggccgtctggtgcaacagtataccattcgtacggccggtggagcggtgcag
 P  H  A  G  R  L  V  Q  Q  Y  T  I  R  T  A  G  G  A  V  Q
gctgtatcggtttattccgatgatcatgggaaaacgtggcaggctggcaccccgattggg
 A  V  S  V  Y  S  D  D  H  G  K  T  W  Q  A  G  T  P  I  G
acgggtatggatgaaaacaaagttgtagagctgtctgacggctctctgatgctgaacagt
 T  G  M  D  E  N  K  V  V  E  L  S  D  G  S  L  M  L  N  S
cgtgcgtcggacgggagcggctttcgtaaggttgcgcatagcactgatggtgggcagacc
 R  A  S  D  G  S  G  F  R  K  V  A  H  S  T  D  G  G  Q  T
tggtccgaaccggtttcggacaaaaatttgccggattcggttgataatgcccagataatt
 W  S  E  P  V  S  D  K  N  L  P  D  S  V  D  N  A  Q  I  I
cgtgcgtttcctaatgctgccccgatgacccgcgcgcgaaagtacttcttctgagtcat
 R  A  F  P  N  A  A  P  D  D  P  R  A  K  V  L  L  L  S  H
tccccaaatccacgtccgtggtcccgggatcgtggtacgataagcatgtcatgtgatgac
 S  P  N  P  R  P  W  S  R  D  R  G  T  I  S  M  S  C  D  D
ggggcctcatggaccacttccaaagttttcacgaaccgtttgtgggctacacgactatt
 G  A  S  W  T  T  S  K  V  F  H  E  P  F  V  G  Y  T  T  I
gcagttcagagtgatggaagcatcggtctgctgtcggaggacgcgcacaatggcgctgat
 A  V  Q  S  D  G  S  I  G  L  L  S  E  D  A  H  N  G  A  D
tatggtggcatctggtatcgtaattttacgatgaactggctgggagaacaatgtggacaa
 Y  G  G  I  W  Y  R  N  F  T  M  N  W  L  G  E  Q  C  G  Q
aaacccgcggaataagctt
 K  P  A  E
```

FIG. 5

```
ccatggttaagcgcaaaaaaaaggcggcaaaaacggtaaaaatcgtcgtaaccgtaagaaa
    M  V  K  R  K  K  K  G  G  K  N  G  K  N  R  R  N  R  K  K
aaaaatcctggagatcatccacaagctacaccagcacctgcaccagatgctagcactgag
   K  N  P  G  D  H  P  Q  A  T  P  A  P  A  P  D  A  S  T  E
ctgccagcaagcatgtctcaggctcagcatcttgcagcaaatacggctactgataattat
   L  P  A  S  M  S  Q  A  Q  H  L  A  A  N  T  A  T  D  N  Y
cgcattccagcgattacaaccgctccgaatggtgatttactgattagctatgatgaacgg
   R  I  P  A  I  T  T  A  P  N  G  D  L  L  I  S  Y  D  E  R
ccgaaggacaatggaaatggtggttccgatgcccctaacccgaatcatattgttcagcgt
   P  K  D  N  G  N  G  G  S  D  A  P  N  P  N  H  I  V  Q  R
cgctccacagatggcggtaaaacttggagcgcgccaacctatattcatcagggtacggag
   R  S  T  D  G  G  K  T  W  S  A  P  T  Y  I  H  Q  G  T  E
actggcaagaaagtgggatattccgacccctcttatgtggtggatcatcaaaccggtaca
   T  G  K  K  V  G  Y  S  D  P  S  Y  V  V  D  H  Q  T  G  T
atcttcaattttcatgtgaaatcatacgatcagggctggggaggtagccgtgggggaaca
   I  F  N  F  H  V  K  S  Y  D  Q  G  W  G  G  S  R  G  G  T
gacccggaaaaccgcgggattattcaggcagaggtgtctacgagcacggataatggatgg
   D  P  E  N  R  G  I  I  Q  A  E  V  S  T  S  T  D  N  G  W
acgtggacacatcgcaccatcaccgcggatattacgaaagataaaccgtggaccgcgcgt
   T  W  T  H  R  T  I  T  A  D  I  T  K  D  K  P  W  T  A  R
tttgcggcgtccggccaaggcattcagatccagcatgggccgcatgccggccgtctggtg
   F  A  A  S  G  Q  G  I  Q  I  Q  H  G  P  H  A  G  R  L  V
caacagtataccattcgtacggccggtggagcggtgcaggctgtatcggtttattccgat
   Q  Q  Y  T  I  R  T  A  G  G  A  V  Q  A  V  S  V  Y  S  D
gatcatgggaaaacgtggcaggctggcaccccgattgggacgggtatggatgaaaacaaa
   D  H  G  K  T  W  Q  A  G  T  P  I  G  T  G  M  D  E  N  K
gttgtagagctgtctgacggctctctgatgctgaacagtcgtgcgtcggacgggagcggc
   V  V  E  L  S  D  G  S  L  M  L  N  S  R  A  S  D  G  S  G
tttcgtaaggttgcgcatagcactgatggtgggcagacctggtccgaaccggtttcggac
   F  R  K  V  A  H  S  T  D  G  G  Q  T  W  S  E  P  V  S  D
aaaaatttgccggattcggttgataatgcccagataattcgtgcgtttcctaatgctgcc
   K  N  L  P  D  S  V  D  N  A  Q  I  I  R  A  F  P  N  A  A
cccgatgacccgcgcgcgaaagtacttcttctgagtcattccccaaatccacgtccgtgg
   P  D  D  P  R  A  K  V  L  L  L  S  H  S  P  N  P  R  P  W
tcccgggatcgtggtacgataagcatgtcatgtgatgacggggcctcatggaccacttcc
   S  R  D  R  G  T  I  S  M  S  C  D  D  G  A  S  W  T  T  S
aaagttttcacgaaccgtttgtgggctacacgactattgcagttcagagtgatggaagc
   K  V  F  H  E  P  F  V  G  Y  T  T  I  A  V  Q  S  D  G  S
atcggtctgctgtcggaggacgcgcacaatggcgctgattatggtggcatctggtatcgt
   I  G  L  L  S  E  D  A  H  N  G  A  D  Y  G  G  I  W  Y  R
aattttacgatgaactggctgggagaacaatgtggacaaaaacccgcggaataagctt
   N  F  T  M  N  W  L  G  E  Q  C  G  Q  K  P  A  E  -  A
```

FIG. 6

```
ccatggttaagcgcaaaaaaaaggcggcaaaaacggtaaaaatcgtcgtaaccgtaagaaa
    M  V  K  R  K  K  K  G  G  K  N  G  K  N  R  R  N  R  K  K
aaaaatcctggtggtggtggttctggagatcatccacaagctacaccagcacctgcacca
    K  N  P  G  G  G  S  G  D  H  P  Q  A  T  P  A  P  A  P
gatgctagcactgagctgccagcaagcatgtctcaggctcagcatcttgcagcaaatacg
    D  A  S  T  E  L  P  A  S  M  S  Q  A  Q  H  L  A  A  N  T
gctactgataattatcgcattccagcgattacaaccgctccgaatggtgatttactgatt
    A  T  D  N  Y  R  I  P  A  I  T  T  A  P  N  G  D  L  L  I
agctatgatgaacggccgaaggacaatggaaatggtggttccgatgcccctaacccgaat
    S  Y  D  E  R  P  K  D  N  G  N  G  G  S  D  A  P  N  P  N
catattgttcagcgtcgctccacagatggcggtaaaacttggagcgcgccaacctatatt
    H  I  V  Q  R  R  S  T  D  G  G  K  T  W  S  A  P  T  Y  I
catcagggtacggagactggcaagaaagtgggatattccgacccctcttatgtggtggat
    H  Q  G  T  E  T  G  K  K  V  G  Y  S  D  P  S  Y  V  V  D
catcaaaccggtacaatcttcaattttcatgtgaaatcatacgatcagggctggggaggt
    H  Q  T  G  T  I  F  N  F  H  V  K  S  Y  D  Q  G  W  G  G
agccgtggggaacagacccggaaaaccgcgggattattcaggcagaggtgtctacgagc
    S  R  G  T  D  P  E  N  R  G  I  I  Q  A  E  V  S  T  S
acggataatggatggacgtggacacatcgcaccatcaccgcggatattacgaaagataaa
    T  D  N  G  W  T  W  T  H  R  T  I  T  A  D  I  T  K  D  K
ccgtggaccgcgcgttttgcggcgtccggccaaggcattcagatccagcatgggccgcat
    P  W  T  A  R  F  A  A  S  G  Q  G  I  Q  I  Q  H  G  P  H
gccggccgtctggtgcaacagtataccattcgtacggccggtggagcggtgcaggctgta
    A  G  R  L  V  Q  Q  Y  T  I  R  T  A  G  G  A  V  Q  A  V
tcggtttattccgatgatcatgggaaaacgtggcaggctggcaccccgattgggacgggt
    S  V  Y  S  D  D  H  G  K  T  W  Q  A  G  T  P  I  G  T  G
atggatgaaaacaaagttgtagagctgtctgacggctctctgatgctgaacagtcgtgcg
    M  D  E  N  K  V  V  E  L  S  D  G  S  L  M  L  N  S  R  A
tcggacgggagcggctttcgtaaggttgcgcatagcactgatggtgggcagacctggtcc
    S  D  G  S  G  F  R  K  V  A  H  S  T  D  G  G  Q  T  W  S
gaaccggtttcggacaaaaatttgccggattcggttgataatgcccagataattcgtgcg
    E  P  V  S  D  K  N  L  P  D  S  V  D  N  A  Q  I  I  R  A
tttcctaatgctgccccgatgacccgcgcgcgaaagtacttcttctgagtcattcccca
    F  P  N  A  A  P  D  D  P  R  A  K  V  L  L  L  S  H  S  P
aatccacgtccgtggtcccgggatcgtggtacgataagcatgtcatgtgatgacggggcc
    N  P  R  P  W  S  R  D  R  G  T  I  S  M  S  C  D  D  G  A
tcatggaccacttccaaagttttttcacgaaccgtttgtgggctacacgactattgcagtt
    S  W  T  T  S  K  V  F  H  E  P  F  V  G  Y  T  T  I  A  V
cagagtgatggaagcatcggtctgctgtcggaggacgcgcacaatggcgctgattatggt
    Q  S  D  G  S  I  G  L  L  S  E  D  A  H  N  G  A  D  Y  G
ggcatctggtatcgtaattttacgatgaactggctgggagaacaatgtggacaaaaaccc
    G  I  W  Y  R  N  F  T  M  N  W  L  G  E  Q  C  G  Q  K  P
gcggaataagctt
    A  E  -  A
```

FIG. 7

| Virus | AR-AvCD | | | | AR-$G_4$S-AvCD | | | |
|---|---|---|---|---|---|---|---|---|
| | Inhibition of Viral Replication EC50 | Selective Index | Cell Protection EC50 | Selective Index | Inhibition of Viral Replication EC50 | Selective Index | Cell Protection EC50 | Selective Index |
| A/PR/8/34 (H1N1) | 12.3 ± 7.4 | >8163 | 50.3 ± 13.1 | >1990 | 13.5 ± 1.4 | >7407 | 43.8 ± 22.3 | >2286 |
| A/WS/33 (H1N1) | 6.5 ± 3.9 | >15444 | 17.7 ± 13.9 | >5666 | 12.2 ± 11.0 | >8197 | 19.1 ± 17.6 | >5249 |
| A/NWS/33 (H1N1 | 2.5 | >20000 | 10.8 ± 12.4 | >9302 | 2.5 | >40000 | 15.9 ± 19.3 | >6249 |
| A/Japan/305/57 (H2N2) | 5.1 ± 3.4 | >19512 | 11.3 ± 0.4 | >8889 | 3.8 ± 1.8 | >26667 | 14.9 ± 0.2 | >6273 |
| A/Victoria/504/2000 (H3N2) | 2.5 ± 0.0 | >40000 | 18.3 ± 1.0 | >5457 | 2.6 ± 0.2 | >38095 | 55.3 ± 0.4 | >1810 |
| A/HongKong/8/68 (H3N2) | 2.5 ± 0.0 | >40000 | 31.5 ± 38.2 | >3175 | 2.5 ± 0.0 | >40000 | 30.6 ± 30.2 | >3265 |
| B/Lee/40 | 4.1 ± 1.3 | >24540 | 11.4 ± 3.7 | >8791 | 3.5 ± 1.3 | >28986 | 8.4 ± 2.7 | >11940 |
| B/Maryland/1/59 | 4.3 ± 2.5 | >23392 | 2.5 ± 0.0 | >40000 | 5.5 ± 1.3 | >18265 | 5.6 ± 3.0 | >17778 |
| Turkey/Wis/66 (H9N2) | 3.9 ± 0.5 | >25478 | 16.6 ± 16.2 | >6033 | 7.1 ± 0.9 | >14035 | 20.4 ± 18.6 | >4914 |
| Equine/Prague/2/62 (H7N7) | n/a | n/a | 15.8 ± 5.3 | >6349 | n/a | n/a | 25.5 ± 5.7 | >3922 |

FIG. 12

| No. | Ferret tag no. | Virus titer log$_{10}$ TCID$_{50}$/ml on day p.i.[a] | | | | Post challenge HI titers |
|---|---|---|---|---|---|---|
| | | Vehicle-treated group | | | | |
| 1 | 228 | 5.7 | 4.2 | 4.2 | 1.7 | 640 |
| 2 | 784 | 3.9 | 4.9 | 1.9 | 1.9 | 640 |
| 3 | 793 | 4.4 | 4.2 | 2.4 | 3.9 | 640 |
| 4 | 794 | 4.9 | 5.9 | 1.4 | - | 160 |
| 5 | 789 | 4.4 | 4.2 | 3.4 | 3.4 | 640 |
| 6 | 799 | 3.7 | 4.4 | 3.4 | - | 320 |
| 7 | 811 | 4.4 | 4.4 | - | - | 1280 |
| 8 | 841 | 4.2 | 4.7 | 2.7 | 1.9 | 320 |
| | mean[b] | 4.4 | 4.7 | 2.7 | 3.7 | |
| | SD | 0.4 | 0.7 | 1.0 | 0.4 | |
| | Shed/total | 8/8 | 8/8 | 7/8 | 5/8 | |
| | | Fludase-treated group | | | | |
| 1 | 780 | - | - | - | NA | NA |
| 2 | 791 | 2.2 | 5.2 | 4.9 | 4.2 | 640 |
| 3 | 804 | - | 4.7 | 3.7 | 1.7 | 1280 |
| 4 | 803 | - | - | - | - | ≤10 |
| 5 | 805 | - | - | - | - | ≤10 |
| 6 | 806 | - | - | - | - | ≤10 |
| 7 | 810 | 2.2 | 4.7 | 3.2 | 2.9 | 160 |
| 8 | 812 | - | 3.2 | 4.4 | - | 640 |
| 9 | 813 | - | 4.4 | 4.7 | - | 160 |
| 10 | 819 | 2.7 | - | 1.7 | - | 320 |
| 11 | 828 | - | 5.2 | 4.9 | 1.7 | 320 |
| 12 | 843 | - | 4.4 | 4.9 | 3.4 | 320 |
| | mean[b] | 2.4 | 4.6 | 3.9 | 3.4 | |
| | SD | 0.3 | 0.7 | 1.1 | 2.6 | |
| | Shed/total | 3/12 | 7/12 | 6/11 | 1.2 / 2/11 | |

[a] — all nasal washes collected after day 5 post challenge were negative for virus presence.
[b] — mean value was calculated for the ferrets that shed virus.

FIG. 13

CLASS OF THERAPEUTIC PROTEIN BASED MOLECULES

CROSS-REFERENCE TO RELATED APPLICATIONS

This application is a continuation of U.S. application of Ser. No. 14/274,912, filed May 12, 2014, which is a continuation of U.S. application Ser. No. 13/970,229, filed Aug. 19, 2013, which is a continuation of U.S. application Ser. No. 12/861,392, filed Aug. 23, 2010, entitled "A Novel Class of Therapeutic Protein Based Molecules", which is a continuation of U.S. application Ser. No. 10/939,262, filed Sep. 10, 2004, entitled "A Novel Class of Therapeutic Protein Based Molecules", which claims benefit of priority to U.S. Provisional Application No. 60/561,749, filed Apr. 13, 2004, entitled "Anti-microbial therapeutics and prophylaxis", and benefit of priority to U.S. Provisional Application No. 60/580,084, filed Jun. 16, 2004, entitled "Class of broad spectrum anti-microbial agents." The aforementioned applications are all herein incorporated by reference.

BACKGROUND OF THE INVENTION

The invention relates to therapeutic compositions that can be used to prevent and treat infection of human and animal subjects by a pathogen, and specifically to protein-based therapeutic compositions that can be used for the prevention and treatment of viral or bacterial infections. The invention also relates to therapeutic protein-based compositions that can be used to prevent or ameliorate allergic and inflammatory responses. The invention also relates to protein-based compositions for increasing transduction efficiency of a recombinant virus, such as a recombinant virus used for gene therapy.

Influenza is a highly infectious acute respiratory disease that has plagued the human race since ancient times. It is characterized by recurrent annual epidemics and periodic major worldwide pandemics. Because of the high disease-related morbidity and mortality, direct and indirect social economic impacts of influenza are enormous. Yearly epidemics cause approximately 300,000 hospitalizations and 25,000 deaths in the United States alone. Four pandemics occurred in the last century; together they caused tens of millions of deaths. Mathematical models based on earlier pandemic experiences have estimated that 89,000-207,000 deaths, 18-42 million outpatient visits and 20-47 million additional illnesses will occur during the next pandemic (Meltzer, M I, Cox, N J and Fukuda, K. (1999) *Emerg Infect Dis* 5:659-671).

Influenza is typically caused by infection of two types of viruses, Influenza virus A and Influenza virus B (the third type Influenza virus C only causes minor common cold like symptoms). They belong to the orthomyxoviridae family of RNA viruses. Both type A and type B viruses have 8 segmented negative-strand RNA genomes enclosed in a lipid envelope derived from the host cell. The viral envelope is covered with spikes that are composed of three types of proteins: hemagglutinin (HA) which attaches virus to host cell receptors and mediates fusion of viral and cellular membranes; neuraminidase (NA) which facilitates the release of the new viruses from host cells; and a small number of M2 proteins which serve as ion channels.

Infections by influenza type A and B viruses are typically initiated at the mucosal surface of the upper respiratory tract. Viral replication is primarily limited to the upper respiratory tract but can extend to the lower respiratory tract and cause bronchopneumonia that can be fatal.

Influenza viral protein hemagglutinin (HA) is the major viral envelope protein. It plays an essential role in viral infection. The importance of HA is evidenced by the fact that it is the major target for protective neutralizing antibodies produced by the host immune response (Hayden, F G. (1996) In *Antiviral drug resistance* (ed. D. D. Richman), pp. 59-77. Chichester, U K: John Wiley & Sons Ltd.). It is now clear that HA has two different functions in viral infection. First, HA is responsible for the attachment of the virus to sialic acid cell receptors. Second, HA mediates viral entry into target cells by triggering fusion of the viral envelope with cellular membranes.

HA is synthesized as a precursor protein, HA0, which is transferred through the Golgi apparatus to the cell surface as a trimeric molecular complex. HA0 is further cleaved to generate the C terminus HA1 (residue 328 of HA0) and the N terminus of HA2. It is generally believed that the cleavage occurs at the cell surface or on released viruses. The cleavage of HA0 into HA1/HA2 is not required for HA binding to sialic acid receptor; however, it is believed to be necessary for viral infectivity (Klenk, H D and Rott, R. (1988) *Adv Vir Res*. 34:247-281; Kido, H, Niwa, Y, Beppu, Y and Towatari, T. (1996) *Advan Enzyme Regul* 36:325-347; Skehel, J J and Wiley, D C. (2000) *Annu Rev Biochem* 69:531-569; Zambon, M. (2001) *Rev Med Virol* 11:227-241.)

Currently, influenza is controlled by vaccination and anti-viral compounds. Inactivated influenza vaccines are now in worldwide use, especially in high-risk groups. The vaccine viruses are grown in fertile hen's eggs, inactivated by chemical means and purified. The vaccines are usually trivalent, containing representative influenza A viruses (H1N1 and H3N2) and influenza B strains. The vaccine strains need to be regularly updated in order to maintain efficacy; this effort is coordinated by the World Health Organization (WHO). During inter-pandemic periods, it usually takes 8 months before the updated influenza vaccines are ready for the market (Wood, J. (2001) *Phil Trans R Soc Lond B* 356:1953-1960). However, historically, pandemics spread to most continents within 6 months, and future pandemics are expected to spread even faster with increased international travel (Gust, I D, Hampson, A W., and Lavanchy, D. (2001) *Rev Med Virol* 11:59-70). Therefore it is inevitable that an effective vaccine will be unavailable or in very short supply during the first waves of future pandemics.

Anti-viral compounds have become the mainstay for treating inter-pandemic diseases. Currently, they are also the only potential alternative for controlling pandemics during the initial period when vaccines are not available. Two classes of antiviral compounds are currently on the market: the M2 inhibitors, such as amantadine and rimantadine; and the NA inhibitors, which include oseltamivir (Tamiflu) and zanamivir (Relenza). Both classes of molecules have proven efficacy in prevention and treatment of influenza. However, side effects and the risk of generating drug-resistant viruses remain the top two concerns for using them widely as chemoprophylaxis (Hayden, F G. (1996) In *Antiviral drug resistance* (ed. D. D. Richman), pp. 59-77. Chichester, U K: John Wiley & Sons Ltd.). Most importantly, future pandemic strains, either evolved naturally or artificially created by genetic engineering in bio-warfare, may be resistant to all the available anti-viral compounds, and this will have devastating consequences globally.

In summary, currently available vaccination and anti-viral compounds are limited by some fundamental shortcomings.

Novel therapeutic and prophylactic modalities are needed to address future influenza pandemics.

Respiratory tract infections (RTIs) are the most common, and potentially most severe, types of infectious diseases. Clinically, RTIs include sinusitis, otitis, laryngitis, bronchitis and pneumonia. Based on numerous etiology and epidemiology studies, it is clear that although many microorganisms have the potential to cause RTIs, only a handful of pathogens are responsible for vast majority of the cases. Such pathogens include *S. pneumoniae, M. pneumoniae, H. influenzae, M. catarrhalis*, influenza A & B, and parainfluenza virus. Besides causing CAP and AECB, several of the bacterial pathogens, such as *S. pneumoniae* and *H. influenzae*, are also the common cause of acute sinusitis, otitis media, as well as invasive infections leading to sepsis, meningitis, etc. Therefore these microorganisms are of the highest clinical importance.

One common feature of all respiratory pathogenic bacteria is that they establish commensal colonization on the mucosal surface of the upper airway; such colonization precedes an infection and is prerequisite for infections. The bacterial colonization in a neonate occurs shortly after birth. During lifetime, the upper airway, specifically the nasopharynx and oropharynx, remains a dynamic ecological reservoir of microbial species with bacteria being acquired, eliminated and re-acquired continually. In most cases the bacterial flora in the pharynx is harmless. However, when the condition of the host is altered, some microorganisms may invade adjacent tissues or bloodstream to cause diseases. In addition to serving as the port of entry for mucosal and invasive infections by both bacteria and viruses, the nasopharynx is also the major source of spreading the pathogenic microorganisms between individuals, as well as the reservoir where antibiotic-resistant bacteria are selected (Garcia-Rodriguez and Martinez, J Antimicrob Chemother, (2002) 50 (Suppl S2), 59-73; Soriano and Rodriguez-Cerrato, J Antimicrob Chemother, (2002) 50 (Suppl S2), 51-58). It is well established clinically that individuals who are prone to RTIs tend to be persistent and recurrent carriers of the pathogenic bacteria (Garcia-Rodriguez and Martinez, J Antimicrob Chemother, (2002) 50 (Suppl S2), 59-73; Mbaki et al., Tohoku J Exp. Med., (1987) 153(2), 111-121).

*Helicobacter pylori* is a human pathogen implicated in gastritis and peptic ulcer. The bacterium resides in the human stomach and binds to epithelial cells of the gastric antrum. It has been demonstrated that the bacterial adhesion is mediated by binding of *Helicobacter pylori* adhesin I and II to sialic acids on the epithelial surface.

Siglecs (sialic acid binding Ig-like lectins) are members of the immunoglobulin (Ig) superfamily that bind to sialic acid and are mainly expressed by cells of the hematopoietic system. At least 11 siglecs have been discovered and they seem to exclusively recognize cell surface sialic acid as the ligand. It is believed that the binding of siglecs to sialic acid mediates cell-cell adhesion and interactions (Crocker and Varki, Trends Immunol., (2001) 22(6), 337-342; Angata and Brinkman-Van der Linden, Biochim. Biophys. Acta, (2002) 1572(2-3), 294-316). Siglec-8 (SAF-2) is an adhesion molecule that is highly restricted to the surface of eosinophils, basophils, and mast cells, which are the central effector cells in allergic conditions including allergic rhinitis, asthma and eczema. Siglec-8 is considered to be responsible for mediating the recruitment of the three allergic cell types to the airway, the lungs and other sites of allergy. Siglec-1 (sialoadhesion) and siglec-2 (CD22) are the adhesion molecules on macrophages and B cells, both types of cells play central roles in immune reactions that lead to inflammation.

Recombinant viruses, in particular adeno-associated virus (AAV), can be used to transfer the wild type cystic fibrosis transmembrane conductance regulator (CFTR) gene into the epithelial cells to correct the genetic defect that causes cystic fibrosis (Flotte and Carter, Methods Enzymol., (1998) 292, 717-732). Clinical trials with AAV vectors have shown efficient and safe delivery of the CFTR gene into epithelial cells with low levels of gene transfer (Wagner et al., Lancet, (1998) 351(9117), 1702-1703). Compared to adenoviral vectors, AAV offers more stable gene expression and diminished cellular immunity. However, the transduction efficiency of AAV in vivo is rather low in the lung (Wagner et al., Lancet, (1998) 351(9117), 1702-1703). A method that can improve transduction efficiency of AAV in vivo is needed to achieve full therapeutic potential of gene therapy for cystic fibrosis. It has been shown that negatively charged carbohydrates, such as sialic acid, inhibit the transduction efficiency of AAV vector to the well-differentiated airway epithelium, and treatment of the airway epithelium by glycosidases, including a neuraminidase, and endoglycosidase H, enhances transduction efficiency of the AAV vector (Bals et al., J Virol., (1999) 73(7), 6085-6088).

BRIEF SUMMARY OF THE INVENTION

The present invention recognizes that current therapeutics for preventing and treating infection by pathogens are often difficult to provide in a timely manner, can have undesirable side effects, and can lead to drug-resistant pathogen strains. The present invention also recognizes that the current approach to treat allergy and inflammation has limited efficacy and is associated with side effects. In addition, the present invention also recognizes that the current approach to administer recombinant viruses yield low transduction efficiency and unsatisfactory efficacy of the gene therapy.

The present invention provides new compositions and methods for preventing and treating pathogen infection. In particular, the present invention provides compounds that can act extracellularly to prevent infection of a cell by a pathogen. Some preferred embodiments of the present invention are therapeutic compounds having an anchoring domain that anchors the compound to the surface of a target cell, and a therapeutic domain that can act extracellularly to prevent infection of the target cell by a pathogen, such as a virus or bacterium.

In one aspect, the invention provides a protein-based composition for preventing or treating infection by a pathogen. The composition comprises a compound that comprises at least one therapeutic domain comprising a peptide or protein, where the therapeutic domain has at least one extracellular activity that can prevent the infection of a target cell by a pathogen, and at least one anchoring domain that can bind at or near the membrane of a target cell.

In some embodiments of this aspect of the present invention, the at least one therapeutic domain comprises an inhibitory activity that prevents or impedes the infection of a target cell by a pathogen. In a preferred embodiment, the inhibitory activity inhibits the activity of a protease that can process a viral protein necessary for infection of a target cell. In a particularly preferred embodiment, the compound comprises a therapeutic domain that can inhibit the processing of the HA protein of influenza virus, and the anchoring domain can bind the compound at the surface of a respiratory epithelial cell.

In some embodiments of the present invention, at least one therapeutic domain comprises a catalytic activity. In a preferred embodiment, the catalytic activity removes a moiety from the surface of a target cell that is necessary for infection of the target cell. In a particularly preferred embodiment, the therapeutic domain is a sialidase that can digest sialic acid moieties on the surface of epithelial target cells, and the anchoring domain is a GAG-binding domain of a human protein that can bind heparin or heparan sulfate moieties at the surface of an epithelial cell.

In another aspect, the present invention includes pharmaceutical compositions for treating or preventing pathogen infection in a subject. Pharmaceutical compositions comprise a compound of the present invention comprising at least one therapeutic domain and at least one anchoring domain. The pharmaceutical composition can also comprise solutions, stabilizers, fillers and the like. In some preferred embodiments, the pharmaceutical composition is formulated as an inhalant. In some preferred embodiments, the pharmaceutical composition is formulated as a nasal spray.

Another aspect of the present invention is a pharmaceutical composition comprising at least one sialidase. The sialidase can be isolated from any source, such as, for example, a bacterial or mammalian source, or can be a recombinant protein that is substantially homologous to a naturally occurring sialidase. A pharmaceutical composition comprising a sialidase can be formulated for nasal, tracheal, bronchial, oral, or topical administration, or can be formulated as an injectable solution or as eyedrops. A pharmaceutical composition comprising a sialidase can be used to treat or prevent pathogen infection, to treat or prevent allergy or inflammatory response, or to enhance the transduction efficiency of a recombinant virus for gene therapy.

Yet another aspect of the present invention is a sialidase catalytic domain protein. In this aspect, proteins that comprise the catalytic domain of a sialidase but comprise less than the entire sialidase the catalytic domain sequence is derived from are considered sialidase catalytic domain proteins. Sialidase catalytic domain proteins can comprise other protein sequences, such as but not limited to functional domains derived from other proteins. A pharmaceutical composition comprising a sialidase can be formulated for nasal, tracheal, bronchial, oral, or topical administration, or can be formulated as an injectable solution or as eyedrops. A pharmaceutical composition comprising a sialidase can be used to treat or prevent pathogen infection, to treat or prevent allergy or inflammatory response, or to enhance the transduction efficiency of a recombinant virus for gene therapy.

In yet another aspect, the present invention includes a method for treating or preventing infection by a pathogen. In preferred embodiments, the method comprises administering a sialidase activity, such as a sialidase or a sialidase catalytic domain protein, including a sialidase catalytic domain fusion protein, to a subject to prevent or treat an infection. A pathogen can be, for example, a viral or bacterial pathogen. The method includes applying a pharmaceutically effective amount of a compound of the present invention to at least one target cell of a subject. Preferably, the pharmaceutical composition can applied by the use of a spray, inhalant, or topical formulation.

The present invention also provides new compositions and methods for treating allergy and inflammation. In particular, the present invention provides compounds that can act extracellularly to prevent or inhibit adhesion and function of inflammatory cells. Some preferred embodiments of compounds for treating allergy or inflammation comprise at least one therapeutic domain that has the said extracellular activity and an at least one anchoring domain that anchors the compound to the surface of a target cell. In some preferred embodiments, the method comprises administering a siaidase activity, such as a sialidase or a sialidase catalytic domain protein, including a sialidase catalytic domain fusion protein to a subject to prevent or treat an allergic or inflammatory response. The allergic or inflammatory response can be asthma, allergic rhinitis, skin conditions such as eczema, or response to plant or animal toxins. The method includes applying a pharmaceutically effective amount of a compound of the present invention to at least one target cell of a subject. Preferably, the pharmaceutical composition can applied by the use of a spray, inhalant, or topical formulation.

The present invention also provides new compositions and methods for improving efficiency of gene transfer by recombinant viral vectors during gene therapy. In particular, the present invention provides compounds that can act extracellularly to reduce the physical or chemical barrier that hinders transduction by gene therapy vectors, such as AAV vector. Some preferred compounds of the present invention for improving efficiency of gene transfer by recombinant viral vectors comprise at least one therapeutic domain that has an extracellular activity and an at least one anchoring domain that anchors the compound to the surface of a target cell. In some preferred embodiments, the method comprises administering a siaidase activity, such as a sialidase or a sialidase catalytic domain protein, including a sialidase catalytic domain fusion protein to a subject to facilitate transduction of a target cell by a recombinant viral vector. The method includes applying an effective amount of a compound of the present invention along with a recombinant viral vector to at least one target cell. A pharmaceutical composition of the present invention can be applied by the use of a spray, inhalant, or topical formulation.

BRIEF DESCRIPTION OF SEVERAL VIEWS OF THE DRAWINGS

FIG. 1 is a schematic depiction of the primary amino acid structure of aprotinin.

FIG. 2 shows GAG-binding sequences of six human genes: PF4, human platelet factor 4; IL8, human interleukin 8; AT III, human antithrombin III; ApoE, human apolipoprotein E; AAMP, human angio-associated migratory cell protein; AR, human amphiregulin.

FIG. 3 is a sequence comparison between human sialidases NEU2 and NEU4.

FIG. 4 is a table comparing substrate specificity of bacterial and fungal sialidases.

FIG. 5 depicts the nucleotide (SEQ ID NO:28) and amino acid (SEQ ID NO:29) sequences of Construct #1 encoding His6-AvCD. NcoI and HindIII sites used for cloning into pTrc99a are shown in bold.

FIG. 6 depicts the nucleotide (SEQ ID NO:18) and amino acid (SEQ ID NO:19) sequences of Construct #2 encoding AR-AvCD. NcoI and HindIII sites used for cloning into pTrc99a are shown in bold.

FIG. 7 depicts the nucleotide (SEQ ID NO:36) and amino acid (SEQ ID NO:37) sequences of Construct #3 encoding AR-G4S-AvCD. NcoI and HindIII sites used for cloning into pTrc99a are shown in bold.

FIG. 8 is a graph of data from an experiment showing that the AR-tag enhances the removal of α(2,6)-linked sialic acid from MDCK cells. The Y axis shows the percentage of α(2,6)-linked sialic acid remaining on the surface of MDCK cells after treatment with various dilutions of recombinant AvCD (Construct #1) (diamonds) or recombinant AR-AvCD (Construct #2) (squares).

Figure 9:
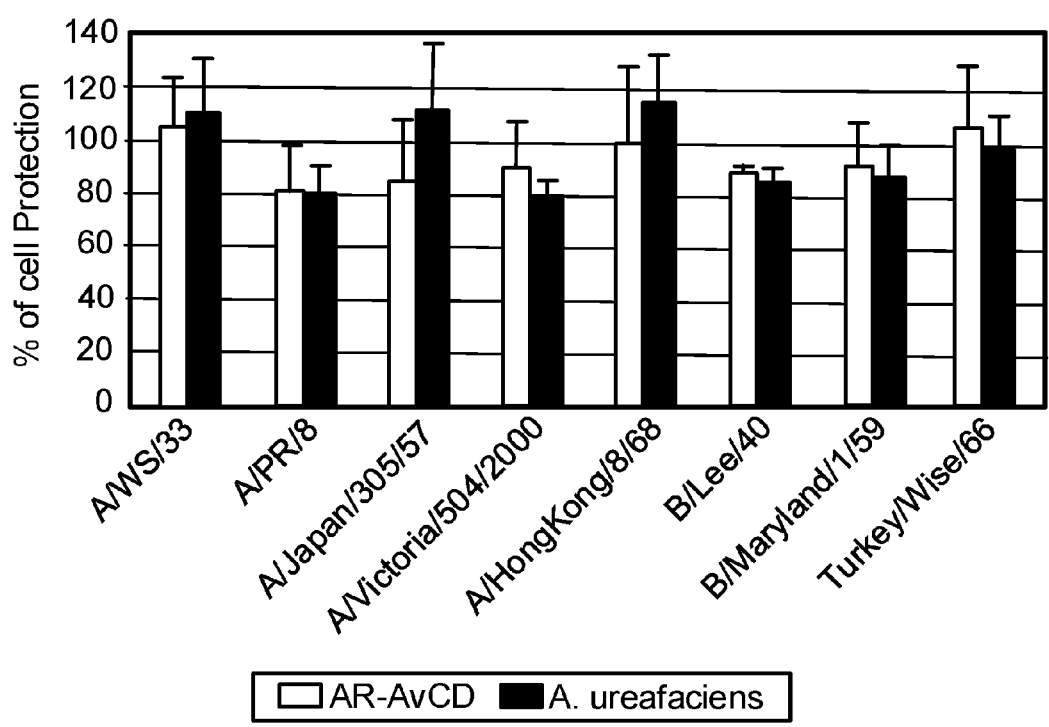
Figure 10:
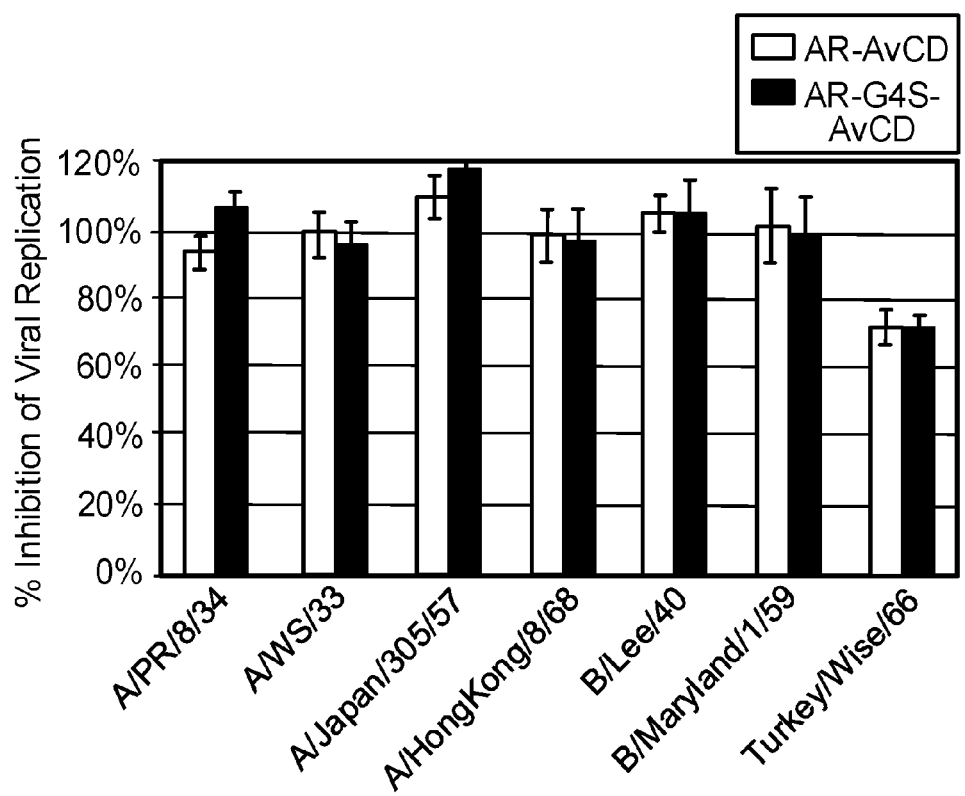

FIG. 9 is a graph depicting the protection against influenza viruses conferred by treating MDCK cells with recombinant AR-AvCD protein made from Construct #2 or the isolated sialidase of *A. ureafaciens*. The challenge viral strains are: A/WS/33 (H1N1); A/PR/8 (H1N1); A/Japan/305/57 (H2N2); A/Victoria/504/2000 (H3N2); A/HongKong/8/68 (H3N2); B/Lee/40; 7. B/Maryland/1/59; and Turkey/Wis/66 (H9N2).

FIG. 10 is a graph showing the level of inhibition of influenza virus amplification by the recombinant AR-AvCD sialidase and the recombinant AR-$G_4$S-AvCD sialidase. The challenge viral strains are: A/PR/8 (H1N1); A/WS/33 (H1N1); A/Japan/305/57 (H2N2); A/HongKong/8/68 (H3N2); B/Lee/40; 7. B/Maryland/1/59; and Turkey/Wis/66 (H9N2).

FIG. 11 provides graphs showing that topical administration of recombinant AR-AvCD sialidase fusion protein reduces the inflammatory responses of ferrets infected with an influenza A (H1N1) virus. (A) The total number of inflammatory cells from nasal wash samples obtained from infected animals at the indicated times after infection. (B) The protein concentration was determined in cell-free nasal wash samples of infected ferrets. Infected ferrets were vehicle-treated (squares) or were treated with recombinant AR-AvCD sialidase fusion protein made from Construct #2 (triangles). Uninfected animals were also treated with recombinant AR-AvCD sialidase fusion protein (diamonds). Statistically significant values are labeled with * ($p<0.05$) and ** ($p<0.01$).

FIG. 12 is a table depicting inhibition of viral replication, cell protection EC50's, and selective indexes for two sialidase catalytic domain fusion proteins of the present invention. All EC50's are in mU/ml.

FIG. 13 is a table depicting viral replication in the respiratory tract of ferrets treated with a sialidase catalytic domain fusion proteins of the present invention and ferrets treated with a control vehicle.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings:

A "pathogen" can be any virus or microorganism that can infect a cell, a tissue or an organism. A pathogen can be a virus, bacterium, or protozoan.

A "target cell" is any cell that can be infected by a pathogen or any cell that can interact with inflammatory cells, or a host cell that is the intended destination for an exogenous gene transferred by a recombinant virus.

A "recombinant virus" or a "recombinant viral vector", a "gene therapy viral vector" or a "gene therapy vector" is defined as a genetically engineered virus that comprises one or more exogenous genes. When a target cell is transduced by a recombinant virus, the exogenous gene(s) is transferred to the target cell. Genes transferred to a target cell can be expressed in the cell to provide the intended therapeutic effects. Currently, most commonly used gene therapy viral vectors are based on four types of viruses: retrovirus (including lentivirus), adenovirus, adeno-associated virus (AAV) and herpes simplex virus type 1.

"Inflammatory cells" are the cells that carry out or participate in inflammatory responses of the immune system. Inflammatory cells include B lymphocytes, T lymphocytes, macrophages, basophils, eosinophils, mast cells, NK cells and monocytes.

An "extracellular activity that can prevent the infection of a target cell by a pathogen" is any activity that can block or impede infection of a target cell by a pathogen by acting at or near the exterior surface of a target cell. An extracellular activity that can prevent the infection of a target cell by a pathogen, can be an activity such as, but not limited to, a catalytic activity or an inhibitory activity. For example, a catalytic activity can be an enzymatic activity that degrades one or more entities (such as but not limited to ligands, receptors, or enzymes) on a pathogen, on a target cell, or in the vicinity of a target cell, in which the one or more entities contribute to the infection process. A catalytic activity can also modify one or more entities on a pathogen, on a target cell, or in the vicinity of a target cell, such that the infection-promoting property of the entity is reduced. An inhibitory activity can be an activity that, for example, binds to a receptor or ligand and prevents the receptor or ligand from binding a moiety, where the binding is necessary for or promotes the infection process. An inhibitory activity can also be an inhibitor of an enzyme or receptor that prevents the enzyme or receptor from performing a function that is necessary for or promotes the infection process. The exterior of a target cell includes the target cell membrane itself, as well as the extracellular milieu surrounding the target cell, including extracellular matrix, intracellular spaces, and luminal spaces. For epithelial cells, the exterior of a target cell also includes the apical or luminal surface of the cell membrane that form luminal linings, and the extracellular milieu near the luminal surface. An "extracellular activity that can prevent the infection of a target cell by a pathogen" can be any type of chemical entity, including a protein, polypeptide, peptide, nucleic acid, peptide nucleic acid, nucleic acid analogue, nucleotide, nucleotide analogue, small organic molecule, polymer, lipids, steroid, fatty acid, carbohydrate, and the like, including combinations of any of these. Preferably, however, the activity comprises a peptide or protein or coupled to a peptide or protein.

An "extracellular activity that can improve transduction efficiency, or gene transfer efficiency, by a recombinant virus" is any activity that reduces or eliminates physical or chemical barriers that impedes host cell entry by a recombinant virus by acting at or near the exterior surface of a target cell. An extracellular activity that can improve transduction efficiency, or gene transfer efficiency, by a recombinant virus can be an activity such as, but not limited to, a catalytic activity or an inhibitory activity. For example, a catalytic activity can be an enzymatic activity that degrades one or more entities (such as but not limited to ligands, receptors, or enzymes) on a pathogen, on a target cell, or in the vicinity of a target cell, in which the one or more entities contribute to the infection process. A catalytic activity can also modify one or more entities on a pathogen, on a target cell, or in the vicinity of a target cell, such that the infection-promoting property of the entity is reduced. An inhibitory activity can be an activity that, for example, binds to a receptor or ligand and prevents the receptor or ligand from binding a moiety, where the binding is necessary for or promotes the infection process. An inhibitory activity can also be an inhibitor of an enzyme or receptor that prevents the enzyme or receptor from performing a function that is necessary for or promotes the infection process. The exterior of a target cell includes the target cell membrane itself, as well as the extracellular milieu surrounding the target cell, including extracellular matrix, intracellular spaces, and luminal spaces. For epithelial cells, the exterior of a target cell also includes the apical or luminal surface of the cell membrane that form luminal linings, and the extracellular milieu near the luminal surface. An "extracellular activity that can prevent the infection of a target cell by a pathogen" can be any type of chemical entity, including a protein, polypeptide, peptide, nucleic acid, peptide nucleic acid, nucleic acid analogue, nucleotide, nucleotide analogue, small organic molecule, polymer, lipids, steroid, fatty acid, carbohydrate, and the like, including combinations of any of these. Preferably, however, the activity comprises a peptide or protein or coupled to a peptide or protein.

An "extracellular activity that can inhibit adhesion or function of inflammatory cells" is any activity that can prevent inflammatory cells from contacting the target cell and affecting the normal physiological status of the target cell.

A "domain that can anchor said at least one therapeutic domain to the membrane of a target cell", also called an "extracellular anchoring domain" or simply, "anchoring domain" refers to a chemical entity can that can stably bind a moiety that is at or on the exterior of a cell surface or is in close proximity to the surface of a cell. An extracellular anchoring domain can be reversibly or irreversibly linked to one or more moieties, such as, preferably, one or more therapeutic domains, and thereby cause the one or more attached therapeutic moieties to be retained at or in close proximity to the exterior surface of a eukaryotic cell. Preferably, an extracellular anchoring domain binds at least one molecule on the surface of a target cell or at least one molecule found in close association with the surface of a target cell. For example, an extracellular anchoring domain can bind a molecule covalently or noncovalently associated with the cell membrane of a target cell, or can bind a molecule present in the extracellular matrix surrounding a target cell. An extracellular anchoring domain preferably is a peptide, polypeptide, or protein, and can also comprise any additional type of chemical entity, including one or more additional proteins, polypeptides, or peptides, a nucleic acid, peptide nucleic acid, nucleic acid analogue, nucleotide, nucleotide analogue, small organic molecule, polymer, lipids, steroid, fatty acid, carbohydrate, or a combination of any of these.

As used herein, a protein or peptide sequences is "substantially homologous" to a reference sequence when it is either identical to a reference sequence, or comprises one or more amino acid deletions, one or more additional amino acids, or more one or more conservative amino acid substitutions, and retains the same or essentially the same activity as the reference sequence. Conservative substitutions may be defined as exchanges within one of the following five groups:
  I. Small, aliphatic, nonpolar or slightly polar residues: Ala, Ser, Thr, Pro, Gly
  II. Polar, negatively charged residues and their amides: Asp, Asn, Glu, Gln
  III. Polar, positively charged residues: His, Arg, Lys
  IV. Large, aliphatic nonpolar residues: Met, Leu, Ile, Val, Cys
  V. Large aromatic residues: Phe, Try, Trp Within the foregoing groups, the following substitution are considered to be "highly conservative": Asp/Glu, His/Arg/Lys, Phe/Tyr/Trp, and Met/Leu/Ile/Val. Semi-conservative substitutions are defined to be exchanges between two of groups (I)-(IV) above which are limited to supergroup (A), comprising (I), (II), and (III) above, or to supergroup (B), comprising (IV) and (V) above. In addition, where hydrophobic amino acids are specified in the application, they refer to the amino acids Ala, Gly, Pro, Met, Leu, Ile, Val, Cys, Phe, and Trp, whereas hydrophilic amino acids refer to Ser, Thr, Asp, Asn, Glu, Gln, His, Arg, Lys, and Tyr.

A "sialidase" is an enzyme that can remove a sialic acid residue from a substrate molecule. The sialidases (N-acyl-neuraminosylglycohydrolases, EC 3.2.1.18) are a group of enzymes that hydrolytically remove sialic acid residues from sialo-glycoconjugates. Sialic acids are alpha-keto acids with 9-carbon backbones that are usually found at the outermost positions of the oligosaccharide chains that are attached to glycoproteins and glycolipids. One of the major types of sialic acids is N-acetylneuraminic acid (Neu5Ac), which is the biosynthetic precursor for most of the other types. The substrate molecule can be, as nonlimiting examples, an oligosaccharide, a polysaccharide, a glycoprotein, a ganglioside, or a synthetic molecule. For example, a sialidase can cleave bonds having alpha(2,3)-Gal, alpha(2,6)-Gal, or alpha(2,8)-Gal linkages between a sialic acid residue and the remainder of a substrate molecule. A sialidase can also cleave any or all of the linkages between the sialic acid residue and the remainder of the substrate molecule. Two major linkages between Neu5Ac and the penultimate galactose residues of carbohydrate side chains are found in nature, Neu5Ac alpha (2,3)-Gal and Neu5Ac alpha (2,6)-Gal. Both Neu5Ac alpha (2,3)-Gal and Neu5Ac alpha (2,6)-Gal molecules can be recognized by influenza viruses as the receptor, although human viruses seem to prefer Neu5Ac alpha (2,6)-Gal, avian and equine viruses predominantly recognize Neu5Ac alpha (2,3)-Gal. A sialidase can be a naturally-occurring sialidase, an engineered sialidase (such as, but not limited to a sialidase whose amino acid sequence is based on the sequence of a naturally-occurring sialidase, including a sequence that is substantially homologous to the sequence of a naturally-occurring sialidase). As used herein, "sialidase" can also mean the active portion of a naturally-occurring sialidase, or a peptide or protein that comprises sequences based on the active portion of a naturally-occurring sialidase.

A "fusion protein" is a protein comprising amino acid sequences from at least two different sources. A fusion protein can comprise amino acid sequence that is derived from a naturally occurring protein or is substantially homologous to all or a portion of a naturally occurring protein, and in addition can comprise from one to a very large number of amino acids that are derived from or substantially homologous to all or a portion of a different naturally occurring protein. In the alternative, a fusion protein can comprise amino acid sequence that is derived from a naturally occurring protein or is substantially homologous to all or a portion of a naturally occurring protein, and in addition can comprise from one to a very large number of am A "sialidase catalytic domain protein" is a protein that comprises the catalytic domain of a sialidase, or an amino acid sequence that is substantially homologous to the catalytic domain of a sialidase, but does not comprises the entire amino acid sequence of the sialidase the catalytic domain is derived from, wherein the sialidase catalytic domain protein retains substantially the same activity as the intact sialidase the catalytic domain is derived from. A sialidase catalytic domain protein can comprise amino acid sequences that are not derived from a sialidase, but this is not required. A sialidase catalytic domain protein can comprise amino acid sequences that are derived from or substantially homologous to amino acid sequences of one or more other known proteins, or can comprise one or more amino acids that are not derived from or substantially homologous to amino acid sequences of other known proteins.

I. Composition for Preventing or Treating Infection by a Pathogen

The present invention includes peptide or protein-based compounds that comprise at least one domain that can anchor at least one therapeutic domain to the membrane of a eukaryotic cell and at least one therapeutic domain having an extracellular activity that can prevent the infection of a cell by a pathogen. By "peptide or protein-based" compounds, it is meant that the two major domains of the compound have an amino acid framework, in which the amino acids are joined by peptide bonds. A peptide or protein-based compound can also have other chemical compounds or groups attached to the amino acid framework or backbone, including moieties that contribute to the anchoring activity of the anchoring domain, or moieties that contribute to the infection-preventing activity or the therapeutic domain. For example, the protein-based therapeutics of the present invention can comprise compounds and molecules such as but not limited to: carbohydrates, fatty acids, lipids, steroids, nucleotides, nucleotide analogues, nucleic acid molecules, nucleic acid analogues, peptide nucleic acid molecules, small organic molecules, or even polymers. The protein-based therapeutics of the present invention can also comprise modified or non-naturally occurring amino acids. Non-amino acid portions of the compounds can serve any purpose, including but not limited to: facilitating the purification of the compound, improving the solubility or distribution or the compound (such as in a therapeutic formulation), linking domains of the compound or linking chemical moieties to the compound, contributing to the two-dimensional or three-dimensional structure of the compound, increasing the overall size of the compound, increasing the stability of the compound, and contributing to the anchoring activity or therapeutic activity of the compound.

The peptide or protein-based compounds of the present invention can also include protein or peptide sequences in addition to those that comprise anchoring domains or therapeutic domains. The additional protein sequences can serve any purpose, including but not limited to any of the purposes outlined above (facilitating the purification of the compound, improving the solubility or distribution or the compound, linking domains of the compound or linking chemical moieties to the compound, contributing to the two-dimensional or three-dimensional structure of the compound, increasing the overall size of the compound, increasing the stability of the compound, or contributing to the anchoring activity or therapeutic activity of the compound). Preferably any additional protein or amino acid sequences are part of a single polypeptide or protein chain that includes the anchoring domain or domains and therapeutic domain or domains, but any feasible arrangement of protein sequences is within the scope of the present invention.

The anchoring domain and therapeutic domain can be arranged in any appropriate way that allows the compound to bind at or near a target cell membrane such that the therapeutic domain can exhibit an extracellular activity that prevents or impedes infection of the target cell by a pathogen. The compound will preferably have at least one protein or peptide-based anchoring domain and at least one peptide or protein-based therapeutic domain. In this case, the domains can be arranged linearly along the peptide backbone in any order. The anchoring domain can be N-terminal to the therapeutic domain, or can be C-terminal to the therapeutic domain. It is also possible to have one or more therapeutic domains flanked by at least one anchoring domain on each end. Alternatively, one or more anchoring domains can be flanked by at least one therapeutic domain on each end. Chemical, or preferably, peptide, linkers can optionally be used to join some or all of the domains of a compound.

It is also possible to have the domains in a nonlinear, branched arrangement. For example, the therapeutic domain can be attached to a derivatized side chain of an amino acid that is part of a polypeptide chain that also includes, or is linked to, the anchoring domain.

A compound of the present invention can have more than one anchoring domain. In cases in which a compound has more than one anchoring domain, the anchoring domains can be the same or different. A compound of the present invention can have more than one therapeutic domain. In cases in which a compound has more than one therapeutic domain, the therapeutic domains can be the same or different. Where a compound comprises multiple anchoring domains, the anchoring domains can be arranged in tandem (with or without linkers) or on alternate sides of other domains, such as therapeutic domains. Where a compound comprises multiple therapeutic domains, the therapeutic domains can be arranged in tandem (with or without linkers) or on alternate sides of other domains, such as, but not limited to, anchoring domains.

A peptide or protein-based compound of the present invention can be made by any appropriate way, including purifying naturally occurring proteins, optionally proteolytically cleaving the proteins to obtain the desired functional domains, and conjugating the functional domains to other functional domains. Peptides can also be chemically synthesized, and optionally chemically conjugated to other peptides or chemical moieties. Preferably, however, a peptide or protein-based compound of the present invention is made by engineering a nucleic acid construct to encode at least one anchoring domain and at least one therapeutic domain together (with or without nucleic acid linkers) in a continuous polypeptide. The nucleic acid constructs, preferably having appropriate expression sequences, can be transfected into prokaryotic or eukaryotic cells, and the therapeutic protein-based compound can be expressed by the cells and purified. Any desired chemical moieties can optionally be conjugated to the peptide or protein-based compound after purification. In some cases, cell lines can be chosen for expressing the protein-based therapeutic for their ability to perform desirable post-translational modifications (such as, but not limited to glycosylation).

A great variety of constructs can be designed and their protein products tested for desirable activities (such as, for example, binding activity of an anchoring domain, or a binding, catalytic, or inhibitory activity of a therapeutic domain). The protein products of nucleic acid constructs can also be tested for their efficacy in preventing or impeding infection of a target cell by a pathogen. In vitro and in vivo tests for the infectivity of pathogens are known in the art, such as those described in the Examples for the infectivity of influenza virus.

Anchoring Domain

As used herein, an "extracellular anchoring domain" or "anchoring domain" is any moiety that can stably bind an entity that is at or on the exterior surface of a target cell or is in close proximity to the exterior surface of a target cell. An anchoring domain serves to retain a compound of the present invention at or near the external surface of a target cell.

An extracellular anchoring domain preferably binds 1) a molecule expressed on the surface of a target cell, or a moiety, domain, or epitope of a molecule expressed on the surface of a target cell, 2) a chemical entity attached to a molecule expressed on the surface of a target cell, or 3) a molecule of the extracellular matrix surrounding a target cell.

An anchoring domain is preferably a peptide or protein domain (including a modified or derivatized peptide or protein domain), or comprises a moiety coupled to a peptide or protein. A moiety coupled to a peptide or protein can be any type of molecule that can contribute to the binding of the anchoring domain to an entity at or near the target cell surface, and is preferably an organic molecule, such as, for example, nucleic acid, peptide nucleic acid, nucleic acid analogue, nucleotide, nucleotide analogue, small organic molecule, polymer, lipids, steroid, fatty acid, carbohydrate, or any combination of any of these.

A molecule, complex, domain, or epitope that is bound by an anchoring domain may or may not be specific for the target cell. For example, an anchoring domain may bind an epitope present on molecules on or in close proximity to the target cell and that occur at sites other than the vicinity of the target cell as well. In many cases, however, localized delivery of a therapeutic compound of the present invention will restrict its occurrence primarily to the surface of target cells. In other cases, a molecule, complex, moiety, domain, or epitope bound by an anchoring domain may be specific to a target tissue or target cell type.

Target tissue or target cell type includes the sites in an animal or human body where a pathogen invades or amplifies. For example, a target cell can be an endothelial cell that can be infected by a pathogen. A composition of the present invention can comprise an anchoring domain that can bind a cell surface epitope, for example, that is specific for the endothelial cell type. In another example, a target cell can be an epithelial cell and a composition of the present invention can bind an epitope present on the cell surface of many epithelial cell types, or present in the extracellular matrix of different types of epithelial cells. In this case localized delivery of the composition can restrict its localization to the site of the epithelial cells that are targets of the pathogen.

A compound for preventing or treating infection by a pathogen can comprise an anchoring domain that can bind at or near the surface of epithelial cells. For example, heparan sulfate, closely related to heparin, is a type of glycosaminoglycan (GAG) that is ubiquitously present on cell membranes, including the surface of respiratory epithelium. Many proteins specifically bind to heparin/heparan sulfate, and the GAG-binding sequences in these proteins have been identified (Meyer, F A, King, M and Gelman, R A. (1975) *Biochimica et Biophysica Acta* 392: 223-232; Schauer, S. ed., pp 233. Sialic Acids Chemistry, Metabolism and Function. Springer-Verlag, 1982). For example, the GAG-binding sequences of human platelet factor 4 (PF4) (SEQ ID NO:2), human interleukin 8 (IL8) (SEQ ID NO:3), human antithrombin III (AT III) (SEQ ID NO:4), human apoprotein E (ApoE) (SEQ ID NO:5), human angio-associated migratory cell protein (AAMP) (SEQ ID NO:6), or human amphiregulin (SEQ ID NO:7) (FIG. 2) have been shown to have very high affinity (in the nanomolar range) towards heparin (Lee, M K and Lander, A D. (1991) Pro Natl Acad Sci USA 88:2768-2772; Goger, B, Halden, Y, Rek, A, Mosl, R, Pye, D. Gallagher, J and Kungl, A J. (2002) Biochem. 41:1640-1646; Witt, D P and Lander A D (1994) Curr Bio 4:394-400; Weisgraber, K H, Rall, S C, Mahley, R W, Milne, R W and Marcel, Y. (1986) J Bio Chem 261:2068-2076). The GAG-binding sequences of these proteins are distinct from their receptor-binding sequences, so they will not induce the biological activities associated with the full-length proteins or the receptor-binding domains. These sequences, or other sequences that have been identified or are identified in the future as heparin/heparan sulfate binding sequences, or sequences substantially homologous to identified heparin/heparan sulfate binding sequences that have heparin/heparan sulfate binding activity, can be used as epithelium-anchoring-domains in compounds of the present invention that can be used to prevent or treat, for example, respiratory epithelium-infecting viruses such as, but not limited to, influenza virus.

An anchoring domain can bind a moiety that is specific to the target cell type of a particular species or can bind a moiety that is found in the target cell type of more than one species. In cases where the anchoring domain can bind moieties that are present at the surface of target cells of more than one species, and a virus or pathogen can infect more than one species, a therapeutic compound can have utility for more than one species (providing that the therapeutic domain is also effective across the relevant species.) For example, in the case of therapeutic compounds that can be used against influenza virus, a therapeutic compound of the present invention that has an anchoring domain that binds heparin/heparan sulfate, the compound can be used in mammals (including humans) as well as avians.

Therapeutic Domain

A compound of the present invention includes at least one therapeutic domain that has an extracellular activity that can prevent or impede the infection of a cell by a pathogen, can modulate the immune response of a subject, or can improve transduction efficiency of a recombinant virus. The therapeutic activity can be, as nonlimiting examples, a binding activity, a catalytic activity, or an inhibitory activity. In some embodiments of the present invention, the therapeutic activity acts to modify or inhibit a function of the pathogen that contributes to infectivity of the cell by the pathogen. In other embodiments, a therapeutic domain can modify or inhibit a function of the target cell or target organism.

For example, the therapeutic domain can bind a receptor on a target cell that is necessary for binding of the pathogen to a target cell. In this way the therapeutic moiety can block binding of the pathogen to a target cell and prevent infection. In an alternative, a therapeutic domain can bind a molecule or epitope on a pathogen to prevent an interaction of the molecule or epitope with a target cell that is necessary for infection. A therapeutic domain can also have a catalytic activity that can degrade a molecule or epitope of the pathogen or host that allows for or promotes infection of a target cell by a host. In yet other embodiments, a therapeutic domain can be an inhibitor of an activity that is necessary for target cell infection by a pathogen. The inhibited activity can be an activity of the host organism or of the pathogen.

The therapeutic domain preferably acts extracellularly, meaning that its infection-preventing, inflammatory response-modulating, or transduction-enhancing activity takes place at the target cell surface or in the immediate area surrounding the target cell, including sites within the extracellular matrix, intracellular spaces, or luminal spaces of tissues.

A therapeutic domain is preferably a peptide or protein domain (including a modified or derivatized peptide or protein domain), or comprises a moiety coupled to a peptide or protein. A moiety coupled to a peptide or protein can be any type of molecule that can prevent or impede the infection of a target cell by a pathogen, and is preferably an organic molecule, such as, for example, nucleic acid, peptide nucleic acid, nucleic acid analogue, nucleotide, nucleotide analogue, small organic molecule, polymer, lipids, steroid, fatty acid, carbohydrate, or any combination of any of these.

A therapeutic domain can be a synthetic peptide or polypeptide, or can comprise a synthetic molecule that can be conjugated to a peptide or polypeptide, can be a naturally-occurring peptide or protein, or a domain of naturally-occurring protein. A therapeutic domain can also be a peptide or protein that is substantially homologous to a naturally-occurring peptide or protein.

A therapeutic domain can have utility in a particular species, or can prevent or impede pathogen infection in more than one species. For example, therapeutic domains that inhibit pathogen functions can in general be used in a range of species that can be infected by the host, while therapeutic domains that interrupt host-pathogen interactions by interfering with a property of the host may or may not be species-specific. In many cases, anchoring domains and therapeutic domains can be effective in more than one species, so that compounds of the present invention can be used to advance human and animal health, while reducing propagation and spread of the virus through animal hosts. For example, when the therapeutic domain is a sialidase, a sialidase that can cleave more than one type of linkage between a sialic acid residue and the remainder of a substrate molecule, in particular, a sialidase that can cleave both alpha(2, 6)-Gal and alpha (2, 3)-Gal linkages, can protect humans from infections by a broad-spectrum of influenza viruses, including viruses that are naturally hosted in different species such as birds, pigs or horses.

Linkers

A compound of the present invention can optionally include one or more linkers that can join domains of the compound. Linkers can be used to provide optimal spacing or folding of the domains of a compound. The domains of a compound joined by linkers can be therapeutic domains, anchoring domains, or any other domains or moieties of the compound that provide additional functions such as enhancing compound stability, facilitating purification, etc. A linker used to join domains of compounds of the present invention can be a chemical linker or an amino acid or peptide linker. Where a compound comprises more than one linker, the linkers can be the same or different. Where a compound comprises more than one linker, the linkers can be of the same or different lengths.

Many chemical linkers of various compositions, polarity, reactivity, length, flexibility, and cleavability are known in the art of organic chemistry. Preferred linkers of the present invention include amino acid or peptide linkers. Peptide linkers are well known in the art. Preferably linkers are between one and one hundred amino acids in length, and more preferably between one and thirty amino acids in length, although length is not a limitation in the linkers of the compounds of the present invention. Preferably linkers comprise amino acid sequences that do not interfere with the conformation and activity of peptides or proteins encoded by monomers of the present invention. Some preferred linkers of the present invention are those that include the amino acid glycine. For example, linkers having the sequence: (GGGGS (SEQ ID NO:10))n, where n is a whole number between 1 and 20, or more preferably between 1 and 12, can be used to link domains of therapeutic compounds of the present invention.

The present invention also comprises nucleic acid molecules that encode protein-based compounds of the present invention that comprise at least one therapeutic domain and at least one anchoring domain. The nucleic acid molecules can have codons optimized for expression in particular cell types, such as, for example *E. coli* or human cells. The nucleic acid molecules or the present invention that encode protein-based compounds of the present invention that comprise at least one therapeutic domain and at least one anchoring domain can also comprise other nucleic acid sequences, including but not limited to sequences that enhance gene expression. The nucleic acid molecules can be in vectors, such as but not limited to expression vectors.

Composition Comprising at Least One Anchoring Domain and at Least One Protease Inhibitor In some aspects of the present invention, a therapeutic domain that has an extracellular activity that can prevent the infection of a cell by a pathogen is a protease inhibitor. The protease inhibitor can be any type of chemical entity, such as, for example, a carbohydrate or polymer, but is preferably a protein or peptide that inhibits the activity of an enzyme. Preferably, the protease inhibitor inhibits the activity of an enzyme that at least partially processes at least one pathogen or host cell protein, where the processing of the pathogen or host cell protein is necessary for pathogen infectivity. The enzyme that can process a viral protein necessary for pathogen infectivity can be a pathogen enzyme, or an enzyme that originates from the host organism. Preferably, the processing enzyme acts at or near the target cell surface, so that a compound of the present invention that is anchored at or near the surface of a target cell can effectively inhibit the activity of the enzyme.

Compounds of the present invention that comprise protease inhibitory domains can be used to inhibit infection by any pathogen that requires a protease in its life cycle, in which the protease is active at or near the surface of the host cell. These protein-based compositions can have, for example, one of the following structures:

(Anchoring Domain)n-linker-(Protease Inhibitor)n (n=1, 2, 3 or more)

or:

(Protease Inhibitor)n-linker-(Anchoring Domain)n (n=1, 2, 3 or more)

The protease inhibitor can be a monomeric form of a peptide or polypeptide or can be multiple copies of the same polypeptide that are either linked directly or with spacing sequence in between. Alternatively, different polypeptide-based protease inhibitors can be linked with each other, such as, for example, aprotinin linked with soybean protease inhibitor as protease inhibiting functional domains. The polypeptides or peptides can be linked directly or via a spacer composed of peptide linker sequence. The anchoring domain can be any peptide or polypeptide that can bind at or near the surface of target cells.

The protease inhibitor can be a naturally occurring protease inhibitor (or an active portion thereof) or can be an engineered protease inhibitor. A peptide protease inhibitor used in a compound of the present invention can have a sequence substantially homologous to a naturally occurring protease inhibitor, having one or more deletions, additions, or substitutions while retaining the activity, or substantially retaining the same activity, of the naturally occurring protease inhibitor.

In one preferred embodiment of the present invention, a therapeutic compound of the present invention is for the prevention and treatment of influenza in humans, and the therapeutic domain is a protein or peptide protease inhibitor that can inhibit a serine protease that can cleave the influenza virus hemagglutinin precursor protein HA0 into HA1 and HA2.

A number of serine protease inhibitors have been shown to reduce HA cleavage and influenza virus activation in cultured cells, in chicken embryos and in lungs of infected mice. They include many of the commonly used trypsin inhibitors, such as: aprotinin (Zhirnov O P, Ikizler M R and Wright P F. (2002) *J Virol* 76:8682-8689), leupeptin (Zhirnov O P, Ikizler M R and Wright P F. (2002) *J Virol* 76:8682-8689; Tashiro M, Klenk H D and Rott R. (1987) *J Gen Virol* 68:2039-2043), soybean protease inhibitor (Barbey-Morel C L, Oeltmann T N, Edwards K M and Wright P F. (1987) *J Infect Dis* 155:667-672), e-aminocaproic acid (Zhirnov O P, Ovchartenko A V and Bukrinskaya A G. 1982. *Arch Virol* 73:263-272) and n-p-tosyl-L-lysine chloromethylketone (TLCK) (Barbey-Morel C L, Oeltmann T N, Edwards K M and Wright P F. (1987) *J Infect Dis* 155:667-672). Among these, aerosol inhalation of aprotinin has shown definitive therapeutic effects against influenza and parainfluenza bronchopneumonia in mice (Zhirnov O P, Ovcharenko A V and Bukrinskaya A G. (1984) *J Gen Virol* 65:191-196; Zhirnov O P, Ovcharenko A V and Bukrinskaya A G. (1985) *J Gen Virol* 66:1633-1638; Zhirnov O P. (1987) *J Med Virol* 21:161-167; Ovcharenko A V and Zhirnov O P. (1994) *Antiviral Res* 23:107-118) as well as in human (Zhirnov O P. (1983) *Problems Virol*. 4:9-12 (in Russian)).

Aprotinin (SEQ ID NO: 1; FIG. 1) is a 58 amino acid polypeptide inhibitor (also called Trasylol or bovine pancreatic trypsin inhibitor (BPTI)). A compound of the present invention can have one or more aprotinin domains; for example, a therapeutic composition of the present invention can have from one to six aprotinin polypeptides, more preferably from one to three aprotinin polypeptides. A compound of the present invention can also have a therapeutic domain comprising a polypeptide or peptide having substantial homology to the amino acid sequence of aprotinin.

A compound for preventing or treating influenza that comprises a protease inhibitor preferably comprises an anchoring domain that can bind at or near the surface of epithelial cells. In some preferred embodiments, the epithelium anchoring domain is a GAG-binding sequence from a human protein, such as, for example, the GAG-binding sequence of human platelet factor 4 (PF4) (SEQ ID NO:2), human interleukin 8 (IL8) (SEQ ID NO:3), human antithrombin III (AT III) (SEQ ID NO:4), human apoprotein E (ApoE) (SEQ ID NO:5), human angio-associated migratory cell protein (AAMP) (SEQ ID NO:6), or human amphiregulin (SEQ ID NO:7) (FIG. 2). A compound of the present invention can also have an anchoring domain comprising a polypeptide or peptide having substantial homology to the amino acid sequences of the GAG-binding domains listed in SEQ ID NO:2, SEQ ID NO:3, SEQ ID NO:4, SEQ ID NO:5, SEQ ID NO:6, and SEQ ID NO:7.

Clinically, a drug comprising aprotinin and an epithelial anchoring domain can be administered by aerosol inhalation to cover the entire respiratory tract to prevent and treat bronchopneumonia caused by influenza viruses, or any other virus, such as parainfluenza virus, that requires serine proteases in its life cycle. Alternatively, an aprotinin/epithelial anchoring domain fusion protein can be administered as nasal spray to treat uncomplicated early stage influenza cases or other infections by respiratory viruses. In addition, an aprotinin/epithelial anchoring domain fusion protein can be used as a prophylaxis for influenza or other viral infections before an infection occurs.

Composition Comprising at Least One Anchoring Domain and at Least One Catalytic Activity In some aspects of the present invention, a therapeutic domain that has an extracellular activity that can prevent the infection of a cell by a pathogen is a catalytic activity. The enzymatic activity can be a catalytic activity that removes, degrades or modifies a host molecule or complex or a pathogen molecule or complex that contributes to the infectivity of the pathogen. Preferably the host molecule or complex or pathogen molecule or complex that is removed, degraded, or modified by the enzymatic activity of a compound of the present invention is on, at, or near the surface of a target cell, so that a compound of the present invention that is anchored to the surface of a target cell can effectively inhibit the host or pathogen molecule or complex.

For example, a therapeutic domain can have a catalytic activity that can digest a molecule or epitope of the pathogen or target cell that is required for host-pathogen binding, and subsequent entry of the pathogen into the target cell. Receptors on target cells that allow for the entry of viruses into cells can be the target of an enzymatic activity of a compound of the present invention.

Compounds of the present invention that comprise catalytic domains can be used to inhibit infection by any pathogen that uses a receptor to gain entry to a target cell, as long as removal of the receptor does not impair the organism. These protein-based compositions can have, for example, one of the following structures:

(Anchoring Domain)n-[linker]-(Enzymatic Activity)n (n=1, 2, 3 or more)

or:

(Enzymatic Activity)n (n=1, 2, 3 or more)-[linker]-(Anchoring Domain)n, where the linkers are optional.

The enzymatic activity can be a monomeric form of a peptide or polypeptide or can be multiple copies of the same polypeptide that are either linked directly or with spacing sequence in between. The polypeptides or peptides can be linked directly or via a spacer composed of peptide linker sequence. The anchoring domain can be any peptide or polypeptide that can bind to or near the surface of target cells.

In one preferred embodiment of the present invention, a therapeutic domain comprises a sialidase that can eliminate or greatly reduce the level of sialic acid on the surface of epithelial cells. Sialic acid is a receptor for influenza viruses. Thus, treating the surface of respiratory epithelial cells with a sialidase can prevent influenza infections or interrupt early infections. The therapeutic domain can comprise a complete sialidase protein, or an active portion thereof. Sialic acid is a receptor for influenza viruses, and at least one of the receptors for parainfluenza virus, some coronavirus and rotavirus, *Streptococcus pneumoniae*, *Mycoplasma pneumoniae*, *Haemophilus influenzae*, *Moraxella catarrhalis*,

*Pseudomonas aeruginosa*, and *Helicobacter pylori*. Thus, treating the surface of respiratory epithelial cells with a sialidase can prevent influenza or other viral infections or interrupt early infections, as well as prevent or reduce colonization of bacteria such as *Streptococcus pneumoniae, Mycoplasma pneumoniae, Haemophilus influenzae, Moraxella catarrhalis*, and *Pseudomonas aeruginosa*. Treating the gastrointestinal epithelial cells with a sialidase can prevent or reduce colonization of *Helicobacter pylori* in the stomach.

Sialic acid also mediates cell adhesion and interactions between inflammatory cells and target cells. Therefore, treating the surface of respiratory epithelial cells with a sialidase can prevent the recruitment of inflammatory cells to the airway surface, and therefore can treat allergic reactions including asthma and allergic rhinitis.

Since sialic acid serves as a barrier that hinder cell entry by a gene therapy vector, treating the target cells with a sialidase can increase transduction efficiency, and therefore improve efficacy of the gene therapy.

Preferred sialidases are the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Actinomyces viscosus, Arthrobacter ureafaciens*, or *Micromonospora viridifaciens* (Genbank Accession Number D01045) can be used. Therapeutic domains of compounds of the present invention can comprise all or a portion of the amino acid sequence of a large bacterial sialidase or can comprise amino acid sequences that are substantially homologous to all or a portion of the amino acid sequence of a large bacterial sialidase. In one preferred embodiment, a therapeutic domain comprises a sialidase encoded by *Actinomyces viscosus*, such as that of SEQ ID NO:12, or such as sialidase sequence substantially homologous to SEQ ID NO:12. In yet another preferred embodiment, a therapeutic domain comprises the catalytic domain of the *Actinomyces viscosus* sialidase extending from amino acids 274-666 of SEQ ID NO:12, or a substantially homologous sequence.

Other preferred sialidases are the human sialidases such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti, E, Preti, A, Venerando, B and Borsani, G. (2002) *Neurochem Res* 27:646-663) (FIG. 3). Therapeutic domains of compounds of the present invention can comprise all or a portion of the amino acid sequences of a human sialidase or can comprise amino acid sequences that are substantially homologous to all or a portion of the amino acid sequences of a human sialidase. Preferably, where a therapeutic domain comprises a portion of the amino acid sequences of a naturally occurring sialidase, or sequences substantially homologous to a portion of the amino acid sequences of a naturally occurring sialidase, the portion comprises essentially the same activity as the human sialidase.

A compound for preventing or treating influenza that comprises an enzymatic domain preferably comprises an anchoring domain that can bind at or near the surface of epithelial cells. In some preferred embodiments, the epithelium-anchoring domain is a GAG-binding sequence from a human protein, such as, for example, the GAG-binding amino acid sequences of human platelet factor 4 (PF4) (SEQ ID NO:2), human interleukin 8 (IL8) (SEQ ID NO:3), human antithrombin III (AT III) (SEQ ID NO:4), human apoprotein E (ApoE) (SEQ ID NO:5), human angio-associated migratory cell protein (AAMP) (SEQ ID NO:6), and human amphiregulin (SEQ ID NO:7) (FIG. 2). An epithelial anchoring domain can also be substantially homologous to a naturally occurring GAG-binding sequence, such as those listed in FIG. 2.

It is also within the scope of the present invention to use compounds comprising a human sialidase, or comprising a sialidase with substantial homology to a sialidase, in the absence of an anchoring domain, in the treatment or prevention of pathogen infections, such as but not limited to influenza, paramyxovirus, coronavirus, rotavirus, and *Pseudomonas aeruginosa* infections or bacterial infections; in the treatment or prevention of allergic and inflammatory responses, and to improve the transduction efficiency of a recombinant virus.

The present invention recognizes that such infections may be prevented or abated by the use of sialidases, such as, but not limited to, the *A. viscosus* sialidase or human sialidases such as NEU2 and NEU4. The sialidases can optionally be adapted, by genetic or chemical engineering, or by pharmaceutical formulation, to improve their half life or retention at the respiratory epithelium.

Because influenza viruses primarily infect the upper respiratory tract, removing the receptor sialic acid locally in the nasal cavity and nasopharynx area can prevent infections or interrupt early infections. The sialidase can be delivered to the upper respiratory tract as a nasal spray, and it can be used either in therapeutic mode during early stage of influenza (or other infection) or in prophylactic mode before the infection occurs. Alternatively, it can be delivered to the lower respiratory tract as an inhalant to treat influenza and to prevent influenza complications, such as bronchopneumonia.

II. Therapeutic Composition Comprising at Least One Sialidase Activity

The present invention includes a therapeutic composition that comprises at least one sialidase activity. The sialidase activity can be a sialidase isolated from any source, such as, for example, a bacterial or mammalian source, or can be a recombinant protein that is substantially homologous to at least a portion of a naturally occurring sialidase. Preferred sialidases are the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Actinomyces viscosus* (Genbank Accession Number L06898), *Arthrobacter ureafaciens*, or *Micromonospora viridifaciens* (Genbank Accession Number D01045) or substantially homologous proteins can be used.

For example, therapeutic compounds of the present invention can comprise a large bacterial sialidase or can comprise a protein with the amino acid sequence of a large bacterial sialidase or can comprise amino acid sequences that are substantially homologous to the amino acid sequence of a large bacterial sialidase. A preferred pharmaceutical composition of the present invention comprises the *A. viscosus* sialidase (SEQ ID NO:12), or comprises a protein substantially homologous to the *A. viscosus* sialidase.

Other preferred sialidases are the human sialidases such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti, E, Preti, A, Venerando, B and Borsani, G. (2002) *Neurochem Res* 27:646-663) (FIG. 3). Therapeutic domains of compounds of the present invention can comprise a human sialidase protein that is substantially homologous to the amino acid sequences of a human sialidase or can comprise amino acid sequences that are substantially homologous to all or a portion of the amino acid sequences of a human sialidase. Preferably, where a therapeutic domain comprises a portion of the amino acid sequences of a naturally occurring sialidase, or sequences substantially homologous to a portion of the amino acid sequences of a naturally occurring sialidase, the portion comprises essentially the same activity as the human sialidase.

A pharmaceutical composition comprising a sialidase can include other compounds, including but not limited to other proteins, that can also have therapeutic activity. A pharmaceutical composition comprising a sialidase can include other compounds that can enhance the stability, solubility, packaging, delivery, consistency, taste, or fragrance of the composition.

A pharmaceutical composition comprising a sialidase can be formulated for nasal, tracheal, bronchial, oral, or topical administration, or can be formulated as an injectable solution or as eyedrops. A pharmaceutical composition comprising a sialidase can be used to treat or prevent pathogen infection, to treat or prevent allergy or inflammatory response, or to enhance the transduction efficiency of a recombinant virus for gene therapy.

III. Sialidase Catalytic Domain Proteins

The present invention also includes sialidase catalytic domain proteins. As used herein a "sialidase catalytic domain protein" comprises a catalytic domain of a sialidase but does not comprise the entire amino acid sequence of the sialidase from which the catalytic domain is derived. A sialidase catalytic domain protein has sialidase activity. Preferably, a sialidase catalytic domain protein comprises at least 10%, at least 20%, at least 50%, at least 70% of the activity of the sialidase from which the catalytic domain sequence is derived. More preferably, a sialidase catalytic domain protein comprises at least 90% of the activity of the sialidase from which the catalytic domain sequence is derived.

A sialidase catalytic domain protein can include other amino acid sequences, such as but not limited to additional sialidase sequences, sequences derived from other proteins, or sequences that are not derived from sequences of naturally-occurring proteins. Additional amino acid sequences can perform any of a number of functions, including contributing other activities to the catalytic domain protein, enhancing the expression, processing, folding, or stability of the sialidase catalytic domain protein, or even providing a desirable size or spacing of the protein.

A preferred sialidase catalytic domain protein is a protein that comprises the catalytic domain of the *A. viscosus* sialidase. Preferably, an *A. viscosus* sialidase catalytic domain protein comprises amino acids 270-666 of the *A. viscosus* sialidase sequence (SEQ ID NO:12). Preferably, an *A. viscosus* sialidase catalytic domain protein comprises an amino acid sequence that begins at any of the amino acids from amino acid 270 to amino acid 290 of the *A. viscosus* sialidase sequence (SEQ ID NO:12) and ends at any of the amino acids from amino acid 665 to amino acid 901 of said *A. viscosus* sialidase sequence (SEQ ID NO:12), and lacks any *A. viscosus* sialidase protein sequence extending from amino acid 1 to amino acid 269. (As used herein "lacks any *A. viscosus* sialidase protein sequence extending from amino acid 1 to amino acid 269" means lacks any stretch of four or more consecutive amino acids as they appear in the designated protein or amino acid sequence.)

In some preferred embodiments, an *A. viscosus* sialidase catalytic domain protein comprises amino acids 274-681 of the *A. viscosus* sialidase sequence (SEQ ID NO:12) and lacks other *A. viscosus* sialidase sequence. In some preferred embodiments, an *A. viscosus* sialidase catalytic domain protein comprises amino acids 274-666 of the *A. viscosus* sialidase sequence (SEQ ID NO:12) and lacks any other *A. viscosus* sialidase sequence. In some preferred embodiments, an *A. viscosus* sialidase catalytic domain protein comprises amino acids 290-666 of the *A. viscosus* sialidase sequence (SEQ ID NO:12) and lacks any other *A. viscosus* sialidase sequence. In yet other preferred embodiments, an *A. viscosus* sialidase catalytic domain protein comprises amino acids 290-681 of the *A. viscosus* sialidase sequence (SEQ ID NO:12) and lacks any other *A. viscosus* sialidase sequence.

The present invention also comprises nucleic acid molecules that encode protein-based compounds of the present invention that comprise a catalytic domain of a sialidase. The nucleic acid molecules can have codons optimized for expression in particular cell types, such as, for example *E. coli* or human cells. The nucleic acid molecules or the present invention that encode protein-based compounds of the present invention that comprise at least one catalytic domain of a sialidase can also comprise other nucleic acid sequences, including but not limited to sequences that enhance gene expression. The nucleic acid molecules can be in vectors, such as but not limited to expression vectors.

Fusion Proteins

Sialidase catalytic domain proteins can be fusion proteins, in which the fusion protein comprises at least one sialidase catalytic domain and at least one other protein domain, including but not limited to: a purification domain, a protein tag, a protein stability domain, a solubility domain, a protein size-increasing domain, a protein folding domain, a protein localization domain, an anchoring domain, an N-terminal domain, a C-terminal domain, a catalytic activity domain, a binding domain, or a catalytic activity-enhancing domain. Preferably, the at least one other protein domain is derived from another source, such as, but not limited to, sequences from another protein. The at least one other protein domain need not be based on any known protein sequence, but can be engineered and empirically tested to perform any function in the fusion protein.

Purification domains can include, as nonlimiting examples, one or more of a his tag, a calmodulin binding domain, a maltose binding protein domain, a streptavidin domain, a streptavidin binding domain, an intein domain, or a chitin binding domain. Protein tags can comprise sequences that can be used for antibody detection of proteins, such as, for example, the myc tag, the hemagglutinin tag, or the FLAG tag. Protein domains that enhance protein expression, modification, folding, stability, size, or localization can be based on sequences of know proteins or engineered. Other protein domains can have binding or catalytic activity or enhance the catalytic activity of the sialidase catalytic domain.

Preferred fusion proteins of the present invention comprise at least one sialidase catalytic domain and at least one anchoring domain. Preferred anchoring domains include GAG-binding domains, such as the GAG-binding domain or human amphiregulin (SEQ ID NO:7).

Sialidase catalytic domains and other domains of a fusion protein of the present invention can optionally be joined by linkers, such as but not limited to peptide linkers. A variety of peptide linkers are known in the art. A preferred linker is a peptide linker comprising glycine, such as G-G-G-G-S (SEQ ID NO:10).

The present invention also comprises nucleic acid molecules that fusion proteins of the present invention that comprise a catalytic domain of a sialidase. The nucleic acid molecules can have codons optimized for expression in particular cell types, such as, for example E. coli or human cells. The nucleic acid molecules or the present invention that encode fusion proteins of the present invention can also comprise other nucleic acid sequences, including but not limited to sequences that enhance gene expression. The nucleic acid molecules can be in vectors, such as but not limited to expression vectors.

IV Pharmaceutical Compositions

The present invention includes compounds of the present invention formulated as pharmaceutical compositions. The pharmaceutical compositions comprise a pharmaceutically acceptable carrier prepared for storage and preferably subsequent administration, which have a pharmaceutically effective amount of the compound in a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990)). Preservatives, stabilizers, dyes and even flavoring agents can be provided in the pharmaceutical composition. For example, sodium benzoate, sorbic acid and esters of p-hydroxybenzoic acid can be added as preservatives. In addition, antioxidants and suspending agents can be used.

Depending on the target cell, the compounds of the present invention can be formulated and used as tablets, capsules or elixirs for oral administration; salves or ointments for topical application; suppositories for rectal administration; sterile solutions, suspensions, and the like for use as inhalants or nasal sprays. Injectables can also be prepared in conventional forms either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride and the like. In addition, if desired, the injectable pharmaceutical compositions can contain minor amounts of nontoxic auxiliary substances, such as wetting agents, pH buffering agents and the like.

The pharmaceutically effective amount of a test compound required as a dose will depend on the route of administration, the type of animal or patient being treated, and the physical characteristics of the specific animal under consideration. The dose can be tailored to achieve a desired effect, but will depend on such factors as weight, diet, concurrent medication and other factors which those skilled in the medical arts will recognize. In practicing the methods of the present invention, the pharmaceutical compositions can be used alone or in combination with one another, or in combination with other therapeutic or diagnostic agents. These products can be utilized in vivo, preferably in a mammalian patient, preferably in a human, or in vitro. In employing them in vivo, the pharmaceutical compositions can be administered to the patient in a variety of ways, including topically, parenterally, intravenously, subcutaneously, intramuscularly, colonically, rectally, nasally or intraperitoneally, employing a variety of dosage forms. Such methods can also be used in testing the activity of test compounds in vivo.

In preferred embodiments, these pharmaceutical compositions may be in the form of orally-administrable suspensions, solutions, tablets or lozenges; nasal sprays; inhalants; injectables, topical sprays, ointments, powders, or gels.

When administered orally as a suspension, compositions of the present invention are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art. Components in the formulation of a mouthwash or rinse include antimicrobials, surfactants, cosurfactants, oils, water and other additives such as sweeteners/flavoring agents known in the art.

When administered by a drinking solution, the composition comprises one or more of the compounds of the present invention, dissolved in water, with appropriate pH adjustment, and with carrier. The compound may be dissolved in distilled water, tap water, spring water, and the like. The pH can preferably be adjusted to between about 3.5 and about 8.5. Sweeteners may be added, e.g., 1% (w/v) sucrose.

Lozenges can be prepared according to U.S. Pat. No. 3,439,089, herein incorporated by reference for these purposes.

When administered by nasal aerosol or inhalation, the pharmaceutical compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in Remington's Pharmaceutical Sciences, 18th Ed., Mack Publishing Co., Easton, Pa. (1990, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, jelling agents, or buffering and other stabilizing and solubilizing agents may also be present. Preferably, the nasal dosage form should be isotonic with nasal secretions.

Nasal formulations can be administers as drops, sprays, aerosols or by any other intranasal dosage form. Optionally, the delivery system can be a unit dose delivery system. The volume of solution or suspension delivered per dose can preferably be anywhere from about 5 to about 2000 microliters, more preferably from about 10 to about 1000 microliters, and yet more preferably from about 50 to about 500 microliters. Delivery systems for these various dosage forms can be dropper bottles, plastic squeeze units, atomizers, nebulizers or pharmaceutical aerosols in either unit dose or multiple dose packages.

The formulations of this invention may be varied to include; (1) other acids and bases to adjust the pH; (2) other tonicity imparting agents such as sorbitol, glycerin and dextrose; (3) other antimicrobial preservatives such as other parahydroxy benzoic acid esters, sorbate, benzoate, propionate, chlorbutanol, phenylethyl alcohol, benzalkonium chloride, and mercurials; (4) other viscosity imparting agents such as sodium carboxymethylcellulose, microcrystalline cellulose, polyvinylpyrrolidone, polyvinyl alcohol and other gums; (5) suitable absorption enhancers; (6) stabilizing agents such as antioxidants, like bisulfite and ascorbate, metal chelating agents such as sodium edetate and drug solubility enhancers such as polyethylene glycols.

V. Method of Preventing or Treating Infection by a Pathogen

The present invention also includes methods of preventing or treating infection by a pathogen. In one aspect, the method includes: treating a subject that is infected with a pathogen or at risk of being infected with a pathogen with a pharmaceutical composition of the present invention that comprises a compound that comprises at least one anchoring domain that can anchor the compound at or near the surface of a target cell and at least one therapeutic domain comprising a peptide or protein that has at least one extracellular activity that can prevent the infection of a target cell by a pathogen. In some preferred embodiments, the method includes applying a therapeutically effective amount of a pharmaceutical composition of the present invention to epithelial cells of a subject. The subject to be treated can be an animal or human subject.

In another aspect, the method includes: treating a subject that is infected with a pathogen or at risk of being infected with a pathogen with a pharmaceutical composition of the present invention that comprises a protein-based compound that comprises a sialidase activity. In some preferred embodiments, the method includes applying a therapeutically effective amount of a pharmaceutical composition of the present invention to epithelial cells of a subject. The sialidase activity can be an isolated naturally occurring sialidase protein, or a recombinant protein substantially homologous to at least a portion of a naturally occurring sialidase. A preferred pharmaceutical composition comprises a sialidase with substantial homology to the *A. viscosus* sialidase (SEQ ID NO:12). The subject to be treated can be an animal or human subject.

In yet another aspect, the method includes: treating a subject that is infected with a pathogen or at risk of being infected with a pathogen with a pharmaceutical composition of the present invention that comprises a protein-based compound that comprises a sialidase catalytic domain. In some preferred embodiments, the method includes applying a therapeutically effective amount of a pharmaceutical composition of the present invention to epithelial cells of a subject. The sialidase catalytic domain is preferably can substantially homologous to the catalytic domain of a naturally occurring sialidase. A preferred pharmaceutical composition comprises a sialidase catalytic domain with substantial homology to amino acids 274-666 the *A. viscosus* sialidase (SEQ ID NO:12). The subject to be treated can be an animal or human subject.

A pathogen can be a viral, bacterial, or protozoan pathogen. In some embodiments, the pathogen is one of the following: influenza viruses, parainfluenza virus, respiratory syncytial virus (RSV), coronavirus, rotavirus, *Streptococcus pneumoniae, Mycoplasma pneumoniae, Haemophilus influenzae, Moraxella catarrhalis, Pseudomonas aeruginosa*, and *Helicobacter pylori*. In one preferred embodiment, the pathogen is influenza virus.

Compounds of the present invention can be designed for human use or animal use. In some aspects of the present invention, a compound of the present invention can be used to prevent pathogen infection in a class of animals, such as mammals. In some aspects of the present invention, a composition can be used for human and animal use (although the formulation may differ). In these aspects, the active domains of a compound can be effective against more than one pathogen species, type, subtype, or strain and can be active in more than one host species. For example, some preferred compounds of the present invention that comprise, for example, active domains such as protease inhibitors that prevent processing of the HA protein of influenza virus, or sialidases that remove sialic acid receptors from target cells, or anchoring domains such as domains that bind heparin or heparan sulfate, can be used in birds, mammals, or humans. Such compounds that can be effective against a range of pathogens with the capacity to infect different host species can also be used in humans to combat infection by pathogens that are naturally hosted in other species.

In some preferred embodiments of the present invention, the pharmaceutical composition prevents infection by influenza, and a therapeutically effective amount of the pharmaceutical composition is applied to the respiratory epithelial cells of a subject. This can be done by the use of an inhaler, or by the use of a nasal spray. Preferably, the inhaler or nasal spray is used from one to four times a day.

Because influenza viruses primarily infect the upper respiratory tract, removing the receptor sialic acid locally in the nasal cavity, pharynx, trachea and bronchi can prevent infections or interrupt early infections. The sialidase can be delivered to the upper respiratory tract as a nasal spray or as an inhalant, and it can be used either in therapeutic mode during early stage of influenza (or other infection) or in prophylactic mode before the infection occurs. Alternatively, it can be delivered to the lower respiratory tract as an inhalant to treat influenza and to prevent influenza complications, such as bronchopneumonia. Similarly, the sialidase can be delivered as nasal spray or inhalant to prevent or reduce infection by parainfluenza virus and coronavirus. It can also be delivered as an inhalant or nasal spray to prevent or reduce airway colonization by pathogenic bacteria, including *Streptococcus pneumoniae, Mycoplasma pneumoniae, Haemophilus influenzae, Moraxella catarrhalis* and *Pseudomonas aeruginosa*. The therapeutic compounds can optionally be adapted, by genetic or chemical engineering, or by pharmaceutical formulation, to improve their half-life or retention at the respiratory epithelium. Additionally, it can be delivered topically to the eyes or to surgical wounds in the form of drops, sprays or ointments to prevent and treat bacterial infection including infection by *Pseudomonas aeruginosa*. It can also be administered orally to treat infection by *Helicobacter pylori*.

Dosage

As will be readily apparent to one skilled in the art, the useful in vivo dosage to be administered and the particular mode of administration will vary depending upon the age, weight and type of patient being treated, the particular pharmaceutical composition employed, and the specific use for which the pharmaceutical composition is employed. The determination of effective dosage levels, that is the dose levels necessary to achieve the desired result, can be accomplished by one skilled in the art using routine methods as discussed above. In non-human animal studies, applications of the pharmaceutical compositions are commenced at higher dose levels, with the dosage being decreased until the desired effect is no longer achieved or adverse side effects are reduced or disappear. The dosage for a compound of the present invention can range broadly depending upon the desired affects, the therapeutic indication, route of administration and purity and activity of the compound. Typically, human clinical applications of products are commenced at lower dosage levels, with dosage level being increased until the desired effect is achieved. Alternatively, acceptable in vitro studies can be used to establish useful doses and routes of administration of the test compound. Typically, dosages can be between about 1 ng/kg and about 10 mg/kg, preferably between about 10 ng/kg and about 1 mg/kg, and more preferably between about 100 ng/kg and about 100 micrograms/kg.

The exact formulation, route of administration and dosage can be chosen by the individual physician in view of the patient's condition (see, Fingle et al., in The Pharmacological Basis of Therapeutics (1975)). It should be noted that the attending physician would know how to and when to terminate, interrupt or adjust administration due to toxicity, organ dysfunction or other adverse effects. Conversely, the attending physician would also know to adjust treatment to higher levels if the clinical response were not adequate. The magnitude of an administrated does in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight and response of the individual patient, including those for veterinary applications.

Thus, in accordance with the present invention, there is further provided a method of treating and a pharmaceutical composition for treating influenza virus infection and prevention of influenza virus infection. The treatment involves administering to a patient in need of such treatment a pharmaceutical carrier and a therapeutically effective amount of any composition of the present invention, or a pharmaceutically acceptable salt thereof.

In one preferred regimen, appropriate dosages are administered to each patient by either inhaler, nasal spray, or by oral lozenge. It will be understood, however, that the specific dose level and frequency of dosage for any particular patient may be varied and will depend upon a variety of factors including the activity of the specific salt or other form employed, the metabolic stability and length of action of that compound, the age, body weight, general health, sex, diet, mode and time of administration, rate of excretion, drug combination, the severity of the particular condition, and the host undergoing therapy.

VI. Method of Reducing, Preventing, or Treating Allergic and Inflammatory Responses The present invention also includes methods of reducing, preventing, or treating an allergic or inflammatory response of a subject.

In one aspect, the method includes: preventing or treating an allergic or inflammatory response of a subject with a pharmaceutical composition of the present invention that comprises a protein-based compound that comprises a sialidase activity. In some preferred embodiments, the method includes applying a therapeutically effective amount of a pharmaceutical composition of the present invention to epithelial cells of a subject. The sialidase activity can be an isolated naturally occurring sialidase protein, or a recombinant protein substantially homologous to at least a portion of a naturally occurring sialidase. A preferred pharmaceutical composition comprises a sialidase with substantial homology to the *A. viscosus* sialidase (SEQ ID NO:12). The subject to be treated can be an animal or human subject.

In yet another aspect, the method includes: preventing or treating an allergic or inflammatory response of a subject with a pharmaceutical composition of the present invention that comprises a protein-based compound that comprises a sialidase catalytic domain. In some preferred embodiments, the method includes applying a therapeutically effective amount of a pharmaceutical composition of the present invention to epithelial cells of a subject. The sialidase catalytic domain is preferably can substantially homologous to the catalytic domain of a naturally occurring sialidase. A preferred pharmaceutical composition comprises a sialidase catalytic domain with substantial homology to amino acids 274-666 the *A. viscosus* sialidase (SEQ ID NO:12). The subject to be treated can be an animal or human subject.

The allergic or inflammatory response can be and acute or chronic condition, and can include, as nonlimiting examples, asthma, other allergic responses causing respiratory distress, allergic rhinitis, eczema, psoriasis, reactions to plant or animal toxins, or autoimmune conditions.

In some preferred embodiments, compounds of the present invention can be delivered as an inhalant or nasal spray to prevent or treat inflammation in the airway including, but not limited to, asthma and allergic rhinitis. Compounds of the present invention comprising sialidase activity (including sialidase catalytic domain proteins and sialidase fusion proteins) can also be administered as eye drops, ear drops, or sprays, ointments, lotions, or gels to be applied to the skin. In another aspect, the method includes treating a patient who has inflammatory diseases with the present invention that comprises a sialidase activity that is administered intravenously or as a local injection.

Dosage

As will be readily apparent to one skilled in the art, the useful in vivo dosage to be administered and the particular mode of administration will vary depending upon the age, weight and type of patient being treated, the particular pharmaceutical composition employed, and the specific use for which the pharmaceutical composition is employed. The determination of effective dosage levels, that is the dose levels necessary to achieve the desired result, can be accomplished by one skilled in the art using routine methods as discussed above. In non-human animal studies, applications of the pharmaceutical compositions are commenced at higher dose levels, with the dosage being decreased until the desired effect is no longer achieved or adverse side effects are reduced or disappear. The dosage for a compound of the present invention can range broadly depending upon the desired affects, the therapeutic indication, route of administration and purity and activity of the compound. Typically, human clinical applications of products are commenced at lower dosage levels, with dosage level being increased until the desired effect is achieved. Alternatively, acceptable in vitro studies can be used to establish useful doses and routes of administration of the test compound. Typically, dosages can be between about 1 ng/kg and about 10 mg/kg, preferably between about 10 ng/kg and about 1 mg/kg, and more preferably between about 100 ng/kg and about 100 micrograms/kg.

The exact formulation, route of administration and dosage can be chosen by the individual physician in view of the patient's condition (see, Fingle et al., in The Pharmacological Basis of Therapeutics (1975)). It should be noted that the attending physician would know how to and when to terminate, interrupt or adjust administration due to toxicity, organ dysfunction or other adverse effects. Conversely, the attending physician would also know to adjust treatment to higher levels if the clinical response were not adequate. The magnitude of an administrated does in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight and response of the individual patient, including those for veterinary applications.

In some preferred regimens, appropriate dosages are administered to each patient by either inhaler, nasal spray, or by topical application. It will be understood, however, that the specific dose level and frequency of dosage for any particular patient may be varied and will depend upon a variety of factors including the activity of the specific salt or other form employed, the metabolic stability and length of action of that compound, the age, body weight, general health, sex, diet, mode and time of administration, rate of excretion, drug combination, the severity of the particular condition, and the host undergoing therapy.

VII. Method of Enhancing Gene Delivery by a Recombinant Viral Vector

The present invention also includes methods of gene delivery by a recombinant viral vector. In one aspect, the method includes: administering an effective amount of a compound of the present invention that comprises a protein having sialidase activity to at least one cell prior to or concomitant with the administration of at least one recombinant viral vector. A composition of the present invention can be provided in the same formulation as at least one recombinant viral vector, or in a separate formulation.

In some preferred embodiments, the method includes applying a therapeutically effective amount of a composition of the present invention and a recombinant viral vector to cells of a subject. The subject to be treated can be an animal or human subject. In a particularly preferred embodiment, a recombinant viral vector is used to transduce epithelial target cells of a subject for gene therapy. For example, a recombinant viral vector can be used to transduce airway epithelial cells of a subject with cystic fibrosis. In this case, a compound of the present invention can be administered by use of an inhaler. A recombinant virus comprising a therapeutic gene can be administered concurrently or separately.

In other embodiments, cells can be treated with a compound of the present invention and a recombinant viral vector in vitro or "ex vivo" (that is, cells removed from a subject to be transplanted into a subject after transduction).

The sialidase activity can be an isolated naturally occurring sialidase protein, or a recombinant protein substantially homologous to at least a portion of a naturally occurring sialidase, including a sialidase catalytic domain. A preferred pharmaceutical composition comprises a sialidase with substantial homology to the *A. viscosus* sialidase (SEQ ID NO:12).

A compound of the present invention can be administered to target cells from one day before to two hours subsequent to the administration of the recombinant virus. Preferably a compound of the present invention is administered to target cells from four hours to ten minutes before administration of the recombinant virus. Administration can be A recombinant virus is preferably a recombinant virus that can be used to transfer genes to mammalian cells, such as, preferably human cells. For example, a recombinant virus can be a retrovirus (including lentivirus), adenovirus, adeno-associated virus (AAV) or herpes simplex virus type 1. The recombinant virus comprises at least one exogenous gene that is to be transferred to a target cell. The gene is preferably a therapeutic gene, but this need not be the case. For example, the gene can be a gene used to mark cells or confer drug resistance.

In a preferred embodiment, the present invention includes methods of improving efficacy of a gene therapy vector. The method includes treating a patient with a compound of the present invention that comprises a sialidase activity and, in the same or a separate formation, with a recombinant virus. The compound of the present invention having sialidase activity can be administered to the patient prior to, concomitant to, or even subsequent to the administration of a recombinant virus. In one embodiment, the sialidase is substantially homologous to the *Actinomyces viscosus* sialidase (SEQ ID NO:12) or a portion thereof. In one preferred embodiment, the sialidase comprises the catalytic domain of the *Actinomyces viscosus* sialidase. In another embodiment, the recombinant virus is AAV. In yet another embodiment, the disease is cystic fibrosis. In yet another embodiment, the recombinant virus comprises the cystic fibrosis transmembrane conductance regulator (CFTR) gene.

Dosage

As will be readily apparent to one skilled in the art, the useful in vivo dosage to be administered and the particular mode of administration will vary depending upon the age, weight and type of patient being treated, the particular pharmaceutical composition employed, and the specific use for which the pharmaceutical composition is employed. The determination of effective dosage levels, that is the dose levels necessary to achieve the desired result, can be accomplished by one skilled in the art using routine methods as discussed above. In non-human animal studies, applications of the pharmaceutical compositions are commenced at higher dose levels, with the dosage being decreased until the desired effect is no longer achieved or adverse side effects are reduced or disappear. The dosage for a compound of the present invention can range broadly depending upon the desired affects, the therapeutic indication, route of administration and purity and activity of the compound. Typically, human clinical applications of products are commenced at lower dosage levels, with dosage level being increased until the desired effect is achieved. Alternatively, acceptable in vitro studies can be used to establish useful doses and routes of administration of the test compound. Typically, dosages can be between about 1 ng/kg and about 10 mg/kg, preferably between about 10 ng/kg and about 1 mg/kg, and more preferably between about 100 ng/kg and about 100 micrograms/kg.

The exact formulation, route of administration and dosage can be chosen by the individual physician in view of the patient's condition (see, Fingle et al., in The Pharmacological Basis of Therapeutics (1975)). It should be noted that the attending physician would know how to and when to terminate, interrupt or adjust administration due to toxicity, organ dysfunction or other adverse effects. Conversely, the attending physician would also know to adjust treatment to higher levels if the clinical response were not adequate. The magnitude of an administrated does in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight and response of the individual patient, including those for veterinary applications.

In some preferred regimens, appropriate dosages are administered to each patient by either inhaler, nasal spray, or by topical application. It will be understood, however, that the specific dose level and frequency of dosage for any particular patient may be varied and will depend upon a variety of factors including the activity of the specific salt or other form employed, the metabolic stability and length of action of that compound, the age, body weight, general health, sex, diet, mode and time of administration, rate of excretion, drug combination, the severity of the particular condition, and the host undergoing therapy.

EXAMPLES

Example 1: Synthesizing Aprotinin Genes, Purifying and Testing Aprotinin Fusion Proteins Introduction Influenza viral protein hemagglutinin (HA) is the major influenza envelope protein. It plays an essential role in viral infection. The importance of HA is evidenced by the fact that it is the major target for protective neutralizing antibodies produced by the host immune response (Hayden, F G. (1996) In *Antiviral drug resistance* (ed. D. D. Richman), pp. 59-77. Chichester, U K: John Wiley & Sons Ltd.). It is now clear that HA has two different functions in viral infection. First, HA is responsible for the attachment of the virus to sialic acid cell receptors. Second, HA mediates viral entry into target cells by triggering fusion of the viral envelope with cellular membranes.

HA is synthesized as a precursor protein, HA0, which is transferred through the Golgi apparatus to the cell surface as a trimeric molecular complex. HA0 is further cleaved to generate the C terminus HA1 (residue 328 of HA0) and the N terminus of HA2. It is generally believed that the cleavage occurs at the cell surface or on released viruses. The cleavage of HA0 into HA1/HA2 is not required for HA binding to a sialic acid receptor; however, it is essential for viral infectivity (Klenk, H D and Rott, R. (1988) *Adv Vin Res.* 34:247-281; Kido, H, Niwa, Y, Beppu, Y and Towatari, T. (1996) *Advan Enzyme Regul* 36:325-347; Skehel, J J and Wiley, D C. (2000) *Annu Rev Biochem* 69:531-569).

Sensitivity of HA0 to host proteases is determined by the proteolytic site in the external loop of HA0 molecule. The proteolytic site may contain either a single Arg or Lys residue (monobasic cleavage site) or several Lys and/or Arg residues in R—X—K/R—R motif (multibasic cleavage site). Only the influenza A virus subtypes H5 and H7 have HA proteins carrying the multibasic cleavage site. All other influenza A, B and C viruses contain HA proteins having the monobasic cleavage site. Influenza A viruses having multibasic cleavage sites are more virulent and induce systemic infection in hosts whereas viruses with a monobasic HA site initiate infection only in the respiratory tract in mammals or in the respiratory and enteric tracts in avian species (Klenk, H D and Garten W. 1994. Trend Micro 2:39-43 for review). Fortunately, human infection by the highly virulent avian influenza A H5 and H7 subtypes, which carry the multibasic cleavage site, has so far only occurred in a handful of cases discovered mostly in Hong Kong. The vast majority of influenza infections are caused by viruses with HA proteins are cleaved at the monobasic cleavage site.

Influenza virus HA subtypes 5 and 7 that contain multibasic cleavage sites are activated by furin, a member of the subtilisin-like endoproteases, or the pre-protein convertase family. Furin cleaves the virus intracellularly and is ubiquitously present in many cell types, allowing the virulent, systemic infection seen with such viruses (Klenk, H D and Garten W. 1994. *Trend Micro* 2:39-43; Nakayama, K. 1997. *Biochem* 327:625-635). All other influenza viruses, which have HAs with monobasic cleavage sites, are activated by secreted, trypsin-like serine proteases. Enzymes that have been implicated in influenza virus activation include: plasmin (Lazarowitz S G, Goldberg A R and Choppin P W. 1973. *Virology* 56:172-180), mini-plasmin (Murakami M, Towatari T, Ohuchi M, Shiota M, Akao M, Okumura Y, Parry M A and Kido H. (2001) *Eur J Biochem* 268: 2847-2855), tryptase Clara (Kido H, Chen Y and Murakami M. (1999) In B. Dunn (ed.), Proteases of infectious agents. p. 205-217, Academic Press, New York, N.Y), kallikrein, urokinase, thrombin (Scheiblauer H, Reinacher M, Tashiro M and Rott R. (1992) *J Infec Dis* 166:783-791), blood clotting factor Xa (Gotoh B, Ogasawara T, Toyoda T, Inocencio N, Hamaguchi M and Nagai Y. (1990) *EMBO J* 9:4189-4195), acrosin (Garten W, Bosch F X, Linder D, Rott R and Klenk H D. (1981) *Virology* 115:361-374.), proteases from human respiratory lavage (Barbey-Morel C L, Oeltmann T N, Edwards K M and Wright P F. (1987) *J Infect Dis* 155:667-672) and bacterial proteases from *Staphylococcus aureus* (Tashiro M, Ciborowski P, Reinacher M, Pulverer G, Klenk H D and Rott R. (1987) *Virology* 157:421-430) and *Pseudomonas aeruginosa* (Callan R J, Hartmann F A, West S E and Hinshaw V S. (1997) *J Virol* 71:7579-7585). Activation of influenza viruses by host serine proteases is generally considered to occur extracellularly either at the plasma membrane or after virus release from the cell.

Aprotinin, also called Trasylol, or bovine pancreatic trypsin inhibitor (BPTI) is a polypeptide having 58 amino acids. It belongs to the family of Kunitz-type inhibitors and competitively inhibits a wide spectrum of serine proteases, including trypsin, chymotrypsin, plasmin and plasma kallikrein. Aprotinin has long been used as a human therapeutics, such as treatment of pancreatitis, various states of shock syndrome, hyperfibrinolytic haemorrhage and myocardial infarction. It is also used in open-heart surgery, including cardiopulmonary bypass operations, to reduce blood loss (Fritz H and Wunderer G. (1983) *Arzneim-Forsch* 33:479-494).

The safety of aprotinin in human has been well documented through years of clinical applications. In addition, aprotinin is apparently a very weak immunogen as aprotinin-specific antibodies have not been observed in human sera so far (Fritz H and Wunderer G. (1983) *Arzneim-Forsch* 33:479-494). Another desired feature of aprotinin as a drug candidate is its superb stability. It can be kept at room temperature for at least 18 months without any loss of activity (Fritz H and Wunderer G. (1983) *Arzneim-Forsch* 33:479-494).

To achieve significant viral inhibition in animal studies that have been performed, aprotinin was administered at high doses. For example, 280 micrograms to 840 micrograms per day of aprotinin was injected intraperitoneally into each mouse for 6 days (Zhirnov O P, Ovcharenko A V and Bukrinskaya A G. (1984) *J Gen Virol* 65:191-196); a lower dosage was required for aerosol inhalation, still, each mouse was given 63-126 micrograms per day for 6 days (Ovcharenko A V and Zhirnov O P. (1994) *Antiviral Res* 23:107-118). A very high dose of aprotinin would be required in human based on extrapolation from the mouse data. Therefore to achieve better efficacy in human, the potency of aprotinin molecule needs to be significantly improved.

Aprotinin functions by competitively inhibiting serine proteases that are mostly on the surface of host respiratory epithelial cells. Local concentration of aprotinin in the vicinity of host proteases is therefore the key factor determining competitive advantage of aprotinin. We use two approaches that work synergistically to boost competitive advantage of aprotinin on the surface of respiratory epithelium.

First, the avidity (functional affinity) of aprotinin is increased by making multivalent aprotinin fusion proteins consisting of two, three, or more aprotinin proteins connected via linkers. Such a molecule is able to bind to membrane proteases in a multivalent fashion, which has significant kinetic advantage over the aprotinin monomer. Monomeric aprotinin binds to bovine trypsin very tightly with dissociation constant (Ki) being $6.0 \times 10^{-14}$ mol/l. However, its affinity compared to other proteases, such as chymotrypsin, plasmin and Kallikrein, which have been implicated in activation of influenza viruses, is much lower with Ki being at the level of $10^{-8}$ to $10^{-9}$ mol/l (Fritz H and Wunderer G. (1983) *Arzneim-Forsch* 33:479-494). Multimerization can increase aprotinin's affinity to these proteases exponentially.

Second, we fuse aprotinin with a respiratory epithelium-anchoring domain. The anchoring domain localizes aprotinin to the proximity of host membrane-associated proteases and maintains a high local concentration of aprotinin on epithelial surface. The anchoring domain also increases retention time of the drug on the respiratory epithelium.

Cloning

Aprotinin is a single chain polypeptide having 58 amino acid residues and 3 intra-chain disulfide bonds (SEQ ID NO:1). The amino acid sequence of aprotinin is shown in FIG. 1. Genes encoding aprotinin and aprotinin fusion proteins are synthesized by PCR using overlapping oligonucleotides with codons optimized for *E. Coli* expression as templates. The PCR products are cloned into pCR2.1-TOPO vector (Invitrogen). After sequencing, the genes are subcloned into an expression vector pQE (Qiagen). The vector carries a purification tag, His×6, to allow easy purification of the recombinant proteins. The constructs are used to transform *E. Coli*. The transformed cells grown in LB-ampicillin medium to mid-log phase are induced by IPTG according to standard protocols. Cells are pelleted and lysed in phosphate-buffered-saline (PBS) by sonication. The enzymes, which have $His_6$ purification tag, are purified using a nickel column (Qiagen).

The following aprotinin fusion proteins are made:
1. Dimeric and Trimeric Aprotinin.

Two or three aprotinin genes are linked via a flexible linker as the following constructs:

```
Aprotinin-(GGGGS (SEQ ID NO: 10))n (n = 3, 4 or 5)-
Aprotinin;
and

Aprotinin-(GGGGS (SEQ ID NO: 10))n (n = 3, 4 or 5)-
Aprotinin-(GGGGS (SEQ ID NO: 10))n (n = 3, 4 or 5)-
Aprotinin
```

The length of the linker sequence may determine three-dimensional flexibility of the multimeric aprotinin and thereby influence functional affinity of the molecule. Therefore constructs having linkers with various lengths are made.

Fully functional recombinant monomeric aprotinin has been produced in *E. Coli* (Auerswald E A, Horlein D, Reinhardt G, Schroder W and Schnabel E. (1988). *Biol Chem Hoppe-Seyler* Vol 369, Suppl., pp 27-35). We therefore expect proper folding of multivalent aprotinin proteins in *E. coli* cells. Besides expressing protein in various common *E. Coli* cell strains, such as BL21, JM83, etc, the multivalent aprotinin proteins are also expressed in Origami™ cells (Novagen, Bad Soden, Germany). The Origami™ cell strain does not have thioredoxin and glutathione reductase and thus has an oxidizing cytoplasm. This cell strain has been used to successfully express a number of proteins that contain disulfide bonds (Bessette P H, Aslund F, Beckwith J and Georgiou G. (1999) Pro *Natl Acad Sci USA* 96:13703-13708; Venturi M, Seifert C and Hunte C. (2001) *J Mol Biol*. 315:1-8.).

2. The Epithelium Cell-Anchoring Aprotinin.

An epithelium cell-anchoring sequence is fused with aprotinin. The epithelium-anchoring sequence can be any peptide or polypeptide sequence that has affinity towards the surface of epithelial cells. We have selected three human GAG-binding sequences: PF4 (aa 47-70; SEQ ID NO: 2), IL-8 (aa 46-72; SEQ ID NO: 3), and AT III (aa 118-151; SEQ ID NO: 4) (FIG. 2). These sequences bind to heparin/heparan sulfate with nanomolar-level affinities (Table 1). Heparin/Heparan Sulfate are ubiquitously present on the respiratory epithelium. In separate constructs, the GAG-binding sequences are fused with the aprotinin gene on the N terminus and on the C terminus via a generic linker sequence GGGGS as the following constructs:

```
(GAG domain-GGGGS (SEQ ID NO: 10)-Aprotinin);
and (Aprotinin-GGGGS (SEQ ID NO: 10)-GAG domain)
```

TABLE 1

| Affinities to Heparin | |
|---|---|
| Protein | Kd nM (ref) |
| PF4 | 27 (44) |
| IL-8 | <5 (43) |
| ATIII | 11 (42) |
| ApoE | 620 (45) |

Photometric Trypsin Inhibition Assay

The trypsin inhibition activity of aprotinin and aprotinin fusion proteins is measured by a photometric assay described previously in detail (Fritz H and Wunderer G. (1983) *Arzneim-Forsch* 33:479-494). Briefly, in this assay aprotinin inhibits the trypsin-catalyzed hydrolysis of Na-benzoyl-L-arginine-p-nitroanilide (BzArgpNA or L-BAPA) (Sigma), which is followed photometrically at 405 nm. One trypsin unit ($U_{BAPA}$) corresponds to the hydrolysis of 1 micromole substrate per min. One inhibitor unit ($IU_{BAPA}$) decreases the activity of two trypsin units by 50%, which corresponds arithmetically to the inhibition of 1 $U_{BAPA}$ of trypsin. The specific activity of aprotinin is given in $IU_{BAPA}$/mg polypeptide.

Surface Plasmon Resonance Assay

The affinities of dimeric and trimeric aprotinin with various linkers are compared against the monomeric aprotinin using surface plasmon resonance assay, or BIAcore analysis (BIAcore, Piscataway, N.J.) with human plasmin as the target. Similarly, BIAcore assay with heparin as the target is used to analyze affinity between GAG binding aprotinin fusion proteins and heparin.

When plasmin is used as the target, purified human plasmin (Sigma) is immobilized on the CM5 chip according manufacturer's instructions (BIAcore, Piscataway, N.J.). When heparin is the target, biotinylated albumin and albumin-heparin (Sigma) are captured on a streptavidin-coated BIAcore SA chip as described previously (Xiang Y and Moss B. (2003) *J Virol* 77:2623-2630).

Example 2: Establishing Improved Tissue Culture Models for Studies on Influenza Virus Infection Stocks of Influenza Viruses Influenza viral strains are obtained from ATCC and the repository at St. Jude Children's Research Hospital. All experiments involving influenza viruses are conducted at Bio-safety level II.

Viruses are propagated by injection into the allantoic cavity of nine-day-old chicken embryos as described (Zhirnov O P, Ovcharenko A V and Bukrinskaya A G. (1985) *J Gen Virol* 66:1633-1638). Alternatively, viral stocks are grown on Madin-Darby canine kidney (MDCK) cells in minimal essential medium (MEM) supplemented with 0.3% bovine serum albumin and 0.5 micrograms of trypsin per ml. After incubating for 48 to 72 hours, the culture medium is clarified by low speed centrifugation. Viral particles are pelleted by ultracentrifugation through a 25% sucrose cushion. Purified viruses are suspended in 50% glycerol-0.1M Tris buffer (pH 7.3) and stored at $-20°$ C.

Plaque Assays

Infectivity and titer of the viral stocks are determined by two kinds of plaque assays, a conventional one and a modified one (Tobita, K, Sugiura, A, Enomoto, C and Furuyama, M. (1975) *Med Microbiol Immnuol* 162:9-14; Zhirnov O P, Ovcharenko A V and Bukrinskaya A G. (1982) *Arch Virol* 71:177-183). The conventional plaque assay is routinely used as a virus titration method. It requires exogenous trypsin in agar overlay added immediately after virus infection to MDCK monolayers (Tobita, K, Sugiura, A, Enomoto, C and Furuyama, M. (1975) *Med Microbiol Immnuol* 162:9-14). This method artificially increases infectivity of the viral stocks being tested by activating all the viral particles that have uncleaved HA.

Zhirnov et. al. designed a modified plaque assay consisting of a double agar overlay, with trypsin being included in the second layer which is added 24 hours after infection (Zhirnov O P, Ovcharenko A V and Bukrinskaya A G. (1982) *Arch Virol* 71:177-183). Three days after infection, cells are fixed with a 10% formaldehyde solution, agarose layers are removed, fixed cells are stained with hematoxylin-eosin solution and plaques are counted. The modified plaque assay allows accurate determination of the real infectivity of viral stocks that contain both cleaved and uncleaved HA. Combining results from both conventional and modified plaque assays, one can distinguish viruses containing cleaved or uncleaved HA and correlate infectivity of viral stocks with the status of HA cleavage.

Human Cell Culture Models

1. Short-Term Culture of Primary Human Epithelial Cells.

Conventional in vitro influenza virus infection is mostly carried out in MDCK cells with exogenous trypsin added to the culture medium. This is far from being physiological and is inappropriate for the work proposed here because trypsin is not the protease that activate influenza viruses in vivo. Very limited numbers of in vitro tissue culture models that are able to support the growth of influenza virus without an exogenous protease have been reported so far, those being primary cultures with primate cells of renal origin, cells lining the allantoic and amniotic cavities of embryonated eggs, fetal tracheal ring organ cultures and primary human adenoid epithelial cells (Endo Y, Carroll K N, Ikizler M R and Wright P F. (1996) *J Virol* 70:2055-2058). Among these, the latest work with primary human adenoid epithelial cells is the closest mimic of human conditions. In this case, Endo et. al. (Endo Y, Carroll K N, Ikizler M R and Wright P F. (1996) *J Virol* 70:2055-2058) isolated epithelial cells from surgical samples of human adenoids, and cultured the epithelial cells on a collagen matrix (Vitrogen 100, Celtrix Laboratories, Palo Alto, Calif.) in Transwell inserts (Costar, Cambridge, Mass.). Cells were maintained in 50% Ham's F12 and 50% Eagles minimal essential media with supplements of growth factors and trace elements. The cells reached confluency in 10 to 14 days, remaining largely as a monolayer but with discrete patches of ciliated cells, which maintained regular ciliary activity for 1 to 3 weeks after reaching confluency. In this system, influenza A virus grew to a titer of $10^6$ PFU/ml with a multiplicity of infection of 0.001 (Endo Y, Carroll K N, Ikizler M R and Wright P F. (1996) *J Virol* 70:2055-2058). Progressive cytopathogenic effects were also present during infection. The biggest drawback of this system is that it requires fresh human adenoid tissue.

To solve this problem, primary human adenoid epithelial cells are replaced with primary human airway epithelial cells that are commercially available (Cambrex), and the cells are grown under the same conditions. Such short-term culture of primary human airway epithelial cells is relatively quick to establish and is useful as the first-line experimental model for most of the in vitro infection and antiviral experiments.

2. Well-Differentiated Human Airway Epithelium (WD-HAE).

In order to best mimic the in vivo condition of human airway, the model of well-differentiated human airway epithelium (WD-HAE) is used. WD-HAE is stratified epithelium that has all the differentiated cells of the normal human airway epithelium, including functional ciliated cells and mucus secreting cells. Therefore, in this model system influenza viruses are most likely to be activated by host proteases that are physiologically relevant. Although WD-HAE has been widely used to study respiratory viral infections, such as respiratory syncytial virus (RSV) (Zhang L, Peeples M E, Boucher R C, Collins P L and Pickles R J. (2002) *J Virol* 76:5654-5666) measles virus (Sinn P L, Williams G, Vongpunsawad S, Cattaneo R and McCray P B. (2002) *J Virol* 76:2403-2409, or human rhinovirus, it has not previously been used to study influenza viruses.

A detailed protocol of W D-HAE has been described previously (Krunkosky T M, Fischer B M, Martin L D, Jones N, Akley N J and Adler K B. (2000) *Am J Respir Cell Mol Biol* 22:685-692). Briefly, commercial primary human bronchial epithelial cells (Cambrex) are cultured on Transwell-clear culture inserts (Costar) that are thin-coated with rat-tail collagen I. Cells are cultured submerged for the first 5 to 7 days in medium containing a 1:1 mixture of bronchial epithelial cell growth medium (BEGM) (Cambrex) and DMEM with high glucose with supplement of growth factors (Krunkosky T M, Fischer B M, Martin L D, Jones N, Akley N J and Adler K B. (2000) *Am J Respir Cell Mol Biol* 22:685-692). When cultures are 70% confluent (days 5 to 7), the air-liquid interface is created by removing the apical medium and exposing cells only to medium on their basal surface. Cells are cultured for additional 14 days in air-liquid interphase, for a total of 21 days in culture, and are then ready for experiments. The differentiated epithelium can be maintained in vitro for weeks.

Epithelial morphology and degree of differentiation is documented by routine histology (Endo Y, Carroll K N, Ikizler M R and Wright P F. (1996) *J Virol* 70:2055-2058). Briefly, following fixation with 10% buffered formalin, the epithelial cells are embedded in paraffin, sectioned and stained with hematoxylin and eosin, and with periodic acid-Schiff stain for mucus secreting cells.

Influenza infection is carried out in the above two model systems by adding 0.001 to 1 MOI of viruses to the differentiated cells. The titer and infectivity of viruses in the supernatant are followed over a period of 3 to 7 days. The level of influenza viral amplification and the infectivity of influenza viruses are evaluated using conventional and modified plaque assays.

Example 3: Comparing Functions of the Aprotinin Fusion Proteins In Vitro

Anti-Viral Effects of Aprotinin Fusion Proteins
1. Pre-Infection Treatment.
Aprotinin fusion proteins are added to primary human cell cultures at various concentrations and allowed to incubate with the cells for 1 hour. The cells are washed with fresh medium and immediately inoculated with influenza viruses at MOI 0.01 to 1. Cells are washed again after 1 hour and cultured for 3 to 5 days. Titer and infectivity of viruses in the supernatant are measured at various time points by two plaque assays. The cytopathic effect caused by viral infection is evaluated by staining viable cells with crystal violet and quantifying by measuring absorption at 570 nm at the end of the experiment. The percentage of cell protection by aprotinin fusion proteins is calculated by 100× {(aprotinin treated sample-untreated infected sample)/(uninfected control-untreated infected sample)}. The drug efficacy for cell protection is described by its Effective Concentration that achieves 50% of the cell protection ($EC_{50}$). Since HA activation only occurs to newly released viral particles, the first round of viral infection occurs normally and viral titer rises in the first 24 hours after infection. However, starting from the second round, infectivity of viruses drops and viral titer gradually decreases as result of aprotinin treatment. Results from this experiment differentiate various types of different aprotinin fusion proteins by their efficacies in a single prophylactic treatment.

Alternatively, timing of initial viral inoculation is altered from immediately after aprotinin treatment to 2-24 hours post treatment. Viral titer, infectivity and cytopathic effect are measured for 3 to 5 day after infection as described above. Results from these experiments distinguish various aprotinin fusion proteins by the lengths of the effective window after a single prophylactic treatment.

2. Post-Infection Treatment.

For multi-dose treatment, cells are first infected by viral inoculations at 0.001 to 0.1 MOI for 1 hour. Various concentrations of aprotinin fusion proteins are added immediately afterwards, additional treatments are applied at 8-hour intervals during the first 48 hours post infection. Cells are cultured until day 7 post infection. Viral titer and infectivity in the media are followed during the whole process. Cytopathic effect is evaluated at the end of the experiment.

For single dose treatment, cells are first infected by viral inoculations at 0.001 to 0.1 MOI for 1 hour. Treatments of aprotinin fusion proteins at various concentrations are applied at different time points during the first 48 hours after infection, but each cell sample only receives one treatment during the whole experiment. Cells are cultured until day 7 post infection. Viral titer and infectivity in the media are followed during the whole process. Cytopathic effect is evaluated at the end of the experiment. Results from these experiments distinguish different types of aprotinin fusion proteins for their therapeutic potency.

Inhibition of HA Cleavage by Aprotinin Fusion Proteins

To demonstrate that aprotinin fusion proteins inhibit influenza viral infection by inhibiting cleavage of influenza HA protein, a human primary epithelial cell culture is infected with influenza virus at MOI of 1. Aprotinin fusion proteins are added to the culture either right before viral inoculation or immediately after the viral infection. At 6.5 hour post infection, the culture is incubated for 1 hour in MEM lacking cold methionine and containing $^{35}$S-labeled methionine (Amersham) at a concentration of 100 microCi/ml (pulse). Thereafter, the cells are washed twice with MEM containing a 10-fold concentration of cold methionine and incubated in MEM for additional 3 hours (chase). After labeling, cells are dissolved in radioimmunoprecipitation assay (RIPA) buffer, HA is precipitated by anti-serum against the particular strain of virus used for infection (anti-influenza sera can be obtained from ATCC and Center of Disease Control and Prevention), and the immunocomplex is then purified by protein G-Sepharose (Amersham). Samples are fractionated by SDS-PAGE followed by autoradiography. In samples untreated by aprotinin fusion proteins, HA1 and HA2 are expected to be the predominant HA species; while in aprotinin treated samples, HA0 is expected to be the major type of HA present.

Example 4: Synthesizing Genes of Five Sialidases, Expressing and Purifying the Sialidase Proteins Introduction Influenza viruses belong to the orthomyxoviridae family of RNA viruses. Both type A and type B viruses have 8 segmented negative-strand RNA genomes enclosed in a lipid envelope derived from the host cell. The viral envelope is covered with spikes that are composed of three proteins: hemagglutinin (HA), that attaches virus to host cell receptors and mediates fusion of viral and cellular membranes; neuraminidase (NA), which facilitates the release of the new viruses from the host cell; and a small number of M2 proteins that serve as ion channels. For Influenza A virus, HA and NA both undergo antigenic drift and antigenic shift, the viral subtypes are distinguished by serologic differences between their HA and NA proteins. There are total 15 types of HA (H1-H15) and 9 types of NA (N1-N9), but only three HA (H1-H3) and two NA (N1 and N2) have been found in human Influenza A virus so far (Granoff, A. & Webster, R. G., ed. *Encyclopedia of Virology*, $2^{nd}$ Edition, Vol 2). In contrast to Influenza A virus, no distinct antigenic subtypes are recognized for Influenza virus B.

While Influenza B virus circulates only in humans, Influenza A virus can be isolated from a whole host of animals, such as pigs, horses, chickens, ducks and other kinds of birds, which accounts for genetic reassortment of Influenza A virus that results in antigenic shift. Wild aquatic birds are considered to be the primordial reservoir of all influenza viruses for avian and mammalian species. There is extensive evidence for transmission of the virus between aquatic birds and other species including pigs and horses and indirect transmission to humans through pigs. Direct transmission from pigs or chickens to humans has also been documented (Ito, T. (2000) *Microbiol Immunol* 44(6):423-430).

The host cell receptor for influenza viruses is the cell surface sialic acid. Sialic acids are α-keto acids with 9-carbon backbones that are usually found at the outermost positions of the oligosaccharide chains that are attached to glycoproteins and glycolipids. One of the major types of sialic acids is N-acetylneuraminic acid (Neu5Ac), which is the biosynthetic precursor for most of the other types. Two major linkages between Neu5Ac and the penultimate galactose residues of carbohydrate side chains are found in nature, Neu5Ac α(2,3)-Gal and Neu5Ac α(2,6)-Gal. Both Neu5Ac α(2,3)-Gal and Neu5Ac α(2,6)-Gal molecules can be recognized by Influenza A virus as the receptor (Schauer, R. (1982) *Adv. Carbohydrate Chem & Biochem* 40:131-235), while human viruses seem to prefer Neu5Ac α(2,6)-Gal, avian and equine viruses predominantly recognize Neu5Ac α(2,3)-Gal (Ito, T. (2000) *Microbiol Immunol* 44(6):423-430).

Infections by influenza type A and B viruses are typically initiated at the mucosal surface of the upper respiratory tract. Viral replication is primarily limited to the upper respiratory tract but can extend to the lower respiratory tract and causes bronchopneumonia that can be fatal. The risk of death is one per 10,000 infections, but is significantly greater for high-risk groups with pre-existing cardiopulmonary conditions and for immunologically naïve individuals during a pandemic.

A therapeutic compound comprising a sialidase that can effectively degrade both receptor sialic acids, Neu5Ac α(2,6)-Gal and Neu5Ac α(2,3)-Gal, can confer protection against the broadest range of influenza viruses, including animal viruses. It can also remain effective as the viral strains change yearly. Because sialidase targets the host cell rather than virus and acts at the "choking point" in a viral life cycle, generation of resistant virus is improbable. Protein-bound sialic acid turns over homogeneously on cell surface with half-life of 33 hours (Kreisel, W, Volk, B A, Buchsel, R. and Reutter, W. (1980) *Proc Natl Acad Sci USA* 77:1828-1831). Therefore we estimate that once-a-day or twice-a-day administration of a sialidase would confer sufficient protection against influenza.

Sialidases are found in higher eukaryotes, as well as in some mostly pathogenic microbes, including viruses, bacteria and protozoans. Viral and bacterial sialidases have been well characterized, and the three-dimensional structures of some of them have been determined (Crennell, S J, Garman, E, Laver, G, Vimr, E and Taylor, G. (1994) *Structure* 2:535-544; Janakiraman, M N, White, C L, Laver, W G, Air, G M and Luo, M. (1994) *Biochemistry* 33:8172-8179; Pshezhetsky, A, Richard, C, Michaud, L, Igdoura, S, Wang, S, Elsliger, M, Qu, J, Leclerc, D, Gravel, R, Dallaire, L and Potier, M. (1997) *Nature Genet* 15: 316-320). Several human sialidases have also been cloned in the recent years (Milner, C M, Smith, S V, Carrillo M B, Taylor, G L, Hollinshead, M and Campbell, R D. (1997) *J Bio Chem* 272:4549-4558; Monti, E, Preti, A, Nesti, C, Ballabio, A and Borsani G. 1999. *Glycobiol* 9:1313-1321; Wada, T, Yoshikawa, Y, Tokuyama, S, Kuwabara, M, Akita, H and Miyagi, T. (1999) *Biochem Biophy Res Communi* 261:21-27; Monti, E, Bassi, M T, Papini, N, Riboni, M, Manzoni, M, Veneranodo, B, Croci, G, Preti, A, Ballabio, A, Tettamanti, G and Borsani, G. (2000) *Bichem J* 349:343-351). All the sialidases characterized share a four amino acid motif in the amino terminal portion followed by the Asp box motif which is repeated three to five times depending on the protein. (Monti, E, Bassi, M T, Papini, N, Riboni, M, Manzoni, M, Veneranodo, B, Croci, G, Preti, A, Ballabio, A, Tettamanti, G and Borsani, G. (2000) *Bichem J* 349:343-351; Copley, R R, Russell, R B and Ponting, C P. (2001) *Protein Sci* 10:285-292). While the overall amino acid identity of the sialidase superfamily is relatively low at about 20-30%, the overall fold of the molecules, especially the catalytic amino acids, are remarkably similar (Wada, T, Yoshikawa, Y, Tokuyama, S, Kuwabara, M, Akita, H and Miyagi, T. (1999) *Biochem Biophy Res Communi* 261:21-27; Monti, E, Bassi, M T, Papini, N, Riboni, M, Manzoni, M, Veneranodo, B, Croci, G, Preti, A, Ballabio, A, Tettamanti, G and Borsani, G. (2000) *Bichem J* 349:343-351; Copley, R R, Russell, R B and Ponting, C P. (2001) *Protein Sci* 10:285-292).

The sialidases are generally divided into two families: "small" sialidases have molecular weight of about 42 kDa and do not require divalent metal ion for maximal activity; "large" sialidases have molecular weight above 65 kDa and may require divalent metal ion for activity (Wada, T, Yoshikawa, Y, Tokuyama, S, Kuwabara, M, Akita, H and Miyagi, T. (1999) *Biochem Biophy Res Communi* 261:21-27; Monti, E, Bassi, M T, Papini, N, Riboni, M, Manzoni, M, Veneranodo, B, Croci, G, Preti, A, Ballabio, A, Tettamanti, G and Borsani, G. (2000) *Bichem J* 349:343-351; Copley, R R, Russell, R B and Ponting, C P. (2001) *Protein Sci* 10:285-292).

Over fifteen sialidase proteins have been purified and they vary greatly from one another in substrate specificities and enzymatic kinetics. To confer a broad-spectrum protection against influenza viruses, a sialidase needs to effectively degrade sialic acid in both α(2,6)-Gal and α(2,3)-Gal linkages and in the context of glycoproteins and some glycolipids. Viral sialidases, such as those from influenza A virus, fowl plague virus and Newcastle disease virus, are generally specific for Neu5Ac α(2,3)-Gal and only degrade Neu5Ac α(2,6)-Gal very inefficiently. Small bacterial sialidases generally react poorly to sialic acid in the context of glycoproteins and glycolipids. By contrast, large bacterial sialidases can effectively cleave sialic acid in both (α,2-6) linkage and (α,2-3) linkage in the context of most natural substrates (FIG. 4; Vimr, D R. (1994) *Trends Microbiol* 2: 271-277; Drzeniek, R. (1973) *Histochem J* 5:271-290; Roggentin, P, Kleineidam, R G and Schauer, R. (1995) *Biol Chem Hoppe-Seyler* 376:569-575; Roggentin, P, Schauer, R, Hoyer, L L and Vimr, E R. (1993) *Mol Microb* 9:915-921). Because of their broad substrate specificities, large bacterial sialidases are better candidates.

Among the large bacterial sialidases with known substrate specificity shown in FIG. 4, *Vibrio cholerae* sialidase requires Ca2+ for activity making it less preferred. More preferred sialidases include the 71 kDa enzyme from *Clostridium perfringens*, the 113 kDa enzyme from *Actinomyces viscosus* and sialidase of *Arthrobacter ureafaciens*. A third sialidase, the 68 kDa enzyme from *Micromonospora viridifaciens*, has been known to destroy influenza viral receptor (Air, G M and Laver, W G. (1995) *Virology* 211:278-284), and is also a candidate.

These enzymes have high specific activity (600 U/mg protein for *C. perfringens* (Corfield, A P, Veh, R W, Wember, M, Michalski, J C and Schauer, R. (1981) *Bichem J* 197: 293-299) and 680 U/mg protein for *A. viscosus* (Teufel, M, Roggentin, P. and Schauer, R. (1989) *Biol Chem Hoppe Seyler* 370:435-443)), are fully active without divalent metal iron, and have been cloned and purified as recombinant proteins from *E. coli* (Roggentin, P, Kleineidam, R G and Schauer, R. (1995) *Biol Chem Hoppe-Seyler* 376:569-575, Teufel, M, Roggentin, P. and Schauer, R. (1989) *Biol Chem Hoppe Seyler* 370:435-443, Sakurada, K, Ohta, T and Hasegawa, M. (1992) *J Bacteriol* 174: 6896-6903). In addition, *C. perfringens* is stable in solution at 2-8° C. for several weeks, and at 4° C. in the presence of albumin for more than two years (Wang, F Z, Akula, S M, Pramod, N P, Zeng, L and Chandran, B. (2001) *J Virol* 75:7517-27). *A. viscosus* is labile towards freezing and thawing, but is stable at 4° C. in 0.1 M acetate buffer, pH 5 (Teufel, M, Roggentin, P. and Schauer, R. (1989) *Biol Chem Hoppe Seyler* 370:435-443).

Although the chances of inducing immune reactions using bacterial sialidases is very low because the proteins will be used topically in the upper respiratory tract and will not be absorbed systemically, a human enzyme would be more desirable for long-term use in human subjects.

Four sialidase genes have been cloned from human so far: NEU1/G9/lysosomal sialidase (Pshezhetsky, A, Richard, C, Michaud, L, Igdoura, S, Wang, S, Elsliger, M, Qu, J, Leclerc, D, Gravel, R, Dallaire, L and Potier, M. (1997) *Nature Genet* 15: 316-320.

Milner, C M, Smith, S V, Carrillo M B, Taylor, G L, Hollinshead, M and Campbell, R D. (1997). *J Bio Chem* 272:4549-4558); NEU3, a membrane-associated sialidase isolated from human brain (Wada, T, Yoshikawa, Y, Tokuyama, S, Kuwabara, M, Akita, H and Miyagi, T. (1999) *Biochem Biophy Res Communi* 261:21-27, Monti, E, Bassi, M T, Papini, N, Riboni, M, Manzoni, M, Veneranodo, B, Croci, G, Preti, A, Ballabio, A, Tettamanti, G and Borsani, G. (2000) *Bichem J* 349:343-351), NEU2 a 42 kDa sialidase expressed in human skeletal muscle at a very low level (Monti, E, Preti, A, Nesti, C, Ballabio, A and Borsani G. (1999) *Glycobiol* 9:1313-1321), and NEU4 a 497 amino acid protein (Genbank NM080741) expressed in all human tissues examined (Monti, E, Preti, A, Venerando, B and Borsani, G. (2002) *Neurochem Res* 27:646-663).

Amino acid sequence comparison reveals NEU2 (SEQ ID NO:8) and NEU4 (SEQ ID NO:9) are both cytosolic sialidases. 9 out of 12 of the amino acid residues which form the catalytic site of *S. typhimurium* sialidase are conserved in both NEU2 and NEU4 (Monti, E, Preti, A, Nesti, C, Ballabio, A and Borsani G. (1999) *Glycobiol* 9:1313-1321, FIG. 3). In addition, NEU4 also shows a stretch of about 80 amino acid residues (aa 294-373) that appears unique among known mammalian sialidases (Monti, E, Preti, A, Venerando, B and Borsani, G. (2002) *Neurochem Res* 27:646-663). Unlike the selected large bacterial sialidases, the substrate specificity of NEU2 and NEU4 is unknown. It will need to be tested if NEU2 and NEU4 can effectively degrade the influenza virus receptors.

Sialidase Assay

NEU2, NEU4 and *M. viridifaciens* enzymes will be stored in PBS and 50% glycerol at −20° C. *C. perfringens* and *A. viscosus* enzymes are stored in 10 mM acetate buffer (pH5) at 4° C. Protein preps are characterized by HPLC and SDS-PAGE electrophoresis. Specific activities and stability of the enzymes will be monitored by sialidase assay.

The enzymatic activity of sialidases are determined by fluorimetric 2'-(4-methylumbelliferyl)-alpha-D-N-acetylneuraminic acid) (4Mu-NANA) (Sigma) as the substrate. Specifically, reactions are set up in duplicate in 0.1M Na citrate/phosphate buffer pH5.6, in the presence of 400 micrograms bovine serum albumin, with 0.2 mM 4MU-NANA in a final volume of 100 microliters, and incubated at 37° C. for 5-10 min. Reactions are stopped by addition of 1 ml of 0.2 M glycines/NaOH pH10.2. Fluorescence emission is measured on a fluorometer with excitation at 365 nm and emission at 445 nm, using 4-methylumbelliferone (4-MU) to obtain a calibration curve.

Example 5: Comparing Functions of the Sialidases In Vitro and Selecting One Sialidase for Further Studies 1. Stocks of Influenza Viruses Influenza viral strains are obtained from the ATCC and the repository at St. Jude Children's Research Hospital. Viral stocks are grown on Madin-Darby canine kidney (MDCK) cells in minimal essential medium (MEM) supplemented with 0.3% bovine serum albumin and 0.5 micrograms of trypsin per ml. After incubating for 48 to 72 hours, the culture medium is clarified by low speed centrifugation. Viral particles are pelleted by ultracentrifugation through a 25% sucrose cushion. Purified viruses are suspended in 50% glycerol-0.1M Tris buffer (pH 7.3) and stored at −20° C. Viral titer is determined by plaque assay (Tobita, K, Sugiura, A, Enomoto, C and Furuyama, M. (1975) *Med Microbiol Immnuol* 162: 9-14), or $TCID_{50}$, which is the dose of virus required to infect 50% of the MDCK cells.

Selected human and animal influenza A strains with specificity towards Neu5Ac alpha(2,6)-Gal or Neu5Ac alpha(2,3)-Gal and have high affinity to the receptors (measured by high hemagglutination activity) are chosen for in vitro tests:

1. Strains that recognize receptor Neu5Ac alpha(2,6)-Gal include human isolates A/aichi/2/68, A/Udorn/307/72, A/Prot Chaimers/1/73 and A/Victoria/3/75, etc. (Connor, R J, Kawaoka, Y, Webster, R G and Paulson J C. (1994) *Virology* 205:17-23).
2. Strains that have Neu5Ac alpha(2,3)-Gal specificity include animal isolates A/duckUkraine/1/63, A/duck-Memphis/928/74, A/duckhokk/5/77, A/Eq/Miami/1/63, A/Eq/Ur/1/63, A/Eq/Tokyo/71, A/Eq/Prague/71, etc (Connor, R J, Kawaoka, Y, Webster, R G and Paulson J C. (1994) *Virology* 205:17-23).

2. Hemagglutination Assay

This assay is used to rapidly determine the efficiency of each enzyme to destroy receptors Neu5Ac alpha(2,6)-Gal and Neu5Ac alpha(2,3)-Gal.

Specifically, 6 ml of Chicken red blood cells (SPAFAS Inc., Norwich, Conn.) are diluted in two times the volume of PBS, centrifuge for 5 min at 500×g and re-suspended in PBS of original volume. Sialidases are added to the chicken erythrocytes at various concentrations and allowed to incubate at room temperature for 30 min. The cells are then washed three times to remove sialidase proteins, and then are resuspended in PBS to 6 ml. Control cells are incubated with BSA and washed. Various strains of influenza virus, which recognize either Neu5Ac alpha(2,6)-Gal or Neu5Ac alpha(2,3)-Gal as the receptor as listed above, are prepared in microtiter plates as serial dilutions in PBS (100 microliters) of the original viral stocks. Sialidase-treated or control chicken red blood cell suspensions (100 microliters of the 0.5% solution prepared above) are added to each well at 4° C. The plates are read after 2 h. The lowest concentration of virus that causes the blood cell to agglutinate is defined as one hemagglutination unit. We will be looking for enzymes that effectively abolish hemagglutination by all viral strains.

3. Viral Inhibition Assay

Confluent monolayers of MDCK cells are treated with various concentrations of sialidases for 1 h, washed twice with buffer, then infected with various strains of influenza virus. After incubation for 1 hr, the cells are washed again to remove unbound virus. To estimate the decrease in viral binding sites on cell surface, the cells are overlaid with agar and incubated at 37° C. The number of plaques in the sialidase treated cells will be compared against those in control cells. Alternatively, the cells will be cultured in regular medium at 37° C., and viral titers in the culture media are measured at various time during culture as $TCID_{50}$.

To demonstrate that sialidase treatment can inhibit a pre-existing infection, MDCK monolayers are first infected with a low titer of virus. After washing off the unbound virus, the cells are then cultured in the presence of a sialidase. Fresh sialidase is added to cell culture very 24 h. Viral titer in the cultured medium is measured over a 72-hour period.

4. Cytotoxicity Assay

Primary human bronchial epithelial cells are purchased (Clonetics) and cultured in supplemented minimal medium following manufacture's instruction. Sialidases are added to the culture medium at various concentrations. Cell growth over a period of 7-10 days will be measured. Cells will also be observed regularly for microscopic cytopathic effects.

Example 6: Constructing and Testing Sialidase Fusion Proteins

1. Choosing a GAG-Binding Sequence as the Anchoring Domain.

One sialidase is selected for its best overall properties, including anti-viral activity, toxicity, stability, ease of production, etc. We will then genetically link it to a GAG-binding sequence, sub-clone the fusion genes into pQE vector, express and purify the fusion proteins from *E. coli*.

We have selected six possible human GAG-binding sequences: PF4 (aa 47-70) (SEQ ID NO:2), IL-8 (aa 46-72) (SEQ ID NO:3), AT III (aa 118-151) (SEQ ID NO:4), ApoE (aa 132-165) (SEQ ID NO:5), human angio-associated migratory cell protein (AAMP) (aa 14-25) (SEQ ID NO:6), and amphiregulin (AR) (aa 125-145) (SEQ ID NO:7) (FIG. 2). These sequences generally bind to heparin with nanomolar-level affinities; however, their affinities may vary from one another by an order of magnitude (Table 1). Since it is not clear which anchoring domain will enable the most effective functioning of the sialidase, all four GAG-binding sequences are fused with the sialidase gene either on the N terminus or the C terminus via a generic linker sequence GGGGS as the following constructs:

```
(GAG binding domain-GGGGS (SEQ ID NO: 10)-
Sialidase);
or
(Sialidase-GGGGS (SEQ ID NO: 10)-GAG binding
domain)
```

Different fusion proteins are compared by a modified viral inhibition assay. Specifically, confluent monolayers of MDCK cells are treated with same amount of each fusion protein for a limited duration, such as 30 min. The cells are then washed twice with buffer to remove unbound sialidase fusion proteins, and incubated in culture medium for an additional 1 hour. Afterwards, strains of influenza virus are added to the cells for 1 hr and then cells are washed again to remove unbound virus. Viral titers in the culture media are measured during 72-h cultures as $TCID_{50}$. The un-fused sialidase protein will be used to compare against the fusion proteins in this assay. If the results are too close to rank all fusion proteins, we will make the assay more stringent by shortening treatment window for the fusion proteins, lowering protein concentrations and increasing the level of viral challenge.

2. Optimizing the Fusion Protein Construct

After selecting the best fusion protein from the earlier experiments, the construct is further optimized by testing different linker length. In this regard, the following constructs are made:

```
(Sialidase-(GGGGS(SEQ ID NO:10))n (n=0, 1, 2, 3, or
4)-GAG binding domain)
```

The proteins are expressed and purified and compared in the modified viral protection assay as described above.

In addition, if earlier data indicate that higher affinity of the fusion protein towards heparan sulfate brings better potency, we also plan to test if the potency can be further improved by increasing the GAG-binding affinity. This can be achieved by creating a multivalent GAG binding mechanism in the fusion protein in constructs like these:

```
(Sialidase-(GGGGS (SEQ ID NO: 10))n-HS binding
domain-GAG binding domain);
or:
(GAG binding domain-(GGGGS (SEQ ID NO: 10))n-
Sialidase-(GGGGS (SEQ ID NO: 10))n-GAG binding
domain)
```

The purified fusion proteins are ranked based on their activities in the modified viral protection assay as described above.

3. Cytotoxicity Assay

The effects of the fusion proteins on normal cell growth and morphology are monitored by culturing primary human bronchial epithelial cells with various concentrations of the fusion proteins and following growth curve of the cells and observing any microscopic cytopathic effects.

Example 7: Fusion Proteins Against Other Infectious Microbes

Fusion proteins composed of a functional domain and an anchorage domain are designed for many more different applications. For example, a sialidase fusion protein as proposed here can also be used as a therapeutic/prophylactic agent against infections by other viruses and bacteria besides influenza viruses, because many other infectious microbes, such as paramyxoviruses (Wassilewa, L. (1977) *Arch Virol* 54:299-305), coronaviruses (Vlasak, R., Luytjes, W., Spaan, W. and Palese, P. (1988) *Proc Natl Acad Sci USA* 85:4526-4529), rotaviruses (Fukudome, K., Yoshie, O. and Konno, T. (1989) *Virology* 172:196-205) and *Pseudomonas aeruginosa* (Ramphal, R. and Pyle, M. (1983) *Infect Immun* 41:339-44) etc, are also known to use sialic acid as cellular receptors. For example, aprotinin fused with a heparin-binding domain can make a fusion protein that be used to prevent/treat infection of other viruses besides influenza that require host serine proteases for activation, such as parainfluenza virus.

Example 8: Cloning Sialidase Catalytic Domain Fusion Proteins

According to the published literature on the large bacterial sialidases, the 51 kDa *Arthrobacter ureafaciens* sialidase, the 71 kDa sialidase from *Clostridium perfringens* and the 113 kDa sialidase from *Actinomyces viscosus* seem to have similar specific activities and broad substrate specificity toward various sialic acid conjugates (Biology of the Sialic Acids (1995), 270-273; Corfield et al., Biochem. J., (1981) 197(2), 293-299; Roggentin et al., Biol. Chem. Hoppe Seyler, (1995) 376(9), 569-575; Teufel et al., Biol. Chem. Hoppe Seyler, (1989) 370(5), 435-443). A third sialidase, the 68 kDa enzyme from *Micromonospora viridifaciens*, was also known to destroy the influenza viral receptor (Air and Laver, Virology, (1995) 211(1), 278-284; (1995), 270-273).

*A. viscosus* is part of the normal flora of human oral cavity and gastrointestinal tract (Sutter, Rev. Infect. Dis., (1984) 6 Suppl 1, S62-S66). Since the sialidase from *A. viscosus* is normally secreted by the bacterium hosted on human mucosal surface, it should be tolerated by the human mucosal immune system. Therefore, it is unlikely that *A. viscosus* sialidase will be immunogenic when delivered topically to the human airway surface. We think that this feature makes *A. viscosus* sialidase a good candidate for a therapeutic agent.

We determined that a fragment of the *A. viscosus* sialidase, extending from amino acid 274 to amino acid 667, should contain the catalytic domain (referred to as AvCD) of the sialidase and should be fully active on it own. We later cloned the AvCD fragment and demonstrated that this AvCD fragment and other *A. viscosus* sialidase fragments comprising at least amino acids 290-666 of the *A. viscosus* sialidase protein sequence (SEQ ID NO:12), such as the fragment extending from amino acid 274 to amino acid 681, the fragment extending from amino acid 274 to amino acid 666, the fragment extending from amino acid 290 to amino acid 666, and the fragment extending from amino acid 290 to amino acid 681, have sialidase activity.

The complete sequence of the *A. viscosus* sialidase protein and gene are set forth in SEQ ID NOS: 11 and 12, respectively. Based on homology with sialidases with known 3D structures (*M. viridifaciens* and *S. typhimurium*), we assigned the catalytic domain (CD) sequence to be located between amino acids 274-667 (SEQ ID NO:16). To clone the catalytic domain of *A. viscosus* sialidase (AvCD), this region of the *A. viscosus* sialidase gene was engineered with codons optimized for expression in *E. coli* (SEQ ID NO:15). The codon-optimized AvCD nucleotide sequence encoding amino acids 274-667 of the *A. viscosus* sialidase (SEQ ID NO:15) was produced by chemical synthesis of overlapping oligonucleotides which were annealed, amplified by PCR and cloned into the expression vector pTrc99a (Amersham, N.J., USA).

Sialidase fusion constructs were made using standard molecular cloning methods. The His$_6$-AvCD construct was made by fusing six histidines (His$_6$) to the N-terminal residue of the AvCD sequence. The His$_6$-AvCD construct has the nucleotide sequence of SEQ ID NO:28 and translated amino acid sequence of SEQ ID NO:29. These sequences are depicted in FIG. 5.

To make the AR-AvCD construct, an anchoring domain was directly fused with the N-terminal residue of the AvCD sequence. The anchoring domain, referred to as AR, was derived from the GAG binding sequence of human amphiregulin precursor (GenBank # AAH09799). Nucleotide sequences encoding amino acids 125 to 145 (FIG. 2, SEQ ID NO:7) of the human amphiregulin precursor were synthesized chemically as two overlapping oligonucleotides. The AR-AvCD construct has the nucleotide sequence of SEQ ID NO:18 and translated amino acid sequence of SEQ ID NO:19.

Another construct, AR-G$_4$S-AvCD, was made by fusing the same AR-encoding sequence used in the AR-AvCD construct with a sequence encoding a five-amino-acid linker (GGGGS; SEQ ID NO:10) which then was fused with the AvCD sequence such that in a translation product, the linker was fused to N-terminus of the catalytic domain of the *A. viscosus* sialidase. The nucleotide sequence (SEQ ID NO:36) and translated amino acid sequence (SEQ ID NO:37) of this construct are depicted in FIG. 7. All constructs were cloned into the pTrc99a expression vector.

In addition, four constructs were made in which the catalytic domain of the *A. viscosus* sialidase was fused to the N-terminus of the AR (GAG-binding domain of human amphiregulin; SEQ ID NO:7). In Construct #4 (SEQ ID NO:21), the catalytic domain of the *A. viscosus* sialidase consisted of amino acids 274-666 of SEQ ID NO:12 fused to the GAG-binding domain of amphiregulin (SEQ ID NO:7). In Construct #5 (SEQ ID NO:23), the catalytic domain of the *A. viscosus* sialidase consisted of amino acids 274-681 of SEQ ID NO:12 fused to the GAG-binding domain of amphiregulin (SEQ ID NO:7). In Construct #6 (SEQ ID NO:25), the catalytic domain of the *A. viscosus* sialidase consisted of amino acids 290-666 of SEQ ID NO:12 fused to the GAG-binding domain of amphiregulin (SEQ ID NO:7). In Construct #7 (SEQ ID NO:27), the catalytic domain of the *A. viscosus* sialidase consisted of amino acids 290-681 of SEQ ID NO:12 fused to the GAG-binding domain of amphiregulin (SEQ ID NO:7). All of these constructs displayed comparable sialidase activity in assays.

Example 9: Production of Sialidase Catalytic Domain Fusion Proteins

To produce the sialidase fusion proteins, the expression constructs were transformed into *E. coli* BL21. A single colony was inoculated into 2.5 ml of LB broth and grown overnight at 37° C. with shaking. In the morning 2 ml of overnight culture was inoculated into 500 ml of TB medium in a 2 liter shake flask and the culture was allowed to grow to $OD_{600}$=4.0 (2-4 hours) at 37° C. with shaking Protein expression was induced by addition of IPTG to a final concentration of 1 mM and continued for 3 hr with shaking Cells were harvested by centrifugation at 5,000×g for 10 min. Cell were washed once (resuspended in PBS and recentrifuged) and resuspended in 15 ml of Lysis buffer. Compositions of media and buffers used in protein expression and purification. TB medium for protein expression Solution 1
Bacto-tryptone—12 g
Yeast extract—24 g
$H_2O$ to 800 ml
Solution 2
$KH_2PO_4$ (anhydrous)—2.3 g
$K_2HPO_4$ (anhydrous)—12.5 g
$H_2O$ to 100 ml
Autoclave Solutions 1 and 2 Separately, Cool, Mix and Add the Following:
60 ml of 20% glycerol (filter sterilized)
20 ml of 20% glucose (filter sterilized)
Lysis Buffer
50 mM phosphate, pH 8.0
10% glycerol
300 mM NaCl Bacterial cells suspended in lysis buffer were lysed by sonication and cell debris was removed by centrifugation. Clarified lysate was passed through an SP-Sepharose column (bed volume 15 ml, flow rate 120 cm/hour). The column was reconditioned to lower pH and salt with one volume of PBS to ensure good retention of Fludase during endotoxin removal. Endotoxin was removed by washing the column with 5 volumes of PBS containing 1% Triton X-100, 0.5% Sodium Deoxycholate and 0.1% SDS. The detergents were washed away with 3 volumes of PBS and 3 volumes of lysis buffer. Proteins were eluted from the column with lysis buffer that contained 0.8 M NaCl. The fraction eluted from SP-Sepharose was adjusted to 1.9 M $(NH_4)_2SO_4$ (most contaminating proteins are salted out at this step) and clarified by centrifugation. The supernatant was loaded onto Butyl-Sepharose column (flow rate 120 cm/hour). The column was washed with 2 volumes of 1.3 M $(NH_4)_2SO_4$ and the fusion was eluted with 0.65 M $(NH_4)_2SO_4$. For the final step, size exclusion chromatography was performed on Sephacryl S-200 equilibrated with PBS buffer at a flow rate of 25 cm/hour. Sialidase activity was determined against 4-MU-NANA as described in the following paragraph. Protein concentration was determined using Bio-Rad's Bradford kit. Protein purity was assessed by SDS-PAGE and estimated to be >98%. Specific activity of the enzyme was about 937 U/mg. Endotoxin in final preparations was measured using LAL test (Cambrex) and estimated to be <0.5 EU/ml.

For purification of His6 containing fusion protein, cation exchange on SP-Sepharose was replaced with Metal Chelate Affinity Chromatography on Ni-NTA. All buffers remained the same with the exception that elution from Ni-NTA was performed by 0.25 M imidazole in lysis buffer.

Example 10: Sialidase Assay to Measure Activity of Sialidase Catalytic Domain Fusion Proteins The sialidase activity of the AR-AvCD protein encoded by Construct #2 was assayed and compared with that of native sialidases purified from C. perfringens (Sigma, St. Louis, Mo.) and A. ureafaciens (Prozyme, San Leandro, Calif.). In addition, a fusion protein produced from a construct in which the amphiregulin GAG sequence (SEQ ID NO: 7) was fused to the Neu 2 human sialidase (SEQ ID NO:8) was also assayed for sialidase activity.

The sialidase activity expressed as units per mg sialidase was measured by the sialidase assay using the artificial fluorogenic substrate 4-MU-NANA (Sigma). One unit of sialidase is defined as the amount of enzyme that releases 10 nmol of MU from 4-MU-NANA in 10 min at 37° C. (50 mM $CH_3COOH$—NaOH buffer, pH 5.5) in reaction that contains 20 nmol of 4-MU-NANA in a 0.2 ml volume. Reactions are stopped by addition of 1 ml of 0.2 M glycine/NaOH pH 10.2. Fluorescence emission is measured on a fluorometer with excitation at 365 nm and emission at 445 nm, using 4-methylumbelliferone (4-MU) to obtain a calibration curve (Potier et al., Anal. Biochem., (1979) 94(2), 287-296).

TABLE 2

Specific activity of sialidases (units per mg).

| Sialidase | Specific activity |
| --- | --- |
| AR-NEU2 | 8 |
| AR-AvCD | 937 |
| C. perfringens | 333 |
| A. ureafaciens | 82 |

Our results show that the AvCD fusion protein (AR-AvCD) has the highest specific activity among all the tested sialidases (Table 2). The specific activity of AR-AvCD is over 100 times higher than that of a human sialidase fusion (AR-NEU2), and over two times higher than that of C. perfringens sialidase. Experimental results comparing the stability of the sialidases indicate very high stability of AR-AvCD: No loss of activity for AR-AvCD was detected after 20 weeks at 25° C. or 4° C. in solution. By comparison, AR-NEU2 solution exhibited a half-life of 5 and 2 weeks when stored at 25° C. and 37° C., respectively.

Example 11: Optimization of the N-Terminus of Sialidase Catalytic Domain Fusion Proteins The N-terminus of the AR-AvCD fusion protein was partially cleaved under certain conditions that resulted in small degrees of protein heterogeneity in the purified AR-AvCD prep. To solve this problem, we designed an approach to optimize the N-terminus of the sialidase fusion construct. A library containing AR-AvCD with random amino acids at the N-terminus was constructed as follows. AR-AvCD was amplified by PCR using a primer pair in which the primer annealing on 5'-end of the gene contained a randomized sequence in positions corresponding to amino acids 2 and 3. The nucleotide sequence of the primer and the encoded amino acid sequence are shown below.

```
                                       (SEQ ID NO: 32)
ttttcgtctcccatgvnnvnnaagcgcaaaaaaaaaggcggca (SEQ ID NO: 33)
MetXxxXxxLysArgLysLysLysGlyGly
```

In SEQ ID NO:32, "n" stands for any nucleotide (a, c, g, or t) and "v" stands for nucleotides a, g or c. By designing the sequence in such a way (disallowing the nucleotide t in the first position of codons) we avoided introduction of stop codons as well as aromatic amino acids (Phe, Tyr, Trp) and Cys. The Esp3I restriction endonuclease site (shown in bold) was introduced to allow generation of NcoI compatible overhang. The primer annealing to 3'-end of the gene carried HindIII site following the stop codon. The PCR product was digested with Esp3I-HindIII was ligated into pTrc99a expression vector digested with NcoI-HindIII. The ligation mix was transformed into E. coli and the cells were grown overnight in liquid culture containing Ampicillin.

The next day the culture was diluted with fresh medium, grown to $OD_{600=0.8}$ and induced with IPTG for 2 hours. Cells were harvested, homogenized and the fusions were subjected to two-step purification by liquid chromatography. Clarified lysate was loaded onto SP-Sepharose equilibrated with lysis buffer (50 mM HEPES, pH 8.0, 0.3 M NaCl, 10% glycerol). The column was washed with 0.45 M NaCl and the fusions were eluted with 0.9 M NaCl. The eluate was diluted with 10% glycerol to bring the concentration of NaCl to 0.2 M and loaded onto Heparin-Sepharose column. The column was developed with a linear gradient of NaCl. The fractions that contained sialidase activity were resolved on SDS-PAGE, electroblotted onto PVDF membrane and the 43 kDa band was subjected to amino-terminal sequencing.

The predominant N-terminal residues of the isolated sialidase fusion protein were either Val or Gly followed by the N-terminal residues of the AR tag. We then synthesized new sialidase fusion constructs, Constructs #2 and #3, by introducing a Val in front of the AR sequence such that the first six amino acids encoded by Constructs #2 and #3 were (Met-Val-Lys-Arg-Lys-Lys (SEQ ID NO:17)). N-terminal sequencing of proteins made from these new fusion constructs showed 100% homogeneity with the initiation Met being completely removed (which is desirable for therapeutic proteins) and Val being the first N-terminal residue followed by the AR tag sequence. These data are consistent with earlier publications that reported the common rules of N-terminal processing and protein stability as function of protein's N-terminal amino acid residue (Hirel et al., Proc. Natl. Acad. Sci. U.S.A, (1989) 86(21), 8247-8251; Varshaysky, Proc. Natl. Acad. Sci. U.S.A, (1996) 93(22), 12142-12149).

The nucleotide sequences of new fusion Construct #2 (AR-AvCD with optimized N-terminus) (SEQ ID NO:18) and its amino acid sequence translation (SEQ ID NO:19) is depicted in FIG. 6. The nucleotide sequences of new fusion Construct #3 (AR-$G_4$S-AvCD with optimized N-terminus)

(SEQ ID NO:36) and its amino acid sequence translation (SEQ ID NO:37) is depicted in FIG. 7. The amino acid sequence of processed proteins isolated from *E. coli* infected with Construct #2 is provided herein as SEQ ID NO:38 and the amino acid sequence of processed proteins isolated from *E. coli* infected with Construct #3 is provided herein as SEQ ID NO:39.

Example 12: Comparing Activities of Sialidase Constructs with or without an Anchoring Domain To evaluate if the AR sequence indeed improves the cell-surface activity of a sialidase fusion protein, we incubated proteins purified from *E. coli* that were transformed with Construct #2; SEQ ID NO:18, depicted in FIG. 6) or Construct #1 (His$_6$-AvCD; SEQ ID NO:28, depicted in FIG. 5) with primary human bronchial epithelial cells and measured cell-bound sialidase activity after extensive washing. For cells incubated with Construct #2 protein (SEQ ID NO:19), up to 10% of the sialidase was found to be cell-bound, and the cell-bound sialidase activity increased in a dose-dependent manner with the input concentration of Construct #2 protein. However, Construct #1 protein (SEQ ID NO:29) incubated cells only exhibited background level of sialidase activity. Furthermore, we treated MDCK cells with either Construct #2 protein or Construct #1 protein and measured the level of residual α(2,6)-linked sialic acid on the surface of the cells (FIG. 8). At equal levels of enzymatic activity below 100 mU per well, Construct #2 protein demonstrated significantly higher potency than Construct #1 protein. These results indicate that the AR domain indeed enhances the function of sialidase.

Example 13: In Vitro Activities of Sialidase Fusion Proteins

Stocks of Influenza Viruses

Influenza viral strains are obtained from ATCC and the repository at St. Jude Children's Research Hospital. All experiments involving influenza viruses are conducted at Bio-safety level II.

Viruses are propagated on Madin-Darby canine kidney (MDCK) cells in minimal essential medium (MEM) supplemented with 0.3% bovine serum albumin and 0.5 micrograms of trypsin per ml. After incubating for 48 to 72 hours, the culture medium is clarified by low speed centrifugation. Viral particles are pelleted by ultracentrifugation through a 25% sucrose cushion. Purified viruses are suspended in 50% glycerol-0.1M Tris buffer (pH 7.3) and stored at −20° C.

1. Cell Protection Assay

To evaluate the ability of the Construct #2 AR-AvCD protein to protect cells against influenza viruses, we first treated MDCK cells with AR-AvCD made from Construct #2 or a broad-spectrum bacterial sialidase isolated from *A. ureafaciens*, and challenged the cells with a broad selection of human influenza viruses (IFV), including human IFV A of H1, H2 and H3 subtypes, human IFV B as well as an avian IFV strain. As shown in FIG. 9, the fusion protein made from Construct #2 demonstrated 80 to 100% of cell protection that was comparable to the effect of *A. ureafaciens* sialidase.

To perform the assay, MDCK cells were treated with 10 mU of AR-AvCD protein (made using Construct #2) or the isolated sialidase of *A. ureafaciens* at 37° C. for 2 hrs. The cells were subsequently challenged with influenza viruses at MOI 0.1 for 1 hr. The cells were washed and incubated in fresh DMDM:F12 supplemented with 0.2% ITS (GIBCO) and 0.6 μg/ml acetylated trypsin (Sigma). The cells were stained with 0.5% crystal violet and 20% methanol for 5 min and rinsed with tap water. The level of viable cells in each well was quantitated by extracting crystal violet by 70% ethanol and reading at 570 nM. Cell protection was calculated by 100×{(sialidase treated sample−virus only)/(uninfected sample-virus only)}.

IFV Inhibition Assay

We evaluated inhibition of IFV amplification by AR-AvCD protein (made using Construct #2) and AR-$G_4$S-AvCD protein (made using Construct #3) using a cell-based ELISA method (Belshe et al., J Virol., (1988) 62(5), 1508-1512).

To perform the assay, MDCK monolayers in 96 well plates were treated with 16 mU of the sialidases AR-AvCD made from Construct #2 or AR-$G_4$S-AvCD made from Construct #3 in EDB/BSA buffer (10 mM Sodium Acetate, 150 mM NaCl, 10 mM $CaCl_2$, 0.5 mM $MgCl_2$, and 0.5% BSA) for 2 hrs at 37° C. Both the sialidase treated and the untreated control cells (treated with only EDB/BSA buffer) were infected with 0.1 MOI of virus. After 1 hour, the cells were washed two times with PBS and incubated in DMEM: F12 supplemented with 0.2% ITS (Gibco) and 0.6 ug/ml acetylated trypsin (Sigma). Forty to 48 hours post-infection, the levels of cell-bound virus were determined by using a cell-based ELISA assay. Specifically, cells were fixed in 0.05% glutaraldehyde in PBS and were incubated with 50 μl of $10^3$ dilution of either anti-influenza A NP antiserum or anti-influenza B (Fitzgerald Inc.) in 0.5% BSA and PBS at 37° C. for 1 hr. After washing, each well was incubated with HRP-protein G in 0.5% BSA and PBS for 1 hr. After final washes, 50 μl of 25 mM sodium citrate (pH 4.5) containing 0.02% 3,3',5,5'-tetramethylbenzidine dihydrochloride (Sigma) and 0.01% hydrogen peroxide was allowed to react with the cells at room temperature for 5 min. The reactions were stopped by adding 50 μl of 1M $H_2SO_4$, and quantitated by measuring optical densities at 450 nM. Percentage viral replication inhibition is calculated by 100%×{(virus only samples−sialidase treated samples)/(virus only samples−uninfected samples)}.

Data on inhibition of viral replication and cell protection EC50's and selective indexes for recombinant sialidase fusion proteins AR-AvCD made from Construct #2 and AR-$G_4$S-AvCD made from Construct #3 for a variety of human influenza A and influenza B viruses, as well as equine viruses are shown in FIG. 12.

As shown in FIG. 10, sialidase fusion proteins strongly inhibited amplification of a broad selection of influenza viruses. Notably, 80-100% viral inhibition (FIG. 10) as well as cell protection (FIG. 9) was achieved although a maximum of 70-80% of cell surface sialic acid was removed by the sialidase treatment (FIG. 8). This finding demonstrates that it is unnecessary to completely eliminate cell surface sialic acid in order to achieve the desired therapeutic effect of treating with the sialidase fusion proteins of the present invention. The residual 20-30% of the surface sialic acid, while being inaccessible for the sialidase fusion proteins, is probably inaccessible for influenza viruses as well.

Cytotoxicity of Sialidase Fusion Proteins

To evaluate the cytotoxicity of AR-AvCD or AR-$G_4$S-AvCD proteins (made from Constructs #2 and #3), MDCK cells were seeded at low density in 96-well plates and cultured for 5 days in DMEM containing 10% FBS and up to 20 U of AR-AvCD protein or AR-$G_4$S-AvCD protein per well (both sialidases remained fully active during the entire experiment). Cell density in AR-AvCD or AR-$G_4$S-AvCD treated or control wells were determined every day by staining the cells with crystal violet and measuring absorption at 570 nM. No inhibition of cell growth was observed even at the highest concentration of AR-AvCD or AR-G$_4$S-AvCD (100 U/ml) in the culture. Therefore IC50, which is the drug concentration that inhibits cell growth by 50%, for AR-AvCD or AR-G$_4$S-AvCD is above 100 U/ml.

Example 14: In Vivo Activities of Sialidase Catalytic Domain Fusion Protein

Ferrets can be infected with human unadapted influenza viruses and produce signs of disease comparable to those of humans, which can be treated by antiviral compounds, such as zanamivir (Relenza). (Mendel et al., Antimicrob Agents Chemother, (1998) 42(3), 640-646; Smith and Sweet, Rev. Infect. Dis., (1988) 10(1), 56-75; Reuman et al., J. Virol. Methods, (1989) 24(1-2), 27-34). To evaluate in vivo efficacy of our compounds, we tested AR-AvCD protein (made from Construct #2) in the ferret model. Specifically, 24 young female ferrets (0.5-0.8 kg) (Marshall Farms, North Rose, N.Y.) that tested negative for the presence of anti-hemagglutinin antibodies in sera were included in the study. Two animals were placed in each cage and allowed to acclimate for 3 days before the experiment. The animals were randomly divided into three groups: 8 animals were treated with drug dilution buffer and viral challenge, 12 animals were treated with AR-AvCD and viral challenge, and 4 animals were treated with AR-AvCD only. A preparation of AR-AvCD dissolved in phosphate buffered saline (PBS) that contains 500 U/ml in sialidase activity and 0.7 mg/ml in protein concentration was used in the study. Animals in the drug treatment groups received 1 ml of AR-AvCD at each dose, which amounts to about 1 mg/kg in dosage level.

Ferrets were anesthetized and inoculated intranasally (0.5 ml into each nostril) with AR-AvCD or PBS twice (8 am and 6 pm) and daily for a total of 7 days (2 days prior to the viral challenge and 5 days post virus inoculation). The ferrets were observed following the drug application for signs of intolerance. Viral inoculation was carried out on day 3 between 10-11 am. The viral challenge was done with human A/Bayern/7/95 (H1N1)-like virus at dose $10^5$ TCID$_{50}$ ($\geq 10^4$ ferret ID$_{50}$). The nasal washes were collected from all animals starting day 2 post AR-AvCD treatment and continued until day 7. To collect nasal washes, 1 ml of sterile PBS was administered intranasally, the sneezed liquid was harvested and its volume was recorded. The nasal washes were centrifuged. The pelleted cells were re-suspended and counted in a hemacytometer under a microscope. The supernatants were collected, aliquoted and stored at −80° C. The protein concentration in cell-free nasal washes was determined by using the Bio-Rad protein reagent according to manufacturer's protocol (Bio-Rad, Hercules, Calif.). For virus titration of the nasal washes, inoculated MDCK cells were incubated for 3 days at 36° C. in a CO$_2$ incubator. The monolayers were inspected visually for cytopathic effect (CPE) and aliquots of the cell culture supernatants from each well were tested for the virus presence by a standard hemagglutination assay with guinea pig red blood cells. Viral titer was determined by the Spearman Karber method ((1996)).

In uninfected animals given intranasal AR-AvCD (n=4), no apparent effect on the inflammatory cell counts and protein concentrations in the nasal washes was observed (FIGS. 15 A and B). Nasal washes from these animals were followed for 7 days and were all negative for viral shedding.

No signs of drug-related toxicity were detected in these animals at the drug dose used in this study. In the vehicle-treated group, virus replicated in the nasal epithelium of all 8 ferrets. Viral shedding reached peak values of 4.4 to 5.9 log$_{10}$ TCID$_{50}$ (mean peak titer of 4.9) on day 1 or 2 post challenge, diminished over time and became negative by day 5 (FIG. 13). By contrast, only 3 of 12 AR-AvCD-treated ferrets were positive for viral shedding on day 1 post challenge (FIG. 13), and their nasal viral titers were about 100 times lower than those in the vehicle-treated animals (mean 2.4±0.3 vs. 4.4±0.4 log$_{10}$ TCID$_{50}$) (FIG. 13). After day 1, the response to the AR-AvCD treatment varied substantially. Three animals were completely protected against infection, signs of illness, and inflammatory response (FIG. 13), ferret tag #803, 805, 806). The protection was also confirmed by a lack of seroconversion on day-14 post challenge. One ferret (tag #780) did not shed virus during the first three days post challenge, but it died on day 4 post infection from an unrelated injury. The shedding in the remaining 8 ferrets varied during the course of infection, ranging from ferret #812 that shed virus for a day only, to the ferret #791 that shed virus for 5 days.

Infection in the ferrets that shed virus for at least one day was confirmed by more than a 16-fold rise in the post-challenge anti-HA antibody titer (seroconversion). There was no apparent effect of AR-AvCD treatment on the anti-HA titers in post-challenge sera (320-1280, vs. 160-1280, vehicle- and drug-treated group, respectively).

Figure 11:
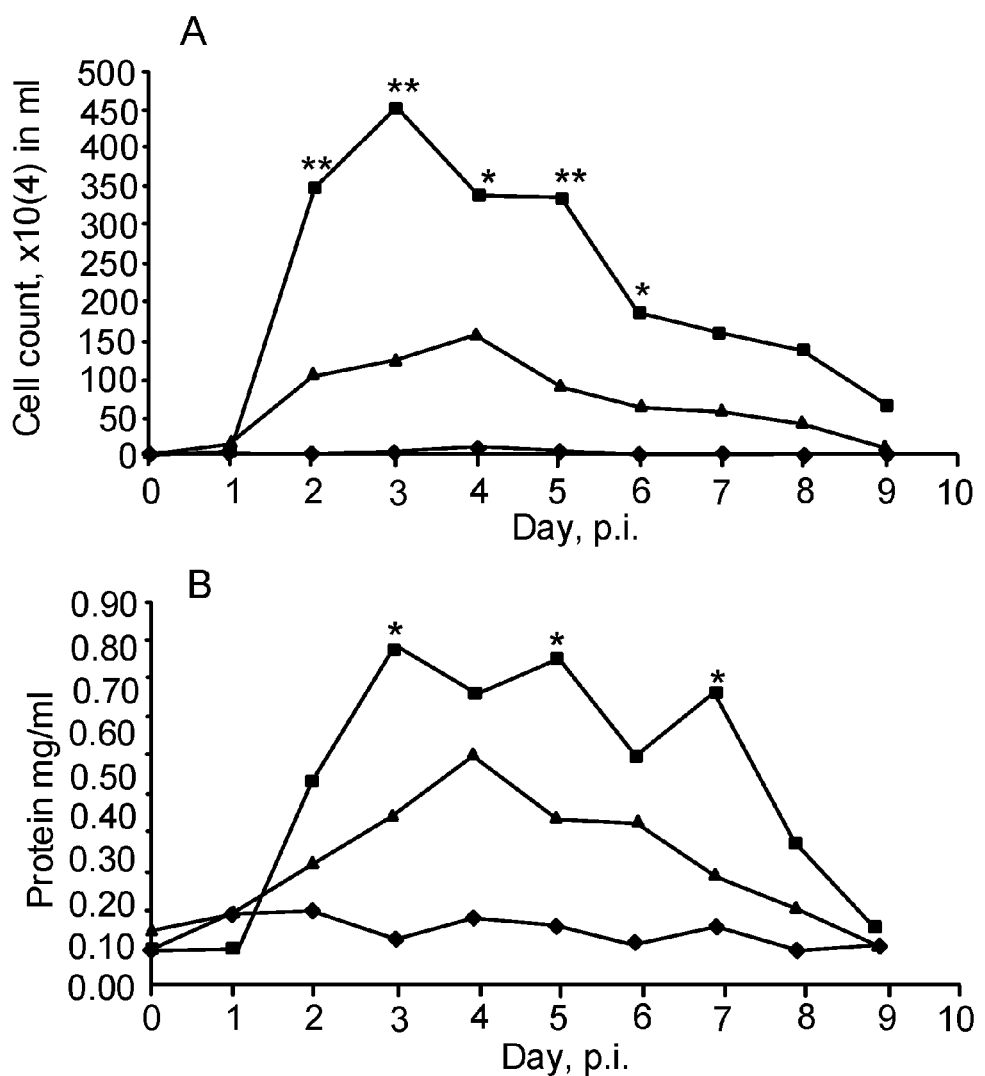

In ferrets that shed the virus despite the AR-AvCD treatment (n=8), the inflammatory response was reduced and animals appeared to be more alert and active compared to the untreated ferrets that were invariably lethargic and feverish. For this group of 8 infected, AR-AvCD-treated animals, the mean AUC (area under the curve) value calculated for the nasal protein concentrations was reduced by approximately 40% (2.68 vs. 4.48, arbitrary units) compared to the vehicle-treated infected animals (FIG. 11B). In vehicle-treated infected animals, the number of inflammatory cells in nasal washes was increased to approximately 100-fold above those in uninfected animals on day 2 post challenge. These levels were sustained for 4 additional days. The AR-AvCD-treated animals exhibited a significant reduction in the number of inflammatory cells in the nasal washes. Specifically, the AUC value for cell counts was reduced by approximately 3-fold in the AR-AvCD-treated animals compared to the vehicle-treated infected animals (1965 vs. 674, arbitrary units, FIG. 11A). The observed reduction in the inflammatory response indicates the importance of inhibiting viral replication at the early stage of infection.

Example 15: Inhibition of Bacterial Cell Adhesion by Sialidase Fusion Proteins Bacteria S. pneumoniae: 10 encapsulated strains of different serotypes are selected from the clinical isolates deposited at ATCC. Bacteria are maintained as frozen stocks and passaged on tryptic soy agar plates containing 3% sheep blood (Difco & Micropure Medical Inc.) for 18 hr at 37° C. in 5% CO$_2$. To label pneumococci with radioisotope, an inoculum is taken from a 1- to 2-day plate culture, added to lysine-deficient tryptic soy broth containing 70 µCi of [$^3$H] lysine per ml and incubated at 37° C. in 5% CO$_2$. The growth of each culture is monitored by light absorbance at 595 nm. At late logarithmic phase, the bacteria are harvested, washed twice by centrifugation (13,000 rpm×3 min), and resuspended in L-15 medium (without phenol red) plus 0.1%

BSA (L-15-BSA) (Cundell and Tuomanen, Microb. Pathog., (1994) 17(6), 361-374) (Barthelson et al., Infect. Immun., (1998) 66(4), 1439-1444).

*H. influenzae:* 5 strains of type b (Hib) and 10 nontypable strains (NTHi) are obtained from the clinical isolates deposited at ATCC. All strains are stocked in brain heart infusion (BHI, Difco) containing hemin (ICN) and NAD (Sigma) and kept frozen until use; then they are cultured on BHI agar supplemented with hemin and NAD and grown for 14 hr at 37° C. with 5% $CO_2$. (Kawakami et al., Microbiol. Immunol., (1998) 42(10), 697-702). To label the bacteria with [$^3$H], *H. influenzae* cells are inoculated in BHI broth containing hemin, NAD and [$^3$H]leucine at 250 µCi/ml and allowed to grow until late logarithmic phase and then harvested, washed and resuspended in L-15-BSA (Barthelson et al., Infect. Immun., (1998) 66(4), 1439-1444).

Cell Adhesion Assay

All [$^3$H]-labeled bacteria are suspended in L-15-BSA after washing, the bacterial concentration is determined by visual counting with a Petroff-Hausser chamber, radioactivity is determined by scintillation counting, and the specific activity of the [$^3$H]-labeled cells is calculated. Preparations of bacteria with 7 cpm/1000 cells or greater are used. The bacteria are diluted to $5 \times 10^8$ cells/ml. BEAS-2B cell monolayers are incubated with [$^3$H]-labeled bacterial suspension containing $5 \times 10^7$ bacteria at 37° C. in 5% $CO_2$. After 30 min, unbound bacteria are removed by washing with L-15-BSA for 5 times. Bacteria attached to the WD-HAE tissue samples are quantitated by scintillation counting.

Desialylation of BEAS-2B Cells by Sialidase Fusion Proteins and Effects on Cell Adhesion by *H. influenzae* and *S. pneumoniae*.

BEAS-2B cells are incubated with 1-50 mU of AR-AvCD for 2 hours. Cell adhesion assay will be carried out using *H. influenzae* and *S. pneumoniae* strains as described above. Mock treated cells are used as positive control. Efficacy of AR-AvCD is quantitated as the $EC_{50}$, which is the amount of enzyme to achieve 50% inhibition on bacterial adhesion.

Example 16: Improving Transduction Efficiency of AAV Vector Using Sialidase Fusion Proteins In Vitro Experiments An experiment demonstrating effect of AR-AvCD is performed in a way similar to the procedure published (Bals et al., J Virol., (1999) 73(7), 6085-6088). A monolayer of Well-Differentiated Airway Epithelium (WDAE) cells is maintained in transwells (Karp et al., Methods Mol. Biol., (2002) 188, 115-137; Wang et al., J Virol., (1998) 72(12), 9818-9826). In order to eliminate sialic acid from the cell surface the culture medium is replaced with serum free medium in which 0.5-10 units of AR-AvCD are dissolved. The cells are treated for 30 min to 6 hours. The cell monolayers are washed, transduced with AAV, and transduction efficiency is estimated using standard procedures. Several transwells are treated with medium only (without AR-AvCD) to serve the purpose of control (basal transduction efficiency). Additional controls may include the transwells treated with AR-AvCD only to assess cytotoxic effect of desialylation. A reporter virus is used for facile detection of transduced cells. Examples of reporter AAV and their use have been described in literature and include AAV-CMV-eGFP, AAV2LacZ (Bals et al., J Virol., (1999) 73(7), 6085-6088; Wang et al., Hum. Gene Ther., (2004) 15(4), 405-413) and alkaline phosphatase (Halbert et al., Nat. Biotechnol., (2002) 20(7), 697-701). The efficiency is estimated by light microscopy of the cells that were fixed and treated with appropriate substrate (if lacZ or AP containing virus is used) or fluorescent microscopy of live cells (if GFP is used). According to the experiments conducted at NexBio with NHBE primary epithelial cells (Cambrex, Walkersville, Md.) the maximum amount of removal of sialic acid is achieved in less than one hour when 10 units of AR-AvCD per transwell are used. Other cell lines used (e.g. MDCK) become desialylated with much less AR-AvCD administered (0.1 U for 1 hour). It is therefore our estimate that a treatment of WDAE with 10 U of AR-AvCD for 2 hours will be sufficient to remove accessible sialic acid and provide significant enhancement of transduction of WDAE cells with AAV.

Testing Effect of AR-AvCD Treatment on AAV Transduction in an Animal Model.

To demonstrate effect of AR-AvCD treatment in animal model an experiment similar to previously described is conducted (Flotte et al., Proc. Natl. Acad. Sci. U.S.A, (1993) 90(22), 10613-10617; Halbert et al., Nat. Biotechnol., (2002) 20(7), 697-701). Several hours (1-6) prior to administration of AAV AR-AvCD is delivered to mice lungs by nasal aspiration of aerosol or lyophilized AR-AvCD powder according to previously published protocol (Flotte et al., Proc. Natl. Acad. Sci. U.S.A, (1993) 90(22), 10613-10617). AAV carrying reporter gene (alkaline phosphatase) is delivered by nasal aspiration, mice are euthanized 4 weeks later and transduced cells are detected in fixed lungs as previously described (Halbert et al., J Virol., (1998) 72(12), 9795-9805).

Example 17: Sialidase Treatment Inhibits Mast Cell Functions and Smooth Muscle Contraction in the Trachea Using experimental methods described previously (Cocchiara et al., J Neuroimmunol., (1997) 75(1-2), 9-18), it will be demonstrated that treatment by compounds of the present invention prevents substance P (SP) induced histamine release by mast cells. Using another set of experiments (Stenton et al., J Pharmacol. Exp. Ther., (2002) 302(2), 466-474), treatment by compounds of the present invention will inhibit β-hexosaminidase release by mast cells stimulated by two PAR-activating peptides (PAR stands for proteinase-activated receptors).

Compounds of the present invention will be administered intratracheally in guinea pigs and the airway reactivity will be assessed in the animals as described previously (Jarreau et al., Am. Rev. Respir. Dis., (1992) 145(4 Pt 1), 906-910; Stenton et al., J Pharmacol. Exp. Ther., (2002) 302(2), 466-474). Sialidase treatment should not induce nonspecific airway hyperreactivity judged by the reaction to multiple inducers. In addition, sialidase treatment should reduce substance P-induced bronchoconstriction. Similarly, compounds of the present invention will be used to treated the isolated guinea pig and rat trachea and lung (Kai et al., Eur. J. Pharmacol., (1992) 220(2-3), 181-185; Stenton et al., J Pharmacol. Exp. Ther., (2002) 302(2), 466-474). Again recombinant sialidase treatment will have no effect on smooth muscle contractions induced by acetylcholine, histamine and 5-hydroxytryptamine. In addition, it will inhibit tracheal contraction induced by antigen (ovalbumin) or compound 48/80.

BIBLIOGRAPHY

Achyuthan, K E and Achyuthan A M. 2001. Comparative enzymology, biochemistry and pathophysiology of human exo-a-sialidases (neuraminidases). *Comparative Biochem & Physiol* part B 129:29-64.

Air, G M and Laver, W G. 1995. Red cells bound to influenza virus N9 neuraminidase are not released by the N9 neuraminidase activity. Virology 211:278-284.

Auerswald E A, Horlein D, Reinhardt G, Schroder W and Schnabel E. 1988. Expression, isolation and characterization of recombinant [Arg$^{15}$, Glu$^{52}$] Aprotinin. Biol Chem Hoppe-Seyler Vol 369, Suppl., pp 27-35.

Barbey-Morel C L, Oeltmann T N, Edwards K M and Wright P F. 1987. Role of respiratory tract proteases in infectivity of influenza A virus. J Infect Dis 155:667-672.

Bessette P H, Aslund F, Beckwith J and Georgiou G. 1999. Efficient folding of proteins with multiple disulfide bonds in the *Escherichia coli* cytoplasm. Pro Natl Acad Sci USA 96:13703-13708.

Callan R J, Hartmann F A, West S E and Hinshaw V S. 1997. Cleavage of influenza A virus H1 hemagglutinin by swine respiratory bacterial proteases. J Virol 71:7579-7585.

Connor, R J, Kawaoka, Y, Webster, R G and Paulson J C. 1994. Receptor specificity in human, avian, and equine H2 and H3 influenza virus isolates. *Virology* 205:17-23.

Copley, R R, Russell, R B and Ponting, C P. 2001. Sialidase-like Asp-boxes: sequence-similar structures within different protein folds. *Prot Sci* 10:285-292.

Corfield, A P, Veh, R W, Wember, M, Michalski, J C and Schauer, R. 1981. The release of N-acetyl- and N-glycolloyl-neuraminic acid from soluble complex carbohydrates and erythrocytes by bacterial, viral and mammalian sialidases. *Bichem J* 197:293-299.

Crennell, S J, Garman, E, Laver, G, Vimr, E and Taylor, G. 1994. Crystal structure of *Vibrio Cholerae* neuraminidase reveals dual lectin-like domains in addition to the catalytic domain. *Structure* 2:535-544.

Drzeniek, R. Substrate specificity of neuraminidases. 1973. *Histochem J* 5:271-290.

Endo Y, Carroll K N, Ikizler M R and Wright P F. 1996. Growth of influenza virus in primary, differentiated epithelial cells derived from adenoids. J Virol 70:2055-2058.

Fritz H and Wunderer G. 1983. Biochemistry and applications of aprotinin, the kallikrein inhibitor from bovine organs. *Arzneim-Forsch* 33:479-494.

Fukudome, K., Yoshie, O. and Konno, T. 1989. Comparison of human, simian, and bovine rotaviruses for requirement of sialic acid in hemagglutination and cell adsorption. Virology 172:196-205.

Garten W, Bosch F X, Linder D, Rott R and Klenk H D. 1981. Proteolytic activation of the influenza virus hemagglutining the structure of the cleavage site and the enzymes involved in cleavage. Virology 115:361-374.

Goger, B, Halden, Y, Rek, A, Mosl, R, Pye, D, Gallagher, J and Kungl, A J. 2002. Different affinities of glycosaminoglycan oligosaccharides for monomeric and dimeric interleukin-8: a model for chemokine regulation at inflammatory sites. Bichem 41:1640-1646.

Gotoh B, Ogasawara T, Toyoda T, Inocencio N, Hamaguchi M and Nagai Y. 1990. An endoprotease homologous to the blood clotting factor X as a determinant of viral tropism in chick embryo. EMBO J 9:4189-4195.

Granoff, A. & Webster, R. G., ed. *Encyclopedia of Virology*, 2$^{nd}$ Edition, Vol 2.

Gust, I D, Hampson, A W. and Lavanchy, D. 2001. Planning for the next pandemic. *Rev Med Virol* 11:59-70.

Hayden, F G. 1996. Amantadine and rimantadine-mechanisms. In *Antiviral drug resistance* (ed. D. D. Richman), pp. 59-77. Chichester, U K: John Wiley & Sons Ltd.

Hosoya M, Matsuyama S, Baba M, Susuki H and Shigeta S. 1992. Effects of protease inhibitors on replication of various myxoviruses. Antimicrobial Agents and Chemotherapy 36:1432-1436.

Ito, T. 2000. Interspecies transmission and receptor recognition of influenza a virus. *Microbiol Immunol* 44(6):423-430.

Janakiraman, M N, White, C L, Laver, W G, Air, G M and Luo, M. 1994. Structure of influenza virus neuraminidase B/lee/40 complexed with sialic acid and a dehydro analog at 1.8-A resolution: implications for the catalytic mechanism. *Biochemistry* 33:8172-8179.

Kido, H, Niwa, Y, Beppu, Y and Towatari, T. 1996. Cellular proteases involved in the pathogenicity of enveloped animal viruses, human immunodeficiency virus, influenza virus A and sendai virus. Advan Enzyme Regul 36:325-347.

Kido H, Chen Y and Murakami M. 1999. Cellular proteinases and viral infection: influenza virus, sendai virus and HIV-1, p. 205-217. In B. Dunn (ed.), Proteases of infectious agents. Academic Press, New York, N.Y.

Klenk, H D and Rott, R. 1988. The molecular biology of influenza virus pathogenicity. Adv Vir Res 34:247-281.

Klenk, H D and Garten W. 1994. Host cell proteases controlling virus pathogenicity. Trend Micro 2:39-43.

Kreisel, W, Volk, B A, Buchsel, R. and Reutter, W. 1980. Different half-lives of the carbohydrate and protein moieties of a 110,000-dalton glycoproteins isolated from plasma membranes of rat liver. Proc Natl Acad Sci USA 77:1828-1831.

Krunkosky T M, Fischer B M, Martin L D, Jones N, Akley N J and Adler K B. 2000. Effects of TNF-β on expression of ICAM-1 in human airway epithelial cells in vitro. Am J Respir Cell Mol Biol 22:685-692.

Lazarowitz S G, Goldberg A R and Choppin P W. 1973. Proteolytic cleavage by plasmin of the H A polypeptide of influenza virus: host cell activation of serum plasminogen. Virology 56:172-180.

Lee, M K and Lander, A D. 1991. Analysis of affinity and structural selectivity in the binding of proteins to glycosaminoglycans: development of a sensitive electrophoretic approach. Pro Natl Acad Sci USA 88:2768-2772.

Meltzer, M I, Cox, N J and Fukuda, K. 1999. The economic impact of pandemic influenza in the United States: priorities for intervention. *Emerg Infect Dis* 5:659-671.

Meyer, F A, King, M and Gelman, R A., 1975. On the role of sialic acid in the rheological properties of mucus. Biochimica et Biophysica Acta 392: 223-232.

Milner, C M, Smith, S V, Carrillo M B, Taylor, G L, Hollinshead, M and Campbell, R D. 1997. Identification of a sialidase encoded in the human major histocompatibility complex. *J Bio Chem* 272:4549-4558.

Monti, E, Preti, A, Venerando, B and Borsani, G. 2002. Recent development in mammalian sialidase molecular biology. Neurochem Res 27:646-663.

Monti, E, Preti, A, Nesti, C, Ballabio, A and Borsani G. 1999. Expression of a novel human sialidase encoded by the NEU2 gene. *Glycobiol* 9:1313-1321.

Monti, E, Bassi, M T, Papini, N, Riboni, M, Manzoni, M, Veneranodo, B, Croci, G, Preti, A, Ballabio, A, Tettamanti, G and Borsani, G. 2000. Identification and expression of NEU3, a novel human sialidase associated to the plasma membrane. *Bichem J* 349:343-351.

Murakami M, Towatari T, Ohuchi M, Shiota M, Akao M, Okumura Y, Parry M A and Kido H. 2001. Mini-plasmin found in the epithelial cells of bronchioles triggers infection by broad-spectrum influenza A viruses and Sendai virus. Eur J Biochem 268: 2847-2855.

Nakayama, K. 1997. Furin: a mammalian subtilisin/kex2p-like endoprotease involved in process of a wide variety of precursor proteins. Biochem 327:625-635.

Ovcharenko A V and Zhirnov O P. 1994. Aprotinin aerosol treatment of influenza and paramyxovirus bronchopneumonia of mice. Antiviral Res 23:107-118.

Pshezhetsky, A, Richard, C, Michaud, L, Igdoura, S, Wang, S, Elsliger, M, Qu, J, Leclerc, D, Gravel, R, Dallaire, L and Potier, M. 1997. Cloning, expression and chromosomal mapping of human lysosomal sialidase and characterization of mutations in sialidosis. *Nature Genet* 15: 316-320.

Ramphal, R. and Pyle, M. 1983. Evidence for mucins and sialic acid as receptors for *Pseudomonas aeruginosa* in the lower respiratory tract. Infect Immun 41:339-44.

Roggentin, P, Kleineidam, R G and Schauer, R. 1995. Diversity in the properties of two sialidase isoenzymes produced by *Clostridium perfringens* spp. *Biol Chem Hoppe-Seyler* 376:569-575.

Roggentin, P, Schauer, R, Hoyer, L L and Vimr, E R. 1993. The sialidase superfamily and its spread by horizontal gene transfer. Mol Microb 9:915-921.

Rosenberg A. ed. Biology of the Sialic Acids. 1995. pp 270-273.

Sakurada, K, Ohta, T and Hasegawa, M. 1992. Cloning, expression and characterization of the *Micromonospora viridifaciens* neuraminidase gene in *Streptomyces lividans*. J Bacteriol 174: 6896-6903.

Schauer, S. ed., pp 233. Sialic Acids Chemistry, Metabolism and Function. Springer-Verlag, 1982.

Schauer, R. 1982. Chemistry, metabolism, and biological functions of sialic acids. Adv. *Carbohydrate Chem & Biochem* 40:131-235.

Scheiblauer H, Reinacher M, Tashiro M and Rott R. 1992. Interactions between bacteria and influenza A virus in the development of influenza pneumonia. J Infec Dis 166: 783-791.

Sinn P L, Williams G, Vongpunsawad S, Cattaneo R and McCray P B. 2002. Measles virus preferentially transduces the basolateral surface of well-differentiated human airway epithelia. *J Virol* 76:2403-2409.

Skehel, J J and Wiley, D C. 2000. Receptor binding and membrane fusion in virus entry: the influenza hemagglutinin. Annu Rev Biochem 69:531-569.

Tashiro M, Klenk H D and Rott R. 1987 Inhibitory effect of a protease inhibitor, leupeptin, on the development of influenza pneumonia, mediated by concomitant bacteria. J Gen Virol 68:2039-2043.

Tashiro M, Ciborowski P, Reinacher M, Pulverer G, Klenk H D and Rott R. 1987. Synergistic role of staphylococcal proteases in the induction of influenza virus pathogenecity. *Virology* 157:421-430.

Teufel, M, Roggentin, P. and Schauer, R. 1989. Properties of sialidase isolated from *Actinomyces viscosus* DSM43798. Biol Chem Hoppe Seyler 370:435-443.

Tobita, K, Sugiura, A, Enomoto, C and Furuyama, M. 1975. Plaque assay and primary isolation of influenza A viruses in an established line of canine kidney cells (MDCK) in the presence of trypsin. Med Microbiol Immnuol 162:9-14.

Venturi M, Seifert C and Hunte C. 2001. High level production of functional antibody Fab fragments in an oxidizing bacterial cytoplasm. J Mol Biol 315:1-8.

Vimr, D R. 1994. Microbial sialidases: does bigger always mean better? *Trends Microbiol* 2: 271-277.

Vlasak, R., Luytjes, W., Spaan, W. and Palese, P. 1988. Human and bovine coronaviruses recognize sialic acid-containing receptors similar to those of influenza C viruses. Proc Natl Acad Sci USA 85:4526-4529.

Wada, T, Yoshikawa, Y, Tokuyama, S, Kuwabara, M, Akita, H and Miyagi, T. 1999. Cloning, expression, and chromosomal mapping of a human ganglioside sialidase. *Biochem Biophy Res Communi* 261:21-27.

Wang, F Z, Akula, S M, Pramod, N P, Zeng, L and Chandran, B. 2001. Human herpesvirus 8 envelope glycoproteins K8.1A interaction with the target cells involves heparan sulfate. *J Virol* 75:7517-27

Wassilewa, L. 1977. Cell receptor for paramyxoviruses. Arch Virol 54:299-305.

Weisgraber, K H, Rall, S C, Mahley, R W, Milne, R W and Marcel, Y. 1986. Human apoliproprotein E, determination Witt, D P and Lander A D. 1994. Differential binding of chemokines to glycosaminoglycan subpopulations. Curr Bio 4:394-400.

Wood, J. 2001. Developing vaccines against pandemic influenza. *Phil Trans R Soc Lond B* 356:1953-1960.

Xiang Y and Moss B. 2003. Molluscum contagiosum virus interleukin-18 (IL-18) binding protein is secreted as a full-length form that bind cell surface glycosaminoglycans through the C-terminal tail and a furin-cleaved form with only the IL-18 binding domain. J Virol 77:2623-2630.

Zambon, M. 2001. The pathogenesis of influenza in humans. Rev Med Virol 11:227-241.

Zhang L, Peeples M E, Boucher R C, Collins P L and Pickles R J. 2002. Respiratory syncytial virus infection of human airway epithelial cells is polarized, specific to ciliated cells, and without obvious cytopathology. J Virol 76:5654-5666.

Zhirnov O P, Ovchartenko A V and Bukrinskaya A G. 1982. Protective effect of protease inhibitors in influenza virus infected animals. Arch Virol 73:263-272

Zhirnov O P, Ovcharenko A V and Bukrinskaya A G. 1982. A modified plaque assay method for accurate analysis of infectivity of influenza viruses with uncleaved hemagglutinin. Arch Virol 71:177-183.

Zhirnov O P. 1983. Proteolytic activation of myxoviruses and a new strategy in the treatment of viral diseases. Problems Virol. 4:9-12. (In Russian).

Zhirnov O P, Ovcharenko A V and Bukrinskaya A G. 1984. Suppression of influenza virus replication in infected mice by protease inhibitors. J Gen Virol 65:191-196.

Zhirnov O P, Ovcharenko A V and Bukrinskaya A G. 1985. Myxovirus replication in chicken embryos can be suppressed by aprotinin due to the blockage of viral glycoprotein cleavage. J Gen Virol 66:1633-1638.

Zhirnov O P. 1987. High protection of animals lethally infected with influenza virus by aprotinin-rimantadine combination. J Med Virol 21:161-167.

Zhirnov O P, Ikizler M R and Wright P F. 2002. Cleavage of influenza A virus hemagglutinin in human respiratory epithelium is cell associated and sensitive to exogenous antiproteases. *J Virol* 76:8682-8689.

Bartlett J. G., Breiman R. F., Mandell L. A., & File T. M., Jr. (1998) Community-acquired pneumonia in adults: guidelines for management. The Infectious Diseases Society of America. *Clin. Infect. Dis.* 26, 811-838.

Andrews J., Nadjm B., Gant V., & Shetty N. (2003) Community-acquired pneumonia. *Curr. Opin. Pulm. Med.* 9, 175-180.

File T. M. (2000) The epidemiology of respiratory tract infections. *Semin. Respir. Infect.* 15, 184-194.

Macfarlane J. (1994) An overview of community acquired pneumonia with lessons learned from the British Thoracic Society Study. *Semin. Respir. Infect.* 9, 153-165.

Matsushima T., Miyashita N., & File T. M., Jr. (2002) Etiology and management of community-acquired pneumonia in Asia. *Curr. Opin. Infect. Dis.* 15, 157-162.

Ball P. (1995) Epidemiology and treatment of chronic bronchitis and its exacerbations. *Chest* 108, 43S-52S.

Faden H. (2001) The microbiologic and immunologic basis for recurrent otitis media in children. *Eur. J Pediatr.* 160, 407-413.

Garcia-Rodriguez, J A and Martinez, M J F. Dynamics of nasopharyngeal colonization by potential respiratory pathogens. J Antimicrob Chemother 50[Suppl S2], 59-73. 2002.

Soriano F. & Rodriguez-Cerrato V. (2002) Pharmacodynamic and kinetic basis for the selection of pneumococcal resistance in the upper respiratory tract. *J Antimicrob Chemother* 50 Suppl S2, 51-58.

Mbaki N., Rikitomi N., Nagatake T., & Matsumoto K. (1987) Correlation between *Branhamella catarrhalis* adherence to oropharyngeal cells and seasonal incidence of lower respiratory tract infections. *Tohoku J Exp. Med.* 153, 111-121.

Zopf D. & Roth S. (1996) Oligosaccharide anti-infective agents. *Lancet* 347, 1017-1021.

Cundell D. R., Weiser J. N., Shen J., Young A., & Tuomanen E. I. (1995) Relationship between colonial morphology and adherence of *Streptococcus pneumoniae*. *Infect. Immun.* 63, 757-761.

Karlsson K. A. (1998) Meaning and therapeutic potential of microbial recognition of host glycoconjugates. *Mol. Microbiol.* 29, 1-11.

Andersson B., Porras O., Hanson L. A., Lagergard T., & Svanborg-Eden C. (1986) Inhibition of attachment of *Streptococcus pneumoniae* and *Haemophilus influenzae* by human milk and receptor oligosaccharides. *J Infect. Dis.* 153, 232-237.

Bals R., Xiao W., Sang N., Weiner D. J., Meegalla R. L., & Wilson J. M. (1999) Transduction of well-differentiated airway epithelium by recombinant adeno-associated virus is limited by vector entry. *J Virol.* 73, 6085-6088.

Barthelson R., Mobasseri A., Zopf D., & Simon P. (1998) Adherence of *Streptococcus pneumoniae* to respiratory epithelial cells is inhibited by sialylated oligosaccharides. *Infect. Immun.* 66, 1439-1444.

Cundell D. R. & Tuomanen E. I. (1994) Receptor specificity of adherence of *Streptococcus pneumoniae* to human type-II pneumocytes and vascular endothelial cells in vitro. *Microb. Pathog.* 17, 361-374.

Fakih M. G., Murphy T. F., Pattoli M. A., & Berenson C. S. (1997) Specific binding of *Haemophilus influenzae* to minor gangliosides of human respiratory epithelial cells. *Infect. Immun.* 65, 1695-1700.

Kawakami K., Ahmed K., Utsunomiya Y., Rikitomi N., Hori A., Oishi K., & Nagatake T. (1998) Attachment of nontypable *Haemophilus influenzae* to human pharyngeal epithelial cells mediated by a ganglioside receptor. *Microbiol. Immunol.* 42, 697-702.

Solzbacher D., Hanisch F. G., van Alphen L., Gilsdorf J. R., & Schroten H. (2003) Mucin in middle ear effusions inhibits attachment of *Haemophilus influenzae* to mucosal epithelial cells. *Eur. Arch. Otorhinolaryngol.* 260, 141-147.

van Alphen L., Geelen-van den Broek L., Blaas L., van Ham M., & Dankert J. (1991) Blocking of fimbria-mediated adherence of *Haemophilus influenzae* by sialyl gangliosides. *Infect. Immun.* 59, 4473-4477.

Ahmed K., Matsumoto K., Rikitomi N., & Nagatake T. (1996) Attachment of *Moraxella catarrhalis* to pharyngeal epithelial cells is mediated by a glycosphingolipid receptor. *FEMS MicrobiaLett.* 135, 305-309.

Hazlett L. D., Moon M., & Berk R. S. (1986) In vivo identification of sialic acid as the ocular receptor for *Pseudomonas aeruginosa*. *Infect. Immun.* 51, 687-689.

Baker N., Hansson G. C., Leffler H., Rfise G., & Svanborg-Eden C. (1990) Glycosphingolipid receptors for *Pseudomonas aeruginosa*. *Infect. Immun.* 58, 2361-2366.

Schultze B., Gross H. J., Brossmer R., & Herrler G. (1991) The S protein of bovine coronavirus is a hemagglutinin recognizing 9-O-acetylated sialic acid as a receptor determinant. *J Virol.* 65, 6232-6237.

Wuppermann F. N., Hegemann J. H., & Jantos C. A. (2001) Heparan sulfate-like glycosaminoglycan is a cellular receptor for *Chlamydia pneumoniae*. *J Infect. Dis.* 184, 181-187.

Beswick E. J., Travelstead A., & Cooper M. D. (2003) Comparative studies of glycosaminoglycan involvement in *Chlamydia pneumoniae* and *C. trachomatis* invasion of host cells. *J Infect. Dis.* 187, 1291-1300.

Martinez I. & Melero J. A. (2000) Binding of human respiratory syncytial virus to cells: implication of sulfated cell surface proteoglycans. *J Gen. Virol.* 81, 2715-2722.

Thomas R. J. & Brooks T. J. (2004) Oligosaccharide receptor mimics inhibit *Legionella pneumophila* attachment to human respiratory epithelial cells. *Microb. Pathog.* 36, 83-92.

Hirmo S., Kelm S., Schauer R., Nilsson B., & Wadstrom T. (1996) Adhesion of *Helicobacter pylori* strains to alpha-2,3-linked sialic acids. *Glycoconj. J* 13, 1005-1011.

Simon P. M., Goode P. L., Mobasseri A., & Zopf D. (1997) Inhibition of *Helicobacter pylori* binding to gastrointestinal epithelial cells by sialic acid-containing oligosaccharides. *Infect. Immun.* 65, 750-757.

Miller-Podraza H., Bergstrom J., Milh M. A., & Karlsson K. A. (1997) Recognition of glycoconjugates by *Helicobacter pylori*. Comparison of two sialic acid-dependent specificities based on haemagglutination and binding to human erythrocyte glycoconjugates. *Glycoconj. J* 14, 467-471.

Crocker P. R. & Varki A. (2001) Siglecs, sialic acids and innate immunity. *Trends Immunol.* 22, 337-342.

Angata T. & Brinkman-Van der Linden E. (2002) I-type lectins. *Biochim. Biophys. Acta* 1572, 294-316.

Lyczak J. B., Cannon C. L., & Pier G. B. (2002) Lung infections associated with cystic fibrosis. *Clin. Microbiol. Rev.* 15, 194-222.

Flotte T. R. & Carter B. J. (1998) Adeno-associated virus vectors for gene therapy of cystic fibrosis. *Methods Enzymol.* 292, 717-732.

Wagner J. A., Reynolds T., Moran M. L., Moss R. B., Wine J. J., Flotte T. R., & Gardner P. (1998) Efficient and persistent gene transfer of AAV-CFTR in maxillary sinus. *Lancet* 351, 1702-1703.

Martinez I. & Melero J. A. (2000) Binding of human respiratory syncytial virus to cells: implication of sulfated cell surface proteoglycans. *J Gen. Virol.* 81, 2715-2722.

Park P. W., Pier G. B., Hinkes M. T., & Bernfield M. (2001) Exploitation of syndecan-1 shedding by *Pseudomonas aeruginosa* enhances virulence. *Nature* 411, 98-102.

Monti E., Preti A., Venerando B., & Borsani G. (2002) Recent development in mammalian sialidase molecular biology. *Neurochem. Res.* 27, 649-663. (1995) *Biology of the Sialic Acids,* 270-273.

Roggentin P., Kleineidam R. G., & Schauer R. (1995) Diversity in the properties of two sialidase isoenzymes produced by *Clostridium perfringens* spp. *Biol. Chem. Hoppe Seyler* 376, 569-575.

Sutter V. L. (1984) Anaerobes as normal oral flora. *Rev. Infect. Dis.* 6 Suppl 1, S62-S66.

Gaskell A., Crennell S., & Taylor G. (1995) The three domains of a bacterial sialidase: a beta-propeller, an immunoglobulin module and a galactose-binding jelly-roll. *Structure.* 3, 1197-1205.

Alvarez P., Buscaglia C. A., & Campetella O. (2004) Improving protein pharmacokinetics by genetic fusion to simple amino acid sequences. *J. Biol. Chem.* 279, 3375-3381.

Potier M., Mameli L., Belisle M., Dallaire L., & Melancon S. B. (1979) Fluorometric assay of neuraminidase with a sodium (4-methylumbelliferyl-alpha-D-N-acetylneuraminate) substrate. *Anal. Biochem.* 94, 287-296.

Hirel P. H., Schmitter M. J., Dessen P., Fayat G., & Blanquet S. (1989) Extent of N-terminal methionine excision from *Escherichia coli* proteins is governed by the side-chain length of the penultimate amino acid. *Proc. Natl. Acad. Sci. U.S.A* 86, 8247-8251.

Varshaysky A. (1996) The N-end rule: functions, mysteries, uses. *Proc. Natl. Acad. Sci. U.S.A* 93, 12142-12149.

Belshe R. B., Smith M. H., Hall C. B., Betts R., & Hay A. J. (1988) Genetic basis of resistance to rimantadine emerging during treatment of influenza virus infection. *J Virol.* 62, 1508-1512.

Mendel D. B., Tai C. Y., Escarpe P. A., Li W., Sidwell R. W., Huffman J. H., Sweet C., Jakeman K. J., Merson J., Lacy S. A., Lew W., Williams M. A., Zhang L., Chen M. S., Bischofberger N., & Kim C. U. (1998) Oral administration of a prodrug of the influenza virus neuraminidase inhibitor GS 4071 protects mice and ferrets against influenza infection. *Antimicrob Agents Chemother* 42, 640-646.

Smith H. & Sweet C. (1988) Lessons for human influenza from pathogenicity studies with ferrets. *Rev. Infect. Dis.* 10, 56-75.

Reuman P. D., Keely S., & Schiff G. M. (1989) Assessment of signs of influenza illness in the ferret model. *J. Virol. Methods* 24, 27-34.

Virology Methods Manual. 1996. London, San Diego, N.Y., boston, Sydney, Todyo, Toronto: Academic Press, Harcourt Brace & Company.

Karp P. H., Moninger T. O., Weber S. P., Nesselhauf T. S., Launspach J. L., Zabner J., & Welsh M. J. (2002) An in vitro model of differentiated human airway epithelia. Methods for establishing primary cultures. *Methods Mol. Biol.* 188, 115-137.

Wang G., Davidson B. L., Melchert P., Slepushkin V. A., van Es H. H., Bodner M., Jolly D. J., & McCray P. B., Jr. (1998) Influence of cell polarity on retrovirus-mediated gene transfer to differentiated human airway epithelia. *J Virol.* 72, 9818-9826.

Wang A. Y., Peng P. D., Ehrhardt A., Storm T. A., & Kay M. A. (2004) Comparison of adenoviral and adeno-associated viral vectors for pancreatic gene delivery in vivo. *Hum. Gene Ther.* 15, 405-413.

Halbert C. L., Allen J. M., & Miller A. D. (2002) Efficient mouse airway transduction following recombination between AAV vectors carrying parts of a larger gene. *Nat. Biotechnol.* 20, 697-701.

Flotte T. R., Afione S. A., Conrad C., McGrath S. A., Solow R., Oka H., Zeitlin P. L., Guggino W. B., & Carter B. J. (1993) Stable in vivo expression of the cystic fibrosis transmembrane conductance regulator with an adeno-associated virus vector. *Proc. Natl. Acad. Sci. U.S.A* 90, 10613-10617.

Halbert C. L., Standaert T. A., Wilson C. B., & Miller A. D. (1998) Successful readministration of adeno-associated virus vectors to the mouse lung requires transient immunosuppression during the initial exposure. *J Virol.* 72, 9795-9805.

Cocchiara R., Bongiovanni A., Albeggiani G., Azzolina A., Lampiasi N., Di Blasi F., & Geraci D. (1997) Inhibitory effect of neuraminidase on SP-induced histamine release and TNF-alpha mRNA in rat mast cells: evidence of a receptor-independent mechanism. *J Neuroimmunol.* 75, 9-18.

Stenton G. R., Nohara O., Dery R. E., Vliagoftis H., Gilchrist M., Johri A., Wallace J. L., Hollenberg M. D., Moqbel R., & Befus A. D. (2002) Proteinase-activated receptor (PAR)-1 and -2 agonists induce mediator release from mast cells by pathways distinct from PAR-1 and PAR-2. *J Pharmacol. Exp. Ther.* 302, 466-474.

Jarreau P. H., Harf A., Levame M., Lambre C. R., Lorino H., & Macquin-Mavier I. (1992) Effects of neuraminidase on airway reactivity in the guinea pig. *Am. Rev. Respir. Dis.* 145, 906-910.

Kai H., Makise K., Matsumoto S., Ishii T., Takahama K., Isohama Y., & Miyata T. (1992) The influence of neuraminidase treatment on tracheal smooth muscle contraction. *Eur. J. Pharmacol.* 220, 181-185.

All publications, including patent documents, Genbank sequence database entries including nucleotide and amino acid sequences and accompanying information, and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

---

What is claimed is:

1. A method for preparing a pharmaceutical composition, comprising
   (a) providing a fusion protein comprising at least one catalytic domain of a sialidase and an anchoring domain, wherein the catalytic domain comprises:
      (i) the sequence of amino acids extending from amino acid 274 to amino acid 681 of SEQ ID NO:12, inclusive and lacks the sequence that consists of the sequence extending from amino acid 1 to amino acid 273 and from amino acid 682 to amino acid 901 of SEQ ID NO:12;
      (ii) the sequence of amino acids extending from amino acid 290 to amino acid 666 of SEQ ID NO:12, inclusive and lacks the sequence that consists of the sequence extending from amino acid 1 to amino acid 289 and from amino acid 667 to amino acid 901 of SEQ ID NO:12; or
      (iii) the sequence of amino acids extending from amino acid 290 to amino acid 681 of SEQ ID NO:12, inclusive and lacks the sequence that consists of the sequence extending from amino acid 1 to amino acid 289 and from amino acid 682 to amino acid 901 of SEQ ID NO:12; and
   the anchoring domain comprises (SEQ ID NO:7); and
   (b) combining the fusion protein with a pharmaceutically acceptable carrier or diluent thereby creating a pharmaceutical composition.

2. The method of claim 1 wherein the pharmaceutical composition further comprises at least one of a preservative, a stabilizer, a dye and a flavoring agent.

3. The method of claim 1 wherein the pharmaceutical composition is a solution.

4. The method of claim 1 wherein the pharmaceutical composition is a suspension.

5. The method of claim 1 wherein the pharmaceutical composition is a powder.

6. The method of claim 1 wherein the catalytic domain comprises the sequence of amino acids extending from amino acid 274 to amino acid 681 of SEQ ID NO:12, inclusive and lacks the sequence that consists of the sequence extending from amino acid 1 to amino acid 273 and from amino acid 682 to amino acid 901 of SEQ ID NO:12.

7. The method of claim 1 wherein the catalytic domain comprises the sequence of amino acids extending from amino acid 290 to amino acid 666 of SEQ ID NO:12, inclusive and lacks the sequence that consists of the sequence extending from amino acid 1 to amino acid 289 and from amino acid 667 to amino acid 901 of SEQ ID NO:12.

8. The method of claim 1 wherein the catalytic domain comprises the sequence of amino acids extending from amino acid 290 to amino acid 681 of SEQ ID NO:12, inclusive and lacks the sequence that consists of the sequence extending from amino acid 1 to amino acid 289 and from amino acid 682 to amino acid 901 of SEQ ID NO:12.

9. The method of claim 1 wherein the fusion protein comprises an amino acid sequence selected from the group consisting of: SEQ ID NO:23, SEQ ID NO:25 and SEQ ID NO:27.

10. The method of claim 1 wherein the fusion protein comprises the amino acid sequence of SEQ ID NO:23.

11. The method of claim 1 wherein the fusion protein comprises the amino acid sequence of SEQ ID NO:25.

12. The method of claim 1 wherein the fusion protein comprises the amino acid sequence of SEQ ID NO:27.

13. The method of claim 1 wherein the step of providing a fusion protein comprises:
   (a) providing a cell harboring an expression vector comprising a nucleotide sequence encoding the fusion protein;
   (b) culturing the cell under conditions to express the polypeptide; and
   (c) purifying the expressed fusion protein.

14. The method of claim 13, wherein the cell is a eukaryotic cell.

15. The method of claim 13, wherein the cell is a prokaryotic cell.

16. The method of claim 13, wherein the prokaryotic cell is *E. coli*.

* * * * *

UNITED STATES PATENT AND TRADEMARK OFFICE
CERTIFICATE OF CORRECTION

PATENT NO. : 9,764,007 B2  Page 1 of 1
APPLICATION NO. : 14/954467
DATED : September 19, 2017
INVENTOR(S) : Fang Fang and Michael P. Malakhov It is certified that error appears in the above-identified patent and that said Letters Patent is hereby corrected as shown below:

Column 125, Line 3, Claim 16, delete "13," and insert -- 15, --

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 39

<210> SEQ ID NO 1
<211> LENGTH: 58
<212> TYPE: PRT
<213> ORGANISM: Bos taurus

<400> SEQUENCE: 1
```

```
Arg Pro Asp Phe Cys Leu Glu Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55
```

<210> SEQ ID NO 2
<211> LENGTH: 24
<212> TYPE: PRT
<213> ORGANISM: Homo sapiens

<400> SEQUENCE: 2

```
Asn Gly Arg Arg Ile Cys Leu Asp Leu Gln Ala Pro Leu Tyr Lys Lys
1               5                   10                  15

Ile Ile Lys Lys Leu Leu Glu Ser
            20
```

<210> SEQ ID NO 3
<211> LENGTH: 27
<212> TYPE: PRT
<213> ORGANISM: Homo sapiens

<400> SEQUENCE: 3

```
Gly Arg Glu Leu Cys Leu Asp Pro Lys Glu Asn Trp Val Gln Arg Val
1               5                   10                  15

Val Glu Lys Phe Leu Lys Arg Ala Glu Asn Ser
            20                  25
```

<210> SEQ ID NO 4
<211> LENGTH: 34
<212> TYPE: PRT
<213> ORGANISM: Homo sapiens

<400> SEQUENCE: 4

```
Gln Ile His Phe Phe Ala Lys Leu Asn Cys Arg Leu Tyr Arg Lys
1               5                   10                  15

Ala Asn Lys Ser Ser Lys Leu Val Ser Ala Asn Arg Leu Phe Gly Asp
            20                  25                  30

Lys Ser
```

<210> SEQ ID NO 5
<211> LENGTH: 34
<212> TYPE: PRT
<213> ORGANISM: Homo sapiens

<400> SEQUENCE: 5

```
Glu Leu Arg Val Arg Leu Ala Ser His Leu Arg Lys Leu Arg Lys Arg
1               5                   10                  15

Leu Leu Arg Asp Ala Asp Asp Leu Gln Lys Arg Leu Ala Val Tyr Gln
            20                  25                  30

Ala Gly
```

<210> SEQ ID NO 6
<211> LENGTH: 12
<212> TYPE: PRT
<213> ORGANISM: Homo sapiens

<400> SEQUENCE: 6

Arg Arg Leu Arg Arg Met Glu Ser Glu Ser Glu Ser
1               5                   10

<210> SEQ ID NO 7
<211> LENGTH: 21
<212> TYPE: PRT
<213> ORGANISM: Homo sapiens

<400> SEQUENCE: 7

Lys Arg Lys Lys Lys Gly Gly Lys Asn Gly Lys Asn Arg Arg Asn Arg
1               5                   10                  15

Lys Lys Lys Asn Pro
            20

<210> SEQ ID NO 8
<211> LENGTH: 379
<212> TYPE: PRT
<213> ORGANISM: Homo sapiens

<400> SEQUENCE: 8

Met Ala Ser Leu Pro Val Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu Asn Asp Arg Ala Arg Ser Leu Val Val
                165                 170                 175

Pro Ala Tyr Ala Tyr Arg Lys Leu His Pro Ile Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Gln Gly Cys
            260                 265                 270

Gln Gly Ser Val Ile Ser Phe Pro Ser Pro Arg Ser Gly Pro Gly Ser

```
              275                 280                 285
Pro Gln Trp Leu Leu Tyr Thr His Pro Thr His Ser Trp Gln Arg Ala
            290                 295                 300
Asp Leu Gly Ala Tyr Leu Asn Pro Arg Pro Ala Pro Glu Ala Trp
305                 310                 315                 320
Ser Glu Pro Val Leu Leu Ala Lys Gly Ser Cys Ala Tyr Ser Asp Leu
                325                 330                 335
Gln Ser Met Gly Thr Gly Pro Asp Gly Ser Pro Leu Phe Gly Cys Leu
            340                 345                 350
Tyr Glu Ala Asn Asp Tyr Glu Ile Val Phe Leu Met Phe Thr Leu
                355                 360                 365
Lys Gln Ala Phe Pro Ala Glu Tyr Leu Pro Gln
            370                 375

<210> SEQ ID NO 9
<211> LENGTH: 424
<212> TYPE: PRT
<213> ORGANISM: Homo sapiens

<400> SEQUENCE: 9

Leu Ala Gly Gly Ser Val Arg Trp Gly Ala Leu His Val Leu Gly Thr
  1               5                  10                  15
Ala Ala Leu Ala Glu His Arg Ser Met Asn Pro Cys Pro Val His Asp
                 20                  25                  30
Ala Gly Thr Gly Thr Val Phe Leu Phe Phe Ile Ala Val Leu Gly His
             35                  40                  45
Thr Pro Glu Ala Val Gln Ile Ala Thr Gly Arg Asn Ala Ala Arg Leu
 50                  55                  60
Cys Cys Val Ala Ser Arg Asp Ala Gly Leu Ser Trp Gly Ser Ala Arg
65                  70                  75                  80
Asp Leu Thr Glu Glu Ala Ile Gly Gly Ala Val Gln Asp Trp Ala Thr
                 85                  90                  95
Phe Ala Val Gly Pro Gly His Gly Val Gln Leu Pro Ser Gly Arg Leu
            100                 105                 110
Leu Val Pro Ala Tyr Thr Tyr Arg Val Asp Arg Leu Glu Cys Phe Gly
            115                 120                 125
Lys Ile Cys Arg Thr Ser Pro His Ser Phe Ala Phe Tyr Ser Asp Asp
130                 135                 140
His Gly Arg Thr Trp Arg Cys Gly Gly Leu Val Pro Asn Leu Arg Ser
145                 150                 155                 160
Gly Glu Cys Gln Leu Ala Ala Val Asp Gly Gly Gln Ala Gly Ser Phe
                165                 170                 175
Leu Tyr Cys Asn Ala Arg Ser Pro Leu Gly Ser Arg Val Gln Ala Leu
            180                 185                 190
Ser Thr Asp Glu Gly Thr Ser Phe Leu Pro Ala Glu Arg Val Ala Ser
            195                 200                 205
Leu Pro Glu Thr Ala Trp Gly Cys Gln Gly Ser Ile Val Gly Phe Pro
210                 215                 220
Ala Pro Ala Pro Asn Arg Pro Arg Asp Asp Ser Trp Ser Val Gly Pro
225                 230                 235                 240
Arg Ser Pro Leu Gln Pro Leu Leu Gly Pro Gly Val His Glu Pro
                245                 250                 255
Pro Glu Glu Ala Ala Val Asp Pro Arg Gly Gly Gln Val Pro Gly Gly
            260                 265                 270
```

```
Pro Phe Ser Arg Leu Gln Pro Arg Gly Asp Gly Pro Arg Gln Pro Gly
            275                 280                 285

Pro Arg Pro Gly Val Ser Gly Asp Val Gly Ser Trp Thr Leu Ala Leu
        290                 295                 300

Pro Met Pro Phe Ala Ala Pro Pro Gln Ser Pro Thr Trp Leu Leu Tyr
305                 310                 315                 320

Ser His Pro Val Gly Arg Arg Ala Arg Leu His Met Gly Ile Arg Leu
                325                 330                 335

Ser Gln Ser Pro Leu Asp Pro Arg Ser Trp Thr Glu Pro Trp Val Ile
            340                 345                 350

Tyr Glu Gly Pro Ser Gly Tyr Ser Asp Leu Ala Ser Ile Gly Pro Ala
        355                 360                 365

Pro Glu Gly Gly Leu Val Phe Ala Cys Leu Tyr Glu Ser Gly Ala Arg
    370                 375                 380

Thr Ser Tyr Asp Glu Ile Ser Phe Cys Thr Phe Ser Leu Arg Glu Val
385                 390                 395                 400

Leu Glu Asn Val Pro Ala Ser Pro Lys Pro Asn Leu Gly Asp Lys
                405                 410                 415

Pro Arg Gly Cys Cys Trp Pro Ser
            420

<210> SEQ ID NO 10
<211> LENGTH: 5
<212> TYPE: PRT
<213> ORGANISM: Artificial Sequence
<220> FEATURE:
<223> OTHER INFORMATION: Synthetically generated amino acid

<400> SEQUENCE: 10

Gly Gly Gly Gly Ser
 1               5

<210> SEQ ID NO 11
<211> LENGTH: 2706
<212> TYPE: DNA
<213> ORGANISM: Actinomyces viscosus

<400> SEQUENCE: 11
atgacatcgc atagtccttt ctcccggagg cgcctgccgg ccctcctggg ctccctgcca      60
ctggccgcca ccggcctgat cgccgccgca ccccgcgc acgccgtccc acgtctgac       120 ggcctggccg acgtcaccat cacgcaggtg aacgcgcccg cggacggcct ctactccgtc     180
ggcgatgtca tgaccttcaa catcaccctg accaacacca gcggcgaggc ccactcctac     240
gccccggcct cgacgaacct gtccgggaac gtctccaagt gccggtggcg caacgtcccg     300
gccgggacga ccaagaccga ctgcaccggc tggccacgc acacggtgac cgccgaggac     360
ctcaaggccg gtggcttcac cccgcagatc gcctacgagg tcaaggccgt ggagtacgcc     420
gggaaggccc tgagcacccc ggagacgatc aaggcgcga cgagcccagt caaggccaac     480
tcgctgcggg tcgagtcgat cacgccgtcg tcgagccagg agaactacaa gctgggcgac     540
accgtcagct acacggtgcg cgtgcgctcg gtgtcggaca agacgatcaa cgtcgccgcc     600
accgaatcct ccttcgacga cctgggccgc cagtgccact ggggcggcct caagccgggc     660
aagggcgccg tctacaactg caagccgctc acccacacga tcacgcaagc cgacgtcgac     720 gccgccgct ggacgccatc gatcaccctg acgccaccg aaccgacgg cgccaccctc      780 cagacgctca ccgccaccgg caaccccgatc aacgtcgtcg gcgaccaccc gcaggccacg     840
```

```
cccgcaccgg cgcccgacgc gagcacggag ctgccggcct caatgagcca ggcccagcac    900
ctggccgcca acacggccac cgacaactac cgcatcccgg cgatcaccac cgcccccaat    960
ggggacctgc tcatctccta cgacgagcgc ccgaaggaca acggcaacgg cggcagcgac   1020
gcccccaacc cgaaccacat cgtccagcgc cgctccaccg acggcggcaa gacctggtcg   1080
gcgcccacct acatccacca gggcacggag accggcaaga aggtcggcta ctccgacccg   1140
agctacgtcg tcgatcacca gacgggcacg atcttcaact tccacgtcaa gtcctacgac   1200
cagggctggg gcggctcgcg cggcggcacc gaccgggaga accggggcat catccaggcc   1260
gaggtgtcga cctccacgga caacggctgg acctggacgc accgcacgat caccgcggac   1320
atcacgaagg acaagccgtg gaccgcgcgt ttcgcggcct cgggccaggg catccagatt   1380
cagcacgggc cccacgccgg gcgcctggtg cagcagtaca cgatcaggac cgccggcggc   1440
gcggtgcagg ccgtctcggt ctactccgac gaccacggga agacgtggca ggccggcacg   1500
ccgatcggga ccggcatgga tgagaacaag gtcgttgagc tctccgacgg ctccctcatg   1560
ctcaactcgc gcgcctcgga tggctccggc ttccgcaagg tggcccactc caccgacggt   1620
gggcagacct ggagcgagcc ggtgtccgac aagaacctgc ccgactcggt ggacaacgcc   1680
cagatcatcc gagccttccc gaacgccgcg ccggacgacc cgcgcgccaa ggtgctgctg   1740
ctgagccact caccgaaccc gcggccgtgg tcgcgtgacc gcggcaccat ctcgatgtcc   1800
tgcgacgacg gcgcctcctg gacgaccagc aaggtcttcc acgagccctt cgtcggatac   1860
acgacgatcg cggtgcagtc cgacggcagc atcgggctgc tcagcgagga cgcccacaac   1920
ggcgccgact acgcggcat ctggtaccgc aacttcacga tgaactggct cggcgagcag   1980
tgcggccaga gccggcgga gccgagcccg gcgccgtcgc cgacggcggc accctcagcg   2040
gcaccgacgg agaagccggc cccgtcggcc gcgccgagcg ctgagcccac gcaggcaccg   2100
gcaccatcct ccgcgcccga gccgagcgct gcgcccgagc cgagcagcgc cccggcgccg   2160
gagcccacga ccgctccgag cacggagccc acaccggctc ctgcgcccag ctccgcacct   2220
gagcagaccg atgggccgac cgctgcgccc gcaccggaga cgtcctctgc accggccgcc   2280
gaaccgacgc aggccccgac ggtggcgcct tctgttgagc ccacgcaggc tccgggtgcg   2340
cagccgagct cagcacccaa gccggggcg acgggtcggg cccgtcggt ggtgaacccg   2400
aaggcgaccg gggcggcgac ggagcctggg acgccgtcat cgagcgcgag cccggcaccg   2460
agccggaacg cggcgccgac gccgaagccg ggcatggagc ccgatgagat tgatcggccg   2520
tctgacggca ccatggcgca gccgaccggt ggcgccagcg cgccgagtgc cgcgccgacg   2580
caggcggcga aggccggcag caggctgtct cgcacgggga ccaacgcgct gctgatcctg   2640
ggccttgcgg gtgtcgcggt tgtcggcggg tacctgctgc tgcgggctcg ccgttcgaag   2700
aactga                                                              2706
```

<210> SEQ ID NO 12
<211> LENGTH: 901
<212> TYPE: PRT
<213> ORGANISM: Actinomyces viscosus

<400> SEQUENCE: 12

Met Thr Ser His Ser Pro Phe Ser Arg Arg Leu Pro Ala Leu Leu
1               5                   10                  15

Gly Ser Leu Pro Leu Ala Ala Thr Gly Leu Ile Ala Ala Pro Pro
                20                  25                  30

Ala His Ala Val Pro Thr Ser Asp Gly Leu Ala Asp Val Thr Ile Thr

```
                35                  40                  45
Gln Val Asn Ala Pro Ala Asp Gly Leu Tyr Ser Val Gly Asp Val Met
                    50                  55                  60
Thr Phe Asn Ile Thr Leu Thr Asn Thr Ser Gly Glu Ala His Ser Tyr
 65                  70                  75                  80
Ala Pro Ala Ser Thr Asn Leu Ser Gly Asn Val Ser Lys Cys Arg Trp
                 85                  90                  95
Arg Asn Val Pro Ala Gly Thr Thr Lys Thr Asp Cys Thr Gly Leu Ala
                100                 105                 110
Thr His Thr Val Thr Ala Glu Asp Leu Lys Ala Gly Phe Thr Pro
             115                 120                 125
Gln Ile Ala Tyr Glu Val Lys Ala Val Glu Tyr Ala Gly Lys Ala Leu
             130                 135                 140
Ser Thr Pro Glu Thr Ile Lys Gly Ala Thr Ser Pro Val Lys Ala Asn
145                 150                 155                 160
Ser Leu Arg Val Glu Ser Ile Thr Pro Ser Ser Ser Gln Glu Asn Tyr
                165                 170                 175
Lys Leu Gly Asp Thr Val Ser Tyr Thr Val Arg Val Arg Ser Val Ser
             180                 185                 190
Asp Lys Thr Ile Asn Val Ala Ala Thr Glu Ser Ser Phe Asp Asp Leu
         195                 200                 205
Gly Arg Gln Cys His Trp Gly Gly Leu Lys Pro Gly Lys Gly Ala Val
210                 215                 220
Tyr Asn Cys Lys Pro Leu Thr His Thr Ile Thr Gln Ala Asp Val Asp
225                 230                 235                 240
Ala Gly Arg Trp Thr Pro Ser Ile Thr Leu Thr Ala Thr Gly Thr Asp
                245                 250                 255
Gly Ala Thr Leu Gln Thr Leu Thr Ala Thr Gly Asn Pro Ile Asn Val
             260                 265                 270
Val Gly Asp His Pro Gln Ala Thr Pro Ala Pro Ala Pro Asp Ala Ser
             275                 280                 285
Thr Glu Leu Pro Ala Ser Met Ser Gln Ala Gln His Leu Ala Ala Asn
         290                 295                 300
Thr Ala Thr Asp Asn Tyr Arg Ile Pro Ala Ile Thr Thr Ala Pro Asn
305                 310                 315                 320
Gly Asp Leu Leu Ile Ser Tyr Asp Glu Arg Pro Lys Asp Asn Gly Asn
                325                 330                 335
Gly Gly Ser Asp Ala Pro Asn Pro Asn His Ile Val Gln Arg Arg Ser
             340                 345                 350
Thr Asp Gly Gly Lys Thr Trp Ser Ala Pro Thr Tyr Ile His Gln Gly
             355                 360                 365
Thr Glu Thr Gly Lys Lys Val Gly Tyr Ser Asp Pro Ser Tyr Val Val
         370                 375                 380
Asp His Gln Thr Gly Thr Ile Phe Asn Phe His Val Lys Ser Tyr Asp
385                 390                 395                 400
Gln Gly Trp Gly Gly Ser Arg Gly Gly Thr Asp Pro Glu Asn Arg Gly
                405                 410                 415
Ile Ile Gln Ala Glu Val Ser Ser Thr Asp Asn Gly Trp Thr Trp
             420                 425                 430
Thr His Arg Thr Ile Thr Ala Asp Ile Thr Lys Asp Lys Pro Trp Thr
             435                 440                 445
Ala Arg Phe Ala Ala Ser Gly Gln Gly Ile Gln Ile Gln His Gly Pro
         450                 455                 460
```

```
His Ala Gly Arg Leu Val Gln Gln Tyr Thr Ile Arg Thr Ala Gly Gly
465                 470                 475                 480

Ala Val Gln Ala Val Ser Val Tyr Ser Asp Asp His Gly Lys Thr Trp
            485                 490                 495

Gln Ala Gly Thr Pro Ile Gly Thr Gly Met Asp Glu Asn Lys Val Val
        500                 505                 510

Glu Leu Ser Asp Gly Ser Leu Met Leu Asn Ser Arg Ala Ser Asp Gly
    515                 520                 525

Ser Gly Phe Arg Lys Val Ala His Ser Thr Asp Gly Gln Thr Trp
530                 535                 540

Ser Glu Pro Val Ser Asp Lys Asn Leu Pro Asp Ser Val Asp Asn Ala
545                 550                 555                 560

Gln Ile Ile Arg Ala Phe Pro Asn Ala Ala Pro Asp Asp Pro Arg Ala
                565                 570                 575

Lys Val Leu Leu Leu Ser His Ser Pro Asn Pro Arg Pro Trp Ser Arg
            580                 585                 590

Asp Arg Gly Thr Ile Ser Met Ser Cys Asp Asp Gly Ala Ser Trp Thr
        595                 600                 605

Thr Ser Lys Val Phe His Glu Pro Phe Val Gly Tyr Thr Thr Ile Ala
    610                 615                 620

Val Gln Ser Asp Gly Ser Ile Gly Leu Leu Ser Glu Asp Ala His Asn
625                 630                 635                 640

Gly Ala Asp Tyr Gly Gly Ile Trp Tyr Arg Asn Phe Thr Met Asn Trp
                645                 650                 655

Leu Gly Glu Gln Cys Gly Gln Lys Pro Ala Pro Ser Pro Ala Pro
            660                 665                 670

Ser Pro Thr Ala Ala Pro Ser Ala Ala Pro Thr Glu Lys Pro Ala Pro
        675                 680                 685

Ser Ala Ala Pro Ser Ala Glu Pro Thr Gln Ala Pro Ala Pro Ser Ser
690                 695                 700

Ala Pro Glu Pro Ser Ala Ala Pro Glu Pro Ser Ser Ala Pro Ala Pro
705                 710                 715                 720

Glu Pro Thr Thr Ala Pro Ser Thr Glu Pro Thr Pro Ala Pro Ala Pro
            725                 730                 735

Ser Ser Ala Pro Glu Gln Thr Asp Gly Pro Thr Ala Ala Pro Ala Pro
        740                 745                 750

Glu Thr Ser Ser Ala Pro Ala Ala Glu Pro Thr Gln Ala Pro Thr Val
    755                 760                 765

Ala Pro Ser Val Glu Pro Thr Gln Ala Pro Gly Ala Gln Pro Ser Ser
        770                 775                 780

Ala Pro Lys Pro Gly Ala Thr Gly Arg Ala Pro Ser Val Val Asn Pro
785                 790                 795                 800

Lys Ala Thr Gly Ala Ala Thr Glu Pro Gly Thr Pro Ser Ser Ser Ala
            805                 810                 815

Ser Pro Ala Pro Ser Arg Asn Ala Ala Pro Thr Pro Lys Pro Gly Met
        820                 825                 830

Glu Pro Asp Glu Ile Asp Arg Pro Ser Asp Gly Thr Met Ala Gln Pro
    835                 840                 845

Thr Gly Gly Ala Ser Ala Pro Ser Ala Ala Pro Thr Gln Ala Ala Lys
    850                 855                 860

Ala Gly Ser Arg Leu Ser Arg Thr Gly Thr Asn Ala Leu Leu Ile Leu
865                 870                 875                 880
```

Gly Leu Ala Gly Val Ala Val Val Gly Gly Tyr Leu Leu Leu Arg Ala
            885                 890                 895

Arg Arg Ser Lys Asn
        900

<210> SEQ ID NO 13
<211> LENGTH: 1887
<212> TYPE: DNA
<213> ORGANISM: Actinomyces viscosus

<400> SEQUENCE: 13

```
ggcgaccacc cgcaggccac gcccgcaccg gcgcccgacg cgagcacgga gctgccggcc      60
tcaatgagcc aggcccagca cctggccgcc aacacggcca ccgacaacta ccgcatcccg     120
gcgatcacca ccgcccccaa tggggacctg ctcatctcct acgacgagcg cccgaaggac     180
aacggcaacg gcggcagcga cgcccccaac ccgaaccaca tcgtccagcg ccgctccacc     240
gacggcggca agacctggtc ggcgcccacc tacatccacc agggcacgga gaccggcaag     300
aaggtcggct actccgaccc gagctacgtc gtcgatcacc agacgggcac gatcttcaac     360
ttccacgtca gtcctacga ccagggctgg ggcggctcgc gcggcggcac cgacccggag     420
aaccggggca tcatccaggc cgaggtgtcg acctccacgg acaacggctg gacctggacg     480
caccgcacga tcaccgcgga catcacgaag acaagccgt ggaccgcgcg tttcgcggcc     540
tcgggccagg gcatccagat tcagcacggg ccccacgccg ggcgcctggt gcagcagtac     600
acgatcagga ccgccggcgg cgcggtgcag gccgtctcgg tctactccga cgaccacggg     660
aagacgtggc aggccggcac gccgatcggg accggcatgg atgagaacaa ggtcgttgag     720
ctctccgacg gctccctcat gctcaactcg cgcgcctcgg atggctccgg cttccgcaag     780
gtggcccact ccaccgacgg tgggcagacc tggagcgagc cggtgtccga caagaacctg     840
cccgactcgg tggacaacgc ccagatcatc cgagccttcc cgaacgccgc gccggacgac     900
ccgcgcgcca aggtgctgct gctgagccac tcaccgaacc cgcggccgtg gtcgcgtgac     960
cgcggcacca tctcgatgtc ctgcgacgac ggcgcctcct ggacgaccag caaggtcttc    1020
cacgagccct tcgtcggata cacgacgatc gcggtgcagt ccgacggcag catcgggctg    1080
ctcagcgagg acgcccacaa cggcgccgac tacgcggca tctggtaccg caacttcacg    1140
atgaactggc tcggcgagca gtgcggccag aagccggcgg agccgagccc ggcgccgtcg    1200
ccgacggcgg caccctcagc ggcaccgacg gagaagccgg cccgtcggc cgcgccgagc    1260
gctgagccca cgcaggcacc ggcaccatcc tccgcgcccg agccgagcgc tgcgcccgag    1320
ccgagcagcg ccccggcgcc ggagcccacg accgctccga gcacggagcc cacaccggct    1380
cctgcgccca gctccgcacc tgagcagacc gatgggccga ccgctgcgcc cgcaccggag    1440
acgtcctctg caccggccgc cgaaccgacg caggcccga cggtggcgcc ttctgttgag    1500
cccacgcagg ctccgggtgc gcagccgagc tcagcaccca agccggggc gacgggtcgg    1560
gccccgtcgg tggtgaaccc gaaggcgacc ggggcggcga cggagcctgg gacgccgtca    1620
tcgagcgcga gcccggcacc gagccggaac gcggcgccga cgccgaagcc gggcatggag    1680
cccgatgaga ttgatcggcc gtctgacggc catggcgc agccgaccgg tggcgccagc    1740
gcgccgagtg ccgcgccgac gcaggcggcg aaggccggca gcaggctgtc tcgcacgggg    1800
accaacgcgc tgctgatcct gggccttgcg ggtgtcgcgg ttgtcggcgg gtacctgctg    1860
ctgcgggctc gccgttcgaa gaactga                                       1887
```

```
<210> SEQ ID NO 14
<211> LENGTH: 628
<212> TYPE: PRT
<213> ORGANISM: Actinomyces viscosus

<400> SEQUENCE: 14
```

| | | | | | | | | | | | | | | |
|---|---|---|---|---|---|---|---|---|---|---|---|---|---|---|
| Gly | Asp | His | Pro | Gln | Ala | Thr | Pro | Ala | Pro | Ala | Pro | Asp | Ala | Ser | Thr |
| 1 | | | | 5 | | | | | 10 | | | | | 15 | |
| Glu | Leu | Pro | Ala | Ser | Met | Ser | Gln | Ala | Gln | His | Leu | Ala | Ala | Asn | Thr |
| | | | 20 | | | | | 25 | | | | | 30 | | |
| Ala | Thr | Asp | Asn | Tyr | Arg | Ile | Pro | Ala | Ile | Thr | Thr | Ala | Pro | Asn | Gly |
| | | | 35 | | | | | 40 | | | | | 45 | | |
| Asp | Leu | Leu | Ile | Ser | Tyr | Asp | Glu | Arg | Pro | Lys | Asp | Asn | Gly | Asn | Gly |
| | 50 | | | | | 55 | | | | | 60 | | | | |
| Gly | Ser | Asp | Ala | Pro | Asn | Pro | Asn | His | Ile | Val | Gln | Arg | Arg | Ser | Thr |
| 65 | | | | | 70 | | | | | 75 | | | | | 80 |
| Asp | Gly | Gly | Lys | Thr | Trp | Ser | Ala | Pro | Thr | Tyr | Ile | His | Gln | Gly | Thr |
| | | | | 85 | | | | | 90 | | | | | 95 | |
| Glu | Thr | Gly | Lys | Lys | Val | Gly | Tyr | Ser | Asp | Pro | Ser | Tyr | Val | Val | Asp |
| | | | | 100 | | | | | 105 | | | | | 110 | |
| His | Gln | Thr | Gly | Thr | Ile | Phe | Asn | Phe | His | Val | Lys | Ser | Tyr | Asp | Gln |
| | | | | 115 | | | | | 120 | | | | | 125 | |
| Gly | Trp | Gly | Gly | Ser | Arg | Gly | Gly | Thr | Asp | Pro | Glu | Asn | Arg | Gly | Ile |
| | | 130 | | | | | 135 | | | | | 140 | | | |
| Ile | Gln | Ala | Glu | Val | Ser | Thr | Ser | Thr | Asp | Asn | Gly | Trp | Thr | Trp | Thr |
| 145 | | | | | 150 | | | | | 155 | | | | | 160 |
| His | Arg | Thr | Ile | Thr | Ala | Asp | Ile | Thr | Lys | Asp | Lys | Pro | Trp | Thr | Ala |
| | | | | 165 | | | | | 170 | | | | | 175 | |
| Arg | Phe | Ala | Ala | Ser | Gly | Gln | Gly | Ile | Gln | Ile | Gln | His | Gly | Pro | His |
| | | | 180 | | | | | 185 | | | | | 190 | | |
| Ala | Gly | Arg | Leu | Val | Gln | Gln | Tyr | Thr | Ile | Arg | Thr | Ala | Gly | Gly | Ala |
| | | | 195 | | | | | 200 | | | | | 205 | | |
| Val | Gln | Ala | Val | Ser | Val | Tyr | Ser | Asp | Asp | His | Gly | Lys | Thr | Trp | Gln |
| | 210 | | | | | 215 | | | | | 220 | | | | |
| Ala | Gly | Thr | Pro | Ile | Gly | Thr | Gly | Met | Asp | Glu | Asn | Lys | Val | Val | Glu |
| 225 | | | | | 230 | | | | | 235 | | | | | 240 |
| Leu | Ser | Asp | Gly | Ser | Leu | Met | Leu | Asn | Ser | Arg | Ala | Ser | Asp | Gly | Ser |
| | | | | 245 | | | | | 250 | | | | | 255 | |
| Gly | Phe | Arg | Lys | Val | Ala | His | Ser | Thr | Asp | Gly | Gly | Gln | Thr | Trp | Ser |
| | | | 260 | | | | | 265 | | | | | 270 | | |
| Glu | Pro | Val | Ser | Asp | Lys | Asn | Leu | Pro | Asp | Ser | Val | Asp | Asn | Ala | Gln |
| | | | 275 | | | | | 280 | | | | | 285 | | |
| Ile | Ile | Arg | Ala | Phe | Pro | Asn | Ala | Ala | Pro | Asp | Pro | Arg | Ala | Lys |
| | 290 | | | | | 295 | | | | | 300 | | | | |
| Val | Leu | Leu | Leu | Ser | His | Ser | Pro | Asn | Pro | Arg | Pro | Trp | Ser | Arg | Asp |
| 305 | | | | | 310 | | | | | 315 | | | | | 320 |
| Arg | Gly | Thr | Ile | Ser | Met | Ser | Cys | Asp | Asp | Gly | Ala | Ser | Trp | Thr | Thr |
| | | | | 325 | | | | | 330 | | | | | 335 | |
| Ser | Lys | Val | Phe | His | Glu | Pro | Phe | Val | Gly | Tyr | Thr | Thr | Ile | Ala | Val |
| | | | 340 | | | | | 345 | | | | | 350 | | |
| Gln | Ser | Asp | Gly | Ser | Ile | Gly | Leu | Leu | Ser | Glu | Asp | Ala | His | Asn | Gly |
| | | | 355 | | | | | 360 | | | | | 365 | | |
| Ala | Asp | Tyr | Gly | Gly | Ile | Trp | Tyr | Arg | Asn | Phe | Thr | Met | Asn | Trp | Leu |
| | 370 | | | | | 375 | | | | | 380 | | | | |

Gly Glu Gln Cys Gly Gln Lys Pro Ala Glu Pro Ser Pro Ala Pro Ser
385                 390                 395                 400

Pro Thr Ala Ala Pro Ser Ala Ala Pro Thr Glu Lys Pro Ala Pro Ser
            405                 410                 415

Ala Ala Pro Ser Ala Glu Pro Thr Gln Ala Pro Ala Pro Ser Ser Ala
        420                 425                 430

Pro Glu Pro Ser Ala Ala Pro Glu Pro Ser Ser Ala Pro Ala Pro Glu
    435                 440                 445

Pro Thr Thr Ala Pro Ser Thr Glu Pro Thr Pro Ala Pro Ala Pro Ser
        450                 455                 460

Ser Ala Pro Glu Gln Thr Asp Gly Pro Thr Ala Ala Pro Ala Pro Glu
465                 470                 475                 480

Thr Ser Ser Ala Pro Ala Ala Glu Pro Thr Gln Ala Pro Thr Val Ala
            485                 490                 495

Pro Ser Val Glu Pro Thr Gln Ala Pro Gly Ala Gln Pro Ser Ser Ala
        500                 505                 510

Pro Lys Pro Gly Ala Thr Gly Arg Ala Pro Ser Val Val Asn Pro Lys
    515                 520                 525

Ala Thr Gly Ala Ala Thr Glu Pro Gly Thr Pro Ser Ser Ser Ala Ser
        530                 535                 540

Pro Ala Pro Ser Arg Asn Ala Ala Pro Thr Pro Lys Pro Gly Met Glu
545                 550                 555                 560

Pro Asp Glu Ile Asp Arg Pro Ser Asp Gly Thr Met Ala Gln Pro Thr
            565                 570                 575

Gly Gly Ala Ser Ala Pro Ser Ala Ala Pro Thr Gln Ala Ala Lys Ala
        580                 585                 590

Gly Ser Arg Leu Ser Arg Thr Gly Thr Asn Ala Leu Leu Ile Leu Gly
    595                 600                 605

Leu Ala Gly Val Ala Val Val Gly Gly Tyr Leu Leu Leu Arg Ala Arg
        610                 615                 620

Arg Ser Lys Asn
625

<210> SEQ ID NO 15
<211> LENGTH: 1182
<212> TYPE: DNA
<213> ORGANISM: Artificial Sequence
<220> FEATURE:
<223> OTHER INFORMATION: Synthetically generated nucleic acid

<400> SEQUENCE: 15
ggagatcatc cacaagctac accagcacct gcaccagatg ctagcactga gctgccagca      60
agcatgtctc aggctcagca tcttgcagca aatacggcta ctgataatta tcgcattcca     120
gcgattacaa ccgctccgaa tggtgattta ctgattagct atgatgaacg gccgaaggac     180
aatggaaatg gtggttccga tgcccctaac ccgaatcata ttgttcagcg tcgctccaca     240
gatggcggta aacttggag cgcgccaacc tatattcatc agggtacgga gactggcaag     300
aaagtgggat attccgaccc ctcttatgtg gtggatcatc aaaccggtac aatcttcaat     360
tttcatgtga atcatacga tcagggctgg gaggtagcc gtggggaac agacccggaa     420 aaccgcggga ttattcaggc agaggtgtct acgagcacgg ataatggatg acgtggaca     480 catcgcacca tcaccgcgga tattacgaaa gataaaccgt ggaccgcgcg ttttgcggcg     540
tccggccaag gcattcagat ccagcatggg ccgcatgccg ccgtctggt gcaacagtat     600 accattcgta cggccggtgg agcggtgcag gctgtatcgg tttattccga tgatcatggg     660

```
aaaacgtggc aggctggcac cccgattggg acgggtatgg atgaaaacaa agttgtagag    720
ctgtctgacg gctctctgat gctgaacagt cgtgcgtcgg acgggagcgg ctttcgtaag    780
gttgcgcata gcactgatgg tgggcagacc tggtccgaac cggtttcgga caaaaatttg    840
ccggattcgg ttgataatgc ccagataatt cgtgcgtttc ctaatgctgc ccccgatgac    900
ccgcgcgcga aagtacttct tctgagtcat tccccaaatc cacgtccgtg gtcccgggat    960
cgtggtacga taagcatgtc atgtgatgac ggggcctcat ggaccacttc caaagttttt   1020
cacgaaccgt ttgtgggcta cacgactatt gcagttcaga gtgatggaag catcggtctg   1080 ctgtcgagg acgcgcacaa tggcgctgat tatggtggca tctggtatcg taattttacg    1140
atgaactggc tgggagaaca atgtggacaa aaacccgcgg aa                      1182

<210> SEQ ID NO 16
<211> LENGTH: 394
<212> TYPE: PRT
<213> ORGANISM: Actinomyces viscosus

<400> SEQUENCE: 16

Gly Asp His Pro Gln Ala Thr Pro Ala Pro Ala Pro Asp Ala Ser Thr
 1               5                  10                  15

Glu Leu Pro Ala Ser Met Ser Gln Ala Gln His Leu Ala Ala Asn Thr
                20                  25                  30

Ala Thr Asp Asn Tyr Arg Ile Pro Ala Ile Thr Thr Ala Pro Asn Gly
            35                  40                  45

Asp Leu Leu Ile Ser Tyr Asp Glu Arg Pro Lys Asp Asn Gly Asn Gly
        50                  55                  60

Gly Ser Asp Ala Pro Asn Pro Asn His Ile Val Gln Arg Arg Ser Thr
65                  70                  75                  80

Asp Gly Gly Lys Thr Trp Ser Ala Pro Thr Tyr Ile His Gln Gly Thr
                85                  90                  95

Glu Thr Gly Lys Lys Val Gly Tyr Ser Asp Pro Ser Tyr Val Val Asp
               100                 105                 110

His Gln Thr Gly Thr Ile Phe Asn Phe His Val Lys Ser Tyr Asp Gln
           115                 120                 125

Gly Trp Gly Gly Ser Arg Gly Gly Thr Asp Pro Glu Asn Arg Gly Ile
       130                 135                 140

Ile Gln Ala Glu Val Ser Thr Ser Thr Asp Asn Gly Trp Thr Trp Thr
145                 150                 155                 160

His Arg Thr Ile Thr Ala Asp Ile Thr Lys Asp Lys Pro Trp Thr Ala
                165                 170                 175

Arg Phe Ala Ala Ser Gly Gln Gly Ile Gln Ile Gln His Gly Pro His
            180                 185                 190

Ala Gly Arg Leu Val Gln Gln Tyr Thr Ile Arg Thr Ala Gly Gly Ala
        195                 200                 205

Val Gln Ala Val Ser Val Tyr Ser Asp His Gly Lys Thr Trp Gln
    210                 215                 220

Ala Gly Thr Pro Ile Gly Thr Gly Met Asp Glu Asn Lys Val Val Glu
225                 230                 235                 240

Leu Ser Asp Gly Ser Leu Met Leu Asn Ser Arg Ala Ser Asp Gly Ser
                245                 250                 255

Gly Phe Arg Lys Val Ala His Ser Thr Asp Gly Gly Gln Thr Trp Ser
            260                 265                 270

Glu Pro Val Ser Asp Lys Asn Leu Pro Asp Ser Val Asp Asn Ala Gln
```

```
                275                 280                 285
Ile Ile Arg Ala Phe Pro Asn Ala Ala Pro Asp Asp Pro Arg Ala Lys
    290                 295                 300

Val Leu Leu Leu Ser His Ser Pro Asn Pro Arg Pro Trp Ser Arg Asp
305                 310                 315                 320

Arg Gly Thr Ile Ser Met Ser Cys Asp Asp Gly Ala Ser Trp Thr Thr
                325                 330                 335

Ser Lys Val Phe His Glu Pro Phe Val Gly Tyr Thr Thr Ile Ala Val
            340                 345                 350

Gln Ser Asp Gly Ser Ile Gly Leu Leu Ser Glu Asp Ala His Asn Gly
        355                 360                 365

Ala Asp Tyr Gly Gly Ile Trp Tyr Arg Asn Phe Thr Met Asn Trp Leu
    370                 375                 380

Gly Glu Gln Cys Gly Gln Lys Pro Ala Glu
385                 390

<210> SEQ ID NO 17
<211> LENGTH: 6
<212> TYPE: PRT
<213> ORGANISM: Artificial Sequence
<220> FEATURE:
<223> OTHER INFORMATION: Synthetically generated amino acid

<400> SEQUENCE: 17

Met Val Lys Arg Lys Lys
 1               5

<210> SEQ ID NO 18
<211> LENGTH: 1281
<212> TYPE: DNA
<213> ORGANISM: Artificial Sequence
<220> FEATURE:
<223> OTHER INFORMATION: Synthetically generated nucleic acid

<400> SEQUENCE: 18
ccatggttaa gcgcaaaaaa aaaggcggca aaaacggtaa aaatcgtcgt aaccgtaaga      60
aaaaaaatcc tggagatcat ccacaagcta caccagcacc tgcaccagat gctagcactg     120
agctgccagc aagcatgtct caggctcagc atcttgcagc aaatacggct actgataatt     180
atcgcattcc agcgattaca accgctccga atggtgattt actgattagc tatgatgaac     240
ggccgaagga caatggaaat ggtggttccg atgcccctaa cccgaatcat attgttcagc     300
gtcgctccac agatggcggt aaacttggag cgcgccaac ctatattcat cagggtacgg     360
agactggcaa gaaagtggga tattccgacc cctcttatgt ggtggatcat caaaccggta     420
caatcttcaa ttttcatgtg aaatcatacg atcagggctg gggaggtagc cgtgggggaa     480
cagacccgga aaaccgcggg attattcagg cagaggtgtc tacgagcacg gataatggat     540
ggacgtggac acatcgcacc atcaccgcgg atattacgaa agataaaccg tggaccgcgc     600
gttttgcggc gtccggccaa ggcattcaga tccagcatgg gccgcatgcc ggccgtctgg     660
tgcaacagta taccattcgt acggccggtg agcggtgca ggctgtatcg gtttattccg     720
atgatcatgg gaaacgtgg caggctggca cccgattgg gacgggtatg atgaaaaca     780 aagttgtaga gctgtctgac ggctctctga tgctgaacag tcgtgcgtcg acgggagcg     840 gctttcgtaa ggttgcgcat agcactgatg gtgggcagac ctggtccgaa ccggtttcgg     900
acaaaaattt gccggattcg gttgataatg cccagataat tcgtgcgttt cctaatgctg     960
cccccgatga cccgcgcgcg aaagtacttc ttctgagtca ttccccaaat ccacgtccgt    1020
```

```
ggtcccggga tcgtggtacg ataagcatgt catgtgatga cggggcctca tggaccactt    1080
ccaaagtttt tcacgaaccg tttgtgggct acacgactat tgcagttcag agtgatggaa    1140
gcatcggtct gctgtcggag gacgcgcaca atggcgctga ttatggtggc atctggtatc    1200
gtaattttac gatgaactgg ctgggagaac aatgtggaca aaaacccgcg gaataagctt    1260
aaaaacccgc ggaataagct t                                              1281
```

<210> SEQ ID NO 19
<211> LENGTH: 444
<212> TYPE: PRT
<213> ORGANISM: Artificial Sequence
<220> FEATURE:
<223> OTHER INFORMATION: Synthetically generated amino acid

<400> SEQUENCE: 19

```
Met Val Lys Arg Lys Lys Gly Gly Lys Asn Gly Lys Asn Arg Arg
 1               5                  10                  15

Asn Arg Lys Lys Lys Asn Pro Gly Asp His Pro Gln Ala Thr Pro Ala
            20                  25                  30

Pro Ala Pro Asp Ala Ser Thr Glu Leu Pro Ala Ser Met Ser Gln Ala
        35                  40                  45

Gln His Leu Ala Ala Asn Thr Ala Thr Asp Asn Tyr Arg Ile Pro Ala
    50                  55                  60

Ile Thr Thr Ala Pro Asn Gly Asp Leu Leu Ile Ser Tyr Asp Glu Arg
65                  70                  75                  80

Pro Lys Asp Asn Gly Asn Gly Gly Ser Asp Ala Pro Asn Pro Asn His
                85                  90                  95

Ile Val Gln Arg Arg Ser Thr Asp Gly Gly Lys Thr Trp Ser Ala Pro
            100                 105                 110

Thr Tyr Ile His Gln Gly Thr Glu Thr Gly Lys Lys Val Gly Tyr Ser
        115                 120                 125

Asp Pro Ser Tyr Val Val Asp His Gln Thr Gly Thr Ile Phe Asn Phe
    130                 135                 140

His Val Lys Ser Tyr Asp Gln Gly Trp Gly Gly Ser Arg Gly Gly Thr
145                 150                 155                 160

Asp Pro Glu Asn Arg Gly Ile Ile Gln Ala Glu Val Ser Thr Ser Thr
                165                 170                 175

Asp Asn Gly Trp Thr Trp Thr His Arg Thr Ile Thr Ala Asp Ile Thr
            180                 185                 190

Lys Asp Lys Pro Trp Thr Ala Arg Phe Ala Ala Ser Gly Gln Gly Ile
        195                 200                 205

Gln Ile Gln His Gly Pro His Ala Gly Arg Leu Val Gln Gln Tyr Thr
    210                 215                 220

Ile Arg Thr Ala Gly Gly Ala Val Gln Ala Val Ser Val Tyr Ser Asp
225                 230                 235                 240

Asp His Gly Lys Thr Trp Gln Ala Gly Thr Pro Ile Gly Thr Gly Met
                245                 250                 255

Asp Glu Asn Lys Val Val Glu Leu Ser Asp Gly Ser Leu Met Leu Asn
            260                 265                 270

Ser Arg Ala Ser Asp Gly Ser Gly Phe Arg Lys Val Ala His Ser Thr
        275                 280                 285

Asp Gly Gly Gln Thr Trp Ser Glu Pro Val Ser Asp Lys Asn Leu Pro
    290                 295                 300

Asp Ser Val Asp Asn Ala Gln Ile Ile Arg Ala Phe Pro Asn Ala Ala
```

|  |  | 305 |  |  | 310 |  |  | 315 |  |  | 320 |
|---|---|---|---|---|---|---|---|---|---|---|---|

Pro Asp Asp Pro Arg Ala Lys Val Leu Leu Leu Ser His Ser Pro Asn
                          325                      330                     335

Pro Arg Pro Trp Ser Arg Asp Arg Gly Thr Ile Ser Met Ser Cys Asp
                 340                        345                      350

Asp Gly Ala Ser Trp Thr Thr Ser Lys Val Phe His Glu Pro Phe Val
               355                        360                      365

Gly Tyr Thr Thr Ile Ala Val Gln Ser Asp Gly Ser Ile Gly Leu Leu
    370                        375                      380

Ser Glu Asp Ala His Asn Gly Ala Asp Tyr Gly Gly Ile Trp Tyr Arg
385                        390                      395                      400

Asn Phe Thr Met Asn Trp Leu Gly Glu Gln Cys Gly Gln Lys Pro Ala
                   405                        410                      415

Glu Gly Ala Asp Tyr Gly Gly Ile Trp Tyr Arg Asn Phe Thr Met Asn
               420                        425                      430

Trp Leu Gly Glu Gln Cys Gly Gln Lys Pro Ala Glu
          435                        440

<210> SEQ ID NO 20
<211> LENGTH: 1248
<212> TYPE: DNA
<213> ORGANISM: Artificial Sequence
<220> FEATURE:
<223> OTHER INFORMATION: Synthetically generated nucleic acid

<400> SEQUENCE: 20

```
atgggagatc atccacaagc tacaccagca cctgcaccag atgctagcac tgagctgcca      60
gcaagcatgt ctcaggctca gcatcttgca gcaaatacgg ctactgataa ttatcgcatt     120
ccagcgatta caaccgctcc gaatggtgat ttactgatta gctatgatga acggccgaag     180
gacaatggaa atggtggttc gatgcccct aacccgaatc atattgttca gcgtcgctcc      240
acagatggcg gtaaaacttg gagcgcgcca acctatattc atcagggtac ggagactggc     300
aagaaagtgg atattccga ccctcttat gtggtggatc atcaaaccgg tacaatcttc       360
aattttcatg tgaaatcata cgatcaggcc tggggaggta gcgtgggg aacagacccg       420
gaaaaccgcg ggattattca ggcagaggtg tctacgagca cggataatgg atggacgtgg     480
acacatcgca ccatcaccgc ggatattacg aaagataaac cgtggaccgc gcgttttgcg     540
gcgtccggcc aaggcattca gatccagcat gggccgcatg ccggccgtct ggtgcaacag     600
tataccattc gtacggccgg tggagcggtg caggctgtat cggtttattc cgatgatcat     660
gggaaaacgt ggcaggctgg cacccccgatt gggacgggta tggatgaaaa caaagttgta    720
gagctgtctg acggctctct gatgctgaac agtcgtgcgt cggacgggag cggctttcgt    780
aaggttgcgc atagcactga tggtgggcag acctggtccg aaccggtttc ggacaaaaat    840
ttgccggatt cggttgataa tgcccagata attcgtgcgt ttcctaatgc tgcccccgat    900
gacccgcgcg cgaaagtact tcttctgagt cattccccaa atccacgtcc gtggtcccgg    960
gatcgtggta cgataagcat gtcatgtgat gacggggcct catggaccac ttccaaagtt   1020
tttcacgaac cgtttgtggg ctacacgact attgcagttc agagtgatgg aagcatcggt   1080
ctgctgtcgg aggacgcgca caatggcgct gattatggtg gcatctggta tcgtaatttt   1140
acgatgaact ggctgggaga acaatgtgga caaaaacccg cgaagcgcaa aaaaaaggc   1200
ggcaaaaacg gtaaaaatcg tcgtaaccgt aagaaaaaaa atccttga              1248
```

<210> SEQ ID NO 21
<211> LENGTH: 415
<212> TYPE: PRT
<213> ORGANISM: Artificial Sequence
<220> FEATURE:
<223> OTHER INFORMATION: Synthetically generated amino acid

<400> SEQUENCE: 21

```
Met Gly Asp His Pro Gln Ala Thr Pro Ala Pro Asp Ala Ser
 1               5                  10                  15

Thr Glu Leu Pro Ala Ser Met Ser Gln Ala Gln His Leu Ala Ala Asn
                20                  25                  30

Thr Ala Thr Asp Asn Tyr Arg Ile Pro Ala Ile Thr Thr Ala Pro Asn
                35                  40                  45

Gly Asp Leu Leu Ile Ser Tyr Asp Glu Arg Pro Lys Asp Asn Gly Asn
            50                  55                  60

Gly Gly Ser Asp Ala Pro Asn Pro Asn His Ile Val Gln Arg Arg Ser
65                  70                  75                  80

Thr Asp Gly Gly Lys Thr Trp Ser Ala Pro Thr Tyr Ile His Gln Gly
                85                  90                  95

Thr Glu Thr Gly Lys Lys Val Gly Tyr Ser Asp Pro Ser Tyr Val Val
               100                 105                 110

Asp His Gln Thr Gly Thr Ile Phe Asn Phe His Val Lys Ser Tyr Asp
                115                 120                 125

Gln Gly Trp Gly Gly Ser Arg Gly Gly Thr Asp Pro Glu Asn Arg Gly
            130                 135                 140

Ile Ile Gln Ala Glu Val Ser Thr Ser Thr Asp Asn Gly Trp Thr Trp
145                 150                 155                 160

Thr His Arg Thr Ile Thr Ala Asp Ile Thr Lys Asp Lys Pro Trp Thr
                165                 170                 175

Ala Arg Phe Ala Ala Ser Gly Gln Gly Ile Gln Ile Gln His Gly Pro
                180                 185                 190

His Ala Gly Arg Leu Val Gln Gln Tyr Thr Ile Arg Thr Ala Gly Gly
            195                 200                 205

Ala Val Gln Ala Val Ser Val Tyr Ser Asp Asp His Gly Lys Thr Trp
210                 215                 220

Gln Ala Gly Thr Pro Ile Gly Thr Gly Met Asp Glu Asn Lys Val Val
225                 230                 235                 240

Glu Leu Ser Asp Gly Ser Leu Met Leu Asn Ser Arg Ala Ser Asp Gly
                245                 250                 255

Ser Gly Phe Arg Lys Val Ala His Ser Thr Asp Gly Gly Gln Thr Trp
            260                 265                 270

Ser Glu Pro Val Ser Asp Lys Asn Leu Pro Asp Ser Val Asp Asn Ala
            275                 280                 285

Gln Ile Ile Arg Ala Phe Pro Asn Ala Ala Pro Asp Asp Pro Arg Ala
            290                 295                 300

Lys Val Leu Leu Leu Ser His Ser Pro Asn Pro Arg Pro Trp Ser Arg
305                 310                 315                 320

Asp Arg Gly Thr Ile Ser Met Ser Cys Asp Asp Gly Ala Ser Trp Thr
                325                 330                 335

Thr Ser Lys Val Phe His Glu Pro Phe Val Gly Tyr Thr Thr Ile Ala
                340                 345                 350

Val Gln Ser Asp Gly Ser Ile Gly Leu Leu Ser Glu Asp Ala His Asn
            355                 360                 365

Gly Ala Asp Tyr Gly Gly Ile Trp Tyr Arg Asn Phe Thr Met Asn Trp
```

Leu Gly Glu Gln Cys Gly Gln Lys Pro Ala Lys Arg Lys Lys Gly
385                 390                 395                 400

Gly Lys Asn Gly Lys Asn Arg Arg Asn Arg Lys Lys Asn Pro
            405                 410                 415

<210> SEQ ID NO 22
<211> LENGTH: 1293
<212> TYPE: DNA
<213> ORGANISM: Artificial Sequence
<220> FEATURE:
<223> OTHER INFORMATION: Synthetically generated nucleic acid

<400> SEQUENCE: 22

| | | | | | |
|---|---|---|---|---|---|
| atgggagatc | atccacaagc | tacaccagca | cctgcaccag | atgctagcac | tgagctgcca | 60 |
| gcaagcatgt | ctcaggctca | gcatcttgca | gcaaatacgg | ctactgataa | ttatcgcatt | 120 |
| ccagcgatta | caaccgctcc | gaatggtgat | ttactgatta | gctatgatga | acggccgaag | 180 |
| gacaatggaa | atggtggttc | cgatgcccct | aacccgaatc | atattgttca | gcgtcgctcc | 240 |
| acagatggcg | gtaaaacttg | gagcgcgcca | acctatattc | atcagggtac | ggagactggc | 300 |
| aagaaagtgg | atattccga | cccctcttat | gtggtggatc | atcaaaccgg | tacaatcttc | 360 |
| aattttcatg | tgaaatcata | cgatcagggc | tggggaggta | gccgtggggg | aacagacccg | 420 |
| gaaaaccgcg | ggattattca | gcagaggtg | tctacgagca | cggataatgg | atggacgtgg | 480 |
| acacatcgca | ccatcaccgc | ggatattacg | aaagataaac | cgtggaccgc | gcgttttgcg | 540 |
| gcgtccggcc | aaggcattca | gatccagcat | gggccgcatg | ccggccgtct | ggtgcaacag | 600 |
| tataccattc | gtacggccgg | tggagcggtg | caggctgtat | cggtttattc | cgatgatcat | 660 |
| gggaaaacgt | ggcaggctgg | caccccgatt | gggacgggta | tggatgaaaa | caaagttgta | 720 |
| gagctgtctg | acggctctct | gatgctgaac | agtcgtgcgt | cggacgggag | cggcttcgt | 780 |
| aaggttgcgc | atagcactga | tggtgggcag | acctggtccg | aaccggtttc | ggacaaaaat | 840 |
| ttgccggatt | cggttgataa | tgcccagata | attcgtgcgt | ttcctaatgc | tgcccccgat | 900 |
| gacccgcgcg | cgaaagtact | tcttctgagt | cattccccaa | atccacgtcc | gtggtcccgg | 960 |
| gatcgtggta | cgataagcat | gtcatgtgat | gacggggcct | catggaccac | ttccaaagtt | 1020 |
| tttcacgaac | cgtttgtggg | ctacacgact | attgcagttc | agagtgatgg | aagcatcggt | 1080 |
| ctgctgtcgg | aggacgcgca | caatggcgct | gattatggtg | gcatctggta | tcgtaatttt | 1140 |
| acgatgaact | ggctgggaga | acaatgtgga | caaaaacccg | cggaaccgag | cccagccct | 1200 |
| agccctactg | cagcaccgtc | cgctgcaaag | cgcaaaaaaa | aaggcggcaa | aaacggtaaa | 1260 |
| aatcgtcgta | accgtaagaa | aaaaaatcct | tga | | | 1293 |

<210> SEQ ID NO 23
<211> LENGTH: 430
<212> TYPE: PRT
<213> ORGANISM: Artificial Sequence
<220> FEATURE:
<223> OTHER INFORMATION: Synthetically generated amino acid

<400> SEQUENCE: 23

Met Gly Asp His Pro Gln Ala Thr Pro Ala Pro Ala Pro Asp Ala Ser
1               5                   10                  15

Thr Glu Leu Pro Ala Ser Met Ser Gln Ala Gln His Leu Ala Ala Asn
            20                  25                  30

Thr Ala Thr Asp Asn Tyr Arg Ile Pro Ala Ile Thr Thr Ala Pro Asn

```
            35                  40                  45
Gly Asp Leu Leu Ile Ser Tyr Asp Glu Arg Pro Lys Asp Asn Gly Asn
 50                  55                  60
Gly Gly Ser Asp Ala Pro Asn Pro Asn His Ile Val Gln Arg Arg Ser
 65                  70                  75                  80
Thr Asp Gly Gly Lys Thr Trp Ser Ala Pro Thr Tyr Ile His Gln Gly
                 85                  90                  95
Thr Glu Thr Gly Lys Lys Val Gly Tyr Ser Asp Pro Ser Tyr Val Val
            100                 105                 110
Asp His Gln Thr Gly Thr Ile Phe Asn Phe His Val Lys Ser Tyr Asp
            115                 120                 125
Gln Gly Trp Gly Gly Ser Arg Gly Gly Thr Asp Pro Glu Asn Arg Gly
            130                 135                 140
Ile Ile Gln Ala Glu Val Ser Thr Ser Thr Asp Asn Gly Trp Thr Trp
145                 150                 155                 160
Thr His Arg Thr Ile Thr Ala Asp Ile Thr Lys Asp Lys Pro Trp Thr
                165                 170                 175
Ala Arg Phe Ala Ala Ser Gly Gln Gly Ile Gln Ile Gln His Gly Pro
            180                 185                 190
His Ala Gly Arg Leu Val Gln Gln Tyr Thr Ile Arg Thr Ala Gly Gly
            195                 200                 205
Ala Val Gln Ala Val Ser Val Tyr Ser Asp Asp His Gly Lys Thr Trp
            210                 215                 220
Gln Ala Gly Thr Pro Ile Gly Thr Gly Met Asp Glu Asn Lys Val Val
225                 230                 235                 240
Glu Leu Ser Asp Gly Ser Leu Met Leu Asn Ser Arg Ala Ser Asp Gly
                245                 250                 255
Ser Gly Phe Arg Lys Val Ala His Ser Thr Asp Gly Gly Gln Thr Trp
            260                 265                 270
Ser Glu Pro Val Ser Asp Lys Asn Leu Pro Asp Ser Val Asp Asn Ala
            275                 280                 285
Gln Ile Ile Arg Ala Phe Pro Asn Ala Ala Pro Asp Asp Pro Arg Ala
            290                 295                 300
Lys Val Leu Leu Leu Ser His Ser Pro Asn Pro Arg Pro Trp Ser Arg
305                 310                 315                 320
Asp Arg Gly Thr Ile Ser Met Ser Cys Asp Asp Gly Ala Ser Trp Thr
                325                 330                 335
Thr Ser Lys Val Phe His Glu Pro Phe Val Gly Tyr Thr Thr Ile Ala
            340                 345                 350
Val Gln Ser Asp Gly Ser Ile Gly Leu Leu Ser Glu Asp Ala His Asn
            355                 360                 365
Gly Ala Asp Tyr Gly Gly Ile Trp Tyr Arg Asn Phe Thr Met Asn Trp
            370                 375                 380
Leu Gly Glu Gln Cys Gly Gln Lys Pro Ala Glu Pro Ser Pro Ala Pro
385                 390                 395                 400
Ser Pro Thr Ala Ala Pro Ser Ala Ala Lys Arg Lys Lys Gly Gly
                405                 410                 415
Lys Asn Gly Lys Asn Arg Arg Asn Arg Lys Lys Asn Pro
            420                 425                 430

<210> SEQ ID NO 24
<211> LENGTH: 1203
<212> TYPE: DNA
<213> ORGANISM: Artificial Sequence
```

<220> FEATURE:
<223> OTHER INFORMATION: Synthetically generated nucleic acid

<400> SEQUENCE: 24

```
atgggagagc tgccagcaag catgtctcag gctcagcatc ttgcagcaaa tacggctact      60
gataattatc gcattccagc gattacaacc gctccgaatg gtgatttact gattagctat     120
gatgaacggc cgaaggacaa tggaaatggt ggttccgatg cccctaaccc gaatcatatt     180
gttcagcgtc gctccacaga tggcggtaaa acttggagcg cgccaaccta tattcatcag     240
ggtacggaga ctggcaagaa agtgggatat tccgacccct cttatgtggt ggatcatcaa     300
accggtacaa tcttcaattt tcatgtgaaa tcatacgatc agggctgggg aggtagccgt     360
ggggaacag acccggaaaa ccgcgggatt attcaggcag aggtgtctac gagcacggat     420
aatggatgga cgtggacaca tcgcaccatc accgcggata ttacgaaaga taaaccgtgg     480
accgcgcgtt ttgcggcgtc cggccaaggc attcagatcc agcatgggcc gcatgccggc     540
cgtctggtgc aacagtatac cattcgtacg gccggtggag cggtgcaggc tgtatcggtt     600
tattccgatg atcatgggaa aacgtggcag gctggcaccc cgattgggac gggtatggat     660
gaaaacaaag ttgtagagct gtctgacggc tctctgatgc tgaacagtcg tgcgtcggac     720
gggagcggct ttcgtaaggt tgcgcatagc actgatggtg ggcagacctg gtccgaaccg     780
gtttcggaca aaaatttgcc ggattcggtt gataatgccc agataattcg tgcgtttcct     840
aatgctgccc ccgatgaccc gcgcgcgaaa gtacttcttc tgagtcattc cccaaatcca     900
cgtccgtggt cccgggatcg tggtacgata agcatgtcat gtgatgacgg ggcctcatgg     960
accacttcca agtttttca cgaaccgttt gtgggctaca cgactattgc agttcagagt    1020
gatgaagca tcggtctgct gtcggaggac gcgcacaatg gcgctgatta tggtggcatc    1080
tggtatcgta attttacgat gaactggctg ggagaacaat gtggacaaaa acccgcgaag    1140
cgcaaaaaaa aaggcggcaa aaacggtaaa aatcgtcgta accgtaagaa aaaaaatcct    1200
tga                                                                   1203
```

<210> SEQ ID NO 25
<211> LENGTH: 400
<212> TYPE: PRT
<213> ORGANISM: Artificial Sequence
<220> FEATURE:
<223> OTHER INFORMATION: Synthetically generated amino acid

<400> SEQUENCE: 25

```
Met Gly Glu Leu Pro Ala Ser Met Ser Gln Ala Gln His Leu Ala Ala
1               5                   10                  15

Asn Thr Ala Thr Asp Asn Tyr Arg Ile Pro Ala Ile Thr Thr Ala Pro
            20                  25                  30

Asn Gly Asp Leu Leu Ile Ser Tyr Asp Glu Arg Pro Lys Asp Asn Gly
        35                  40                  45

Asn Gly Gly Ser Asp Ala Pro Asn Pro Asn His Ile Val Gln Arg Arg
    50                  55                  60

Ser Thr Asp Gly Gly Lys Thr Trp Ser Ala Pro Thr Tyr Ile His Gln
65                  70                  75                  80

Gly Thr Glu Thr Gly Lys Lys Val Gly Tyr Ser Asp Pro Ser Tyr Val
                85                  90                  95

Val Asp His Gln Thr Gly Thr Ile Phe Asn Phe His Val Lys Ser Tyr
            100                 105                 110

Asp Gln Gly Trp Gly Gly Ser Arg Gly Gly Thr Asp Pro Glu Asn Arg
```

|  | | 115 | | | | 120 | | | | 125 | | |
|---|---|---|---|---|---|---|---|---|---|---|---|---|

Gly Ile Ile Gln Ala Glu Val Ser Thr Ser Thr Asp Asn Gly Trp Thr
130                 135                 140

Trp Thr His Arg Thr Ile Thr Ala Asp Ile Thr Lys Asp Lys Pro Trp
145                 150                 155                 160

Thr Ala Arg Phe Ala Ala Ser Gly Gln Gly Ile Gln Ile Gln His Gly
            165                 170                 175

Pro His Ala Gly Arg Leu Val Gln Gln Tyr Thr Ile Arg Thr Ala Gly
            180                 185                 190

Gly Ala Val Gln Ala Val Ser Val Tyr Ser Asp Asp His Gly Lys Thr
        195                 200                 205

Trp Gln Ala Gly Thr Pro Ile Gly Thr Gly Met Asp Glu Asn Lys Val
    210                 215                 220

Val Glu Leu Ser Asp Gly Ser Leu Met Leu Asn Ser Arg Ala Ser Asp
225                 230                 235                 240

Gly Ser Gly Phe Arg Lys Val Ala His Ser Thr Asp Gly Gly Gln Thr
                245                 250                 255

Trp Ser Glu Pro Val Ser Asp Lys Asn Leu Pro Asp Ser Val Asp Asn
            260                 265                 270

Ala Gln Ile Ile Arg Ala Phe Pro Asn Ala Ala Pro Asp Asp Pro Arg
        275                 280                 285

Ala Lys Val Leu Leu Leu Ser His Ser Pro Asn Pro Arg Pro Trp Ser
290                 295                 300

Arg Asp Arg Gly Thr Ile Ser Met Ser Cys Asp Asp Gly Ala Ser Trp
305                 310                 315                 320

Thr Thr Ser Lys Val Phe His Glu Pro Phe Val Gly Tyr Thr Thr Ile
                325                 330                 335

Ala Val Gln Ser Asp Gly Ser Ile Gly Leu Leu Ser Glu Asp Ala His
            340                 345                 350

Asn Gly Ala Asp Tyr Gly Gly Ile Trp Tyr Arg Asn Phe Thr Met Asn
        355                 360                 365

Trp Leu Gly Glu Gln Cys Gly Gln Lys Pro Ala Lys Arg Lys Lys Lys
    370                 375                 380

Gly Gly Lys Asn Gly Lys Asn Arg Arg Asn Arg Lys Lys Lys Asn Pro
385                 390                 395                 400

<210> SEQ ID NO 26
<211> LENGTH: 1248
<212> TYPE: DNA
<213> ORGANISM: Artificial Sequence
<220> FEATURE:
<223> OTHER INFORMATION: Synthetically generated nucleic acid

<400> SEQUENCE: 26
atgggagagc tgccagcaag catgtctcag gctcagcatc ttgcagcaaa tacggctact    60
gataattatc gcattccagc gattacaacc gctccgaatg gtgatttact gattagctat   120
gatgaacggc cgaaggacaa tggaaatggt ggttccgatg cccctaaccc gaatcatatt   180
gttcagcgtc gctccacaga tggcggtaaa acttggagcg cgccaaccta tattcatcag   240
ggtacggaga ctggcaagaa gtgggatat tccgacccct cttatgtggt ggatcatcaa   300
accggtacaa tcttcaattt tcatgtgaaa tcatacgatc agggctgggg aggtagccgt   360
gggggaacag acccggaaaa ccgcgggatt attcaggcag aggtgtctac gagcacggat   420
aatggatgga cgtggacaca tcgcaccatc accgcggata ttacgaaaga taaaccgtgg   480

```
accgcgcgtt ttgcggcgtc cggccaaggc attcagatcc agcatgggcc gcatgccggc    540
cgtctggtgc aacagtatac cattcgtacg gccggtggag cggtgcaggc tgtatcggtt    600
tattccgatg atcatgggaa aacgtggcag gctggcaccc cgattgggac gggtatggat    660
gaaaacaaag ttgtagagct gtctgacggc tctctgatgc tgaacagtcg tgcgtcggac    720
gggagcggct ttcgtaaggt tgcgcatagc actgatggtg ggcagacctg gtccgaaccg    780
gtttcggaca aaaatttgcc ggattcggtt gataatgccc agataattcg tgcgtttcct    840
aatgctgccc ccgatgaccc gcgcgcgaaa gtacttcttc tgagtcattc cccaaatcca    900
cgtccgtggt cccgggatcg tggtacgata agcatgtcat gtgatgacgg ggcctcatgg    960
accacttcca agttttttca cgaaccgttt gtgggctaca cgactattgc agttcagagt   1020 gatgaagca tcggtctgct gtcggaggac gcgcacaatg cgctgattta tggtggcatc   1080
tggtatcgta attttacgat gaactggctg ggagaacaat gtggacaaaa acccgcggaa   1140
ccgagcccag cccctagccc tactgcagca ccgtccgctg caaagcgcaa aaaaaaaggc   1200
ggcaaaaacg gtaaaaatcg tcgtaaccgt aagaaaaaaa atccttga                1248
```

<210> SEQ ID NO 27
<211> LENGTH: 415
<212> TYPE: PRT
<213> ORGANISM: Artificial Sequence
<220> FEATURE:
<223> OTHER INFORMATION: Synthetically generated amino acid

<400> SEQUENCE: 27

```
Met Gly Glu Leu Pro Ala Ser Met Ser Gln Ala Gln His Leu Ala Ala
 1               5                  10                  15

Asn Thr Ala Thr Asp Asn Tyr Arg Ile Pro Ala Ile Thr Thr Ala Pro
            20                  25                  30

Asn Gly Asp Leu Leu Ile Ser Tyr Asp Glu Arg Pro Lys Asp Asn Gly
        35                  40                  45

Asn Gly Gly Ser Asp Ala Pro Asn Pro Asn His Ile Val Gln Arg Arg
    50                  55                  60

Ser Thr Asp Gly Gly Lys Thr Trp Ser Ala Pro Thr Tyr Ile His Gln
65                  70                  75                  80

Gly Thr Glu Thr Gly Lys Lys Val Gly Tyr Ser Asp Pro Ser Tyr Val
                85                  90                  95

Val Asp His Gln Thr Gly Thr Ile Phe Asn Phe His Val Lys Ser Tyr
            100                 105                 110

Asp Gln Gly Trp Gly Gly Ser Arg Gly Gly Thr Asp Pro Glu Asn Arg
        115                 120                 125

Gly Ile Ile Gln Ala Glu Val Ser Thr Ser Thr Asp Asn Gly Trp Thr
    130                 135                 140

Trp Thr His Arg Thr Ile Thr Ala Asp Ile Thr Lys Asp Lys Pro Trp
145                 150                 155                 160

Thr Ala Arg Phe Ala Ala Ser Gly Gln Gly Ile Gln Ile Gln His Gly
                165                 170                 175

Pro His Ala Gly Arg Leu Val Gln Gln Tyr Thr Ile Arg Thr Ala Gly
            180                 185                 190

Gly Ala Val Gln Ala Val Ser Val Tyr Ser Asp His Gly Lys Thr
        195                 200                 205

Trp Gln Ala Gly Thr Pro Ile Gly Thr Gly Met Asp Glu Asn Lys Val
    210                 215                 220

Val Glu Leu Ser Asp Gly Ser Leu Met Leu Asn Ser Arg Ala Ser Asp
```

```
                225                 230                 235                 240
Gly Ser Gly Phe Arg Lys Val Ala His Ser Thr Asp Gly Gly Gln Thr
                    245                 250                 255
Trp Ser Glu Pro Val Ser Asp Lys Asn Leu Pro Asp Ser Val Asp Asn
                260                 265                 270
Ala Gln Ile Ile Arg Ala Phe Pro Asn Ala Ala Pro Asp Pro Arg
            275                 280                 285
Ala Lys Val Leu Leu Leu Ser His Ser Pro Asn Pro Arg Pro Trp Ser
        290                 295                 300
Arg Asp Arg Gly Thr Ile Ser Met Ser Cys Asp Asp Gly Ala Ser Trp
305                 310                 315                 320
Thr Thr Ser Lys Val Phe His Glu Pro Phe Val Gly Tyr Thr Thr Ile
                    325                 330                 335
Ala Val Gln Ser Asp Gly Ser Ile Gly Leu Leu Ser Glu Asp Ala His
                340                 345                 350
Asn Gly Ala Asp Tyr Gly Gly Ile Trp Tyr Arg Asn Phe Thr Met Asn
            355                 360                 365
Trp Leu Gly Glu Gln Cys Gly Gln Lys Pro Ala Glu Pro Ser Pro Ala
        370                 375                 380
Pro Ser Pro Thr Ala Ala Pro Ser Ala Ala Lys Arg Lys Lys Lys Gly
385                 390                 395                 400
Gly Lys Asn Gly Lys Asn Arg Arg Asn Arg Lys Lys Lys Asn Pro
                    405                 410                 415

<210> SEQ ID NO 28
<211> LENGTH: 1221
<212> TYPE: DNA
<213> ORGANISM: Artificial Sequence
<220> FEATURE:
<223> OTHER INFORMATION: Synthetically generated nucleic acid

<400> SEQUENCE: 28
ccatggggca tcaccatcac catcatctag agggagatca tccacaagct acaccagcac      60
ctgcaccaga tgctagcact gagctgccag caagcatgtc tcaggctcag catcttgcag     120
caaatacggc tactgataat tatcgcattc agcgattac aaccgctccg aatggtgatt      180
tactgattag ctatgatgaa cggccgaagg acaatggaaa tggtggttcc gatgccccta     240
acccgaatca tattgttcag cgtcgctcca cagatggcgg taaaacttgg agcgcgccaa     300
cctatattca tcagggtacg gagactggca agaaagtggg atattccgac ccctcttatg     360
tggtggatca tcaaaccggt acaatcttca attttcatgt gaaatcatac gatcagggct     420
ggggaggtag ccgtggggga acagacccgg aaaaccgcgg gattattcag gcagaggtgt     480
ctacgagcac ggataatgga tggacgtgga cacatcgcac catcaccgcg gatattacga     540
aagataaacc gtggaccgcg cgttttgcgg cgtccggcca aggcattcag atccagcatg     600
ggccgcatgc cggccgtctg gtgcaacagt ataccattcg tacggccggt ggagcggtgc     660
aggctgtatc ggtttattcc gatgatcatg gaaaacgtg gcaggctggc accccgattg     720
ggacgggtat ggatgaaaac aaagttgtag agctgtctga cggctctctg atgctgaaca     780
gtcgtgcgtc ggacgggagc ggcttttcgta aggttgcgca tagcactgat ggtgggcaga     840
cctggtccga accggtttcg gacaaaaatt tgccggattc ggttgataat gcccagataa     900
ttcgtgcgtt tcctaatgct gccccccgatg acccgcgcgc gaaagtactt cttctgagtc     960
attccccaaa tccacgtccg tggtcccggg atcgtggtac gataagcatg tcatgtgatg    1020
```

```
acggggcctc atgaccact tccaaagttt tcacgaacc gtttgtgggc tacacgacta    1080
ttgcagttca gagtgatgga agcatcggtc tgctgtcgga ggacgcgcac aatggcgctg    1140
attatggtgg catctggtat cgtaattta cgatgaactg gctgggagaa caatgtggac    1200 aaaaaccgc ggaataagct t                                                1221
```

<210> SEQ ID NO 29
<211> LENGTH: 404
<212> TYPE: PRT
<213> ORGANISM: Artificial Sequence
<220> FEATURE:
<223> OTHER INFORMATION: Synthetically generated amino acid

<400> SEQUENCE: 29

```
Met Gly His His His His His His Leu Glu Gly Asp His Pro Gln Ala
 1               5                  10                  15

Thr Pro Ala Pro Ala Pro Asp Ala Ser Thr Glu Leu Pro Ala Ser Met
            20                  25                  30

Ser Gln Ala Gln His Leu Ala Ala Asn Thr Ala Thr Asp Asn Tyr Arg
        35                  40                  45

Ile Pro Ala Ile Thr Thr Ala Pro Asn Gly Asp Leu Leu Ile Ser Tyr
    50                  55                  60

Asp Glu Arg Pro Lys Asp Asn Gly Asn Gly Gly Ser Asp Ala Pro Asn
65                  70                  75                  80

Pro Asn His Ile Val Gln Arg Arg Ser Thr Asp Gly Gly Lys Thr Trp
                85                  90                  95

Ser Ala Pro Thr Tyr Ile His Gln Gly Thr Glu Thr Gly Lys Lys Val
            100                 105                 110

Gly Tyr Ser Asp Pro Ser Tyr Val Val Asp His Gln Thr Gly Thr Ile
        115                 120                 125

Phe Asn Phe His Val Lys Ser Tyr Asp Gln Gly Trp Gly Gly Ser Arg
    130                 135                 140

Gly Gly Thr Asp Pro Glu Asn Arg Gly Ile Ile Gln Ala Glu Val Ser
145                 150                 155                 160

Thr Ser Thr Asp Asn Gly Trp Thr Trp Thr His Arg Thr Ile Thr Ala
                165                 170                 175

Asp Ile Thr Lys Asp Lys Pro Trp Thr Ala Arg Phe Ala Ala Ser Gly
            180                 185                 190

Gln Gly Ile Gln Ile Gln His Gly Pro His Ala Gly Arg Leu Val Gln
        195                 200                 205

Gln Tyr Thr Ile Arg Thr Ala Gly Gly Ala Val Gln Ala Val Ser Val
    210                 215                 220

Tyr Ser Asp Asp His Gly Lys Thr Trp Gln Ala Gly Thr Pro Ile Gly
225                 230                 235                 240

Thr Gly Met Asp Glu Asn Lys Val Val Glu Leu Ser Asp Gly Ser Leu
                245                 250                 255

Met Leu Asn Ser Arg Ala Ser Asp Gly Ser Gly Phe Arg Lys Val Ala
            260                 265                 270

His Ser Thr Asp Gly Gly Gln Thr Trp Ser Glu Pro Val Ser Asp Lys
        275                 280                 285

Asn Leu Pro Asp Ser Val Asp Asn Ala Gln Ile Ile Arg Ala Phe Pro
    290                 295                 300

Asn Ala Ala Pro Asp Asp Pro Arg Ala Lys Val Leu Leu Leu Ser His
305                 310                 315                 320

Ser Pro Asn Pro Arg Pro Trp Ser Arg Asp Arg Gly Thr Ile Ser Met
```

```
                    325                 330                 335
Ser Cys Asp Asp Gly Ala Ser Trp Thr Thr Ser Lys Val Phe His Glu
                340                 345                 350

Pro Phe Val Gly Tyr Thr Thr Ile Ala Val Gln Ser Asp Gly Ser Ile
            355                 360                 365

Gly Leu Leu Ser Glu Asp Ala His Asn Gly Ala Asp Tyr Gly Gly Ile
        370                 375                 380

Trp Tyr Arg Asn Phe Thr Met Asn Trp Leu Gly Glu Gln Cys Gly Gln
385                 390                 395                 400

Lys Pro Ala Glu

<210> SEQ ID NO 30
<211> LENGTH: 1257
<212> TYPE: DNA
<213> ORGANISM: Artificial Sequence
<220> FEATURE:
<223> OTHER INFORMATION: Synthetically generated nucleic acid

<400> SEQUENCE: 30
ccatgaagcg caaaaaaaaa ggcggcaaaa acggtaaaaa tcgtcgtaac cgtaagaaaa      60
aaaatcctgg agatcatcca caagctacac cagcaccctgc accagatgct agcactgagc     120
tgccagcaag catgtctcag gctcagcatc ttgcagcaaa tacggctact gataattatc     180
gcattccagc gattacaacc gctccgaatg gtgatttact gattagctat gatgaacggc     240
cgaaggacaa tggaaatggt ggttccgatg ccccctaaccc gaatcatatt gttcagcgtc     300
gctccacaga tggcggtaaa acttggagcg cgccaaccta tattcatcag ggtacggaga     360
ctggcaagaa agtgggatat tccgaccccct cttatgtggt ggatcatcaa accggtacaa     420
tcttcaattt tcatgtgaaa tcatacgatc agggctgggg aggtagccgt gggggaacag     480
acccggaaaa ccgcgggatt attcaggcag aggtgtctac gagcacggat aatggatgga     540
cgtggacaca tcgcaccatc accgcggata ttacgaaaga taaaccgtgg accgcgcgtt     600
ttgcggcgtc cggccaaggc attcagatcc agcatgggcc gcatgccggc cgtctggtgc     660
aacagtatac cattcgtacg gccggtggag cggtgcaggc tgtatcggtt tattccgatg     720
atcatgggaa aacgtggcag gctggcaccc cgattgggac gggtatggat gaaaacaaag     780
ttgtagagct gtctgacggc tctctgatgc tgaacagtcg tgcgtcggac gggagcggct     840
ttcgtaaggt tgcgcatagc actgatggtg ggcagacctg gtccgaaccg gtttcggaca     900
aaaatttgcc ggattcggtt gataatgccc agataattcg tgcgtttcct aatgctgccc     960
ccgatgaccc gcgcgcgaaa gtacttcttc tgagtcattc cccaaatcca cgtccgtggt    1020
cccgggatcg tggtacgata agcatgtcat gtgatgacgg ggcctcatgg accacttcca    1080 aagttttttca cgaaccgttt gtgggctaca cgactattgc agttcagagt gatggaagca    1140
tcggtctgct gtcggaggac gcgcacaatg gcgctgatta tggtggcatc tggtatcgta    1200
attttacgat gaactggctg ggagaacaat gtggacaaaa acccgcggaa taagctt       1257

<210> SEQ ID NO 31
<211> LENGTH: 416
<212> TYPE: PRT
<213> ORGANISM: Artificial Sequence
<220> FEATURE:
<223> OTHER INFORMATION: Synthetically generated amino acid

<400> SEQUENCE: 31

Met Lys Arg Lys Lys Lys Gly Gly Lys Asn Gly Lys Asn Arg Arg Asn
```

```
            1               5              10              15
        Arg Lys Lys Lys Asn Pro Gly Asp His Pro Gln Ala Thr Pro Ala Pro
                         20              25              30

Ala Pro Asp Ala Ser Thr Glu Leu Pro Ala Ser Met Ser Gln Ala Gln
                     35              40              45

His Leu Ala Ala Asn Thr Ala Thr Asp Asn Tyr Arg Ile Pro Ala Ile
             50              55              60

Thr Thr Ala Pro Asn Gly Asp Leu Leu Ile Ser Tyr Asp Glu Arg Pro
         65              70              75              80

Lys Asp Asn Gly Asn Gly Gly Ser Asp Ala Pro Asn Pro Asn His Ile
                         85              90              95

Val Gln Arg Arg Ser Thr Asp Gly Gly Lys Thr Trp Ser Ala Pro Thr
                     100             105             110

Tyr Ile His Gln Gly Thr Glu Thr Gly Lys Lys Val Gly Tyr Ser Asp
                 115             120             125

Pro Ser Tyr Val Val Asp His Gln Thr Gly Thr Ile Phe Asn Phe His
             130             135             140

Val Lys Ser Tyr Asp Gln Gly Trp Gly Gly Ser Arg Gly Gly Thr Asp
         145             150             155             160

Pro Glu Asn Arg Gly Ile Ile Gln Ala Glu Val Ser Thr Ser Thr Asp
                         165             170             175

Asn Gly Trp Thr Trp Thr His Arg Thr Ile Thr Ala Asp Ile Thr Lys
                     180             185             190

Asp Lys Pro Trp Thr Ala Arg Phe Ala Ala Ser Gly Gln Gly Ile Gln
                 195             200             205

Ile Gln His Gly Pro His Ala Gly Arg Leu Val Gln Gln Tyr Thr Ile
             210             215             220

Arg Thr Ala Gly Gly Ala Val Gln Ala Val Ser Val Tyr Ser Asp Asp
         225             230             235             240

His Gly Lys Thr Trp Gln Ala Gly Thr Pro Ile Gly Thr Gly Met Asp
                         245             250             255

Glu Asn Lys Val Val Glu Leu Ser Asp Gly Ser Leu Met Leu Asn Ser
                     260             265             270

Arg Ala Ser Asp Gly Ser Gly Phe Arg Lys Val Ala His Ser Thr Asp
                 275             280             285

Gly Gly Gln Thr Trp Ser Glu Pro Val Ser Asp Lys Asn Leu Pro Asp
             290             295             300

Ser Val Asp Asn Ala Gln Ile Ile Arg Ala Phe Pro Asn Ala Ala Pro
         305             310             315             320

Asp Asp Pro Arg Ala Lys Val Leu Leu Leu Ser His Ser Pro Asn Pro
                         325             330             335

Arg Pro Trp Ser Arg Asp Arg Gly Thr Ile Ser Met Ser Cys Asp Asp
                     340             345             350

Gly Ala Ser Trp Thr Thr Ser Lys Val Phe His Glu Pro Phe Val Gly
                 355             360             365

Tyr Thr Thr Ile Ala Val Gln Ser Asp Gly Ser Ile Gly Leu Leu Ser
             370             375             380

Glu Asp Ala His Asn Gly Ala Asp Tyr Gly Gly Ile Trp Tyr Arg Asn
         385             390             395             400

Phe Thr Met Asn Trp Leu Gly Glu Gln Cys Gly Gln Lys Pro Ala Glu
                         405             410             415

<210> SEQ ID NO 32
```

-continued

```
<211> LENGTH: 43
<212> TYPE: DNA
<213> ORGANISM: Artificial Sequence
<220> FEATURE:
<223> OTHER INFORMATION: Synthetically generated nucleic acid
<220> FEATURE:
<221> NAME/KEY: misc_feature
<222> LOCATION: (17)...(18)
<223> OTHER INFORMATION: n = a, c, g or t
<220> FEATURE:
<221> NAME/KEY: misc_feature
<222> LOCATION: (20)...(21)
<223> OTHER INFORMATION: n = a, c, g or t

<400> SEQUENCE: 32
ttttcgtctc ccatgvnnvn naagcgcaaa aaaaaaggcg gca                  43

<210> SEQ ID NO 33
<211> LENGTH: 10
<212> TYPE: PRT
<213> ORGANISM: Artificial Sequence
<220> FEATURE:
<223> OTHER INFORMATION: Synthetically generated amino acid
<220> FEATURE:
<221> NAME/KEY: VARIANT
<222> LOCATION: (2)...(3)
<223> OTHER INFORMATION: Xaa = any naturally occurring amino acid

<400> SEQUENCE: 33

Met Xaa Xaa Lys Arg Lys Lys Lys Gly Gly
 1               5                  10

<210> SEQ ID NO 34
<211> LENGTH: 1272
<212> TYPE: DNA
<213> ORGANISM: Artificial Sequence
<220> FEATURE:
<223> OTHER INFORMATION: Synthetically generated nucleic acid

<400> SEQUENCE: 34
ccatgaagcg caaaaaaaaa ggcggcaaaa acggtaaaaa tcgtcgtaac cgtaagaaaa      60
aaaatcctgg tggtggtggt tctggagatc atccacaagc tacaccagca cctgcaccag     120
atgctagcac tgagctgcca gcaagcatgt ctcaggctca gcatcttgca gcaaatacgg     180
ctactgataa ttatcgcatt ccagcgatta caaccgctcc gaatggtgat ttactgatta     240
gctatgatga acggccgaag gacaatggaa atggtggttc cgatgcccct aacccgaatc     300
atattgttca gcgtcgctcc acagatggcg gtaaaacttg gagcgcgcca acctatattc     360
atcagggtac ggagactggc aagaaagtgg gatattccga cccctcttat gtggtggatc     420
atcaaaccgg tacaatcttc aattttcatg tgaaatcata cgatcagggc tggggaggta     480
gccgtggggg aacagacccg gaaaaccgcg ggattattca gcagaggtg tctacgagca     540 cggataatgg atggacgtgg acacatcgca ccatcaccgc ggatattacg aaagataaac     600
cgtggaccgc gcgttttgcg gcgtccggcc aaggcattca gatccagcat gggccgcatg     660
ccggccgtct ggtgcaacag tataccattc gtacggccgg tggagcggtg caggctgtat     720
cggtttattc cgatgatcat gggaaaaacgt ggcaggctgg caccccgatt gggacgggta     780
tggatgaaaa caaagttgta gagctgtctg acggctctct gatgctgaac agtcgtgcgt     840
cggacgggag cggctttcgt aaggttgcgc atagcactga tggtgggcag acctggtccg     900
aaccggtttc ggacaaaaat ttgccggatt cggttgataa tgcccagata attcgtgcgt     960
ttcctaatgc tgcccccgat gacccgcgcg cgaaagtact tcttctgagt cattcccaa    1020
```

```
atccacgtcc gtggtcccgg gatcgtggta cgataagcat gtcatgtgat gacggggcct    1080
catggaccac ttccaaagtt tttcacgaac cgtttgtggg ctacacgact attgcagttc    1140
agagtgatgg aagcatcggt ctgctgtcgg aggacgcgca caatggcgct gattatggtg    1200
gcatctggta tcgtaatttt acgatgaact ggctgggaga acaatgtgga caaaaacccg    1260
cggaataagc tt                                                        1272
```

<210> SEQ ID NO 35
<211> LENGTH: 421
<212> TYPE: PRT
<213> ORGANISM: Artificial Sequence
<220> FEATURE:
<223> OTHER INFORMATION: Synthetically generated amino acid

<400> SEQUENCE: 35

```
Met Lys Arg Lys Lys Gly Gly Lys Asn Gly Lys Asn Arg Arg Asn
 1               5                  10                  15

Arg Lys Lys Lys Asn Pro Gly Gly Gly Ser Gly Asp His Pro Gln
            20                  25                  30

Ala Thr Pro Ala Pro Ala Pro Asp Ala Ser Thr Glu Leu Pro Ala Ser
        35                  40                  45

Met Ser Gln Ala Gln His Leu Ala Ala Asn Thr Ala Thr Asp Asn Tyr
50                  55                  60

Arg Ile Pro Ala Ile Thr Thr Ala Pro Asn Gly Asp Leu Leu Ile Ser
65                  70                  75                  80

Tyr Asp Glu Arg Pro Lys Asp Asn Gly Asn Gly Gly Ser Asp Ala Pro
                85                  90                  95

Asn Pro Asn His Ile Val Gln Arg Arg Ser Thr Asp Gly Gly Lys Thr
            100                 105                 110

Trp Ser Ala Pro Thr Tyr Ile His Gln Gly Thr Glu Thr Gly Lys Lys
        115                 120                 125

Val Gly Tyr Ser Asp Pro Ser Tyr Val Val Asp His Gln Thr Gly Thr
    130                 135                 140

Ile Phe Asn Phe His Val Lys Ser Tyr Asp Gln Gly Trp Gly Gly Ser
145                 150                 155                 160

Arg Gly Gly Thr Asp Pro Glu Asn Arg Gly Ile Ile Gln Ala Glu Val
                165                 170                 175

Ser Thr Ser Thr Asp Asn Gly Trp Thr Trp Thr His Arg Thr Ile Thr
            180                 185                 190

Ala Asp Ile Thr Lys Asp Lys Pro Trp Thr Ala Arg Phe Ala Ala Ser
        195                 200                 205

Gly Gln Gly Ile Gln Ile Gln His Gly Pro His Ala Gly Arg Leu Val
    210                 215                 220

Gln Gln Tyr Thr Ile Arg Thr Ala Gly Gly Ala Val Gln Ala Val Ser
225                 230                 235                 240

Val Tyr Ser Asp Asp His Gly Lys Thr Trp Gln Ala Gly Thr Pro Ile
                245                 250                 255

Gly Thr Gly Met Asp Glu Asn Lys Val Val Glu Leu Ser Asp Gly Ser
            260                 265                 270

Leu Met Leu Asn Ser Arg Ala Ser Asp Gly Ser Gly Phe Arg Lys Val
        275                 280                 285

Ala His Ser Thr Asp Gly Gly Gln Thr Trp Ser Glu Pro Val Ser Asp
    290                 295                 300

Lys Asn Leu Pro Asp Ser Val Asp Asn Ala Gln Ile Ile Arg Ala Phe
305                 310                 315                 320
```

```
Pro Asn Ala Ala Pro Asp Asp Pro Arg Ala Lys Val Leu Leu Leu Ser
                325                 330                 335

His Ser Pro Asn Pro Arg Pro Trp Ser Arg Asp Arg Gly Thr Ile Ser
            340                 345                 350

Met Ser Cys Asp Asp Gly Ala Ser Trp Thr Thr Ser Lys Val Phe His
        355                 360                 365

Glu Pro Phe Val Gly Tyr Thr Thr Ile Ala Val Gln Ser Asp Gly Ser
    370                 375                 380

Ile Gly Leu Leu Ser Glu Asp Ala His Asn Gly Ala Asp Tyr Gly Gly
385                 390                 395                 400

Ile Trp Tyr Arg Asn Phe Thr Met Asn Trp Leu Gly Glu Gln Cys Gly
                405                 410                 415

Gln Lys Pro Ala Glu
            420
```

<210> SEQ ID NO 36
<211> LENGTH: 1275
<212> TYPE: DNA
<213> ORGANISM: Artificial Sequence
<220> FEATURE:
<223> OTHER INFORMATION: Synthetically generated nucleic acid

<400> SEQUENCE: 36

```
ccatggttaa gcgcaaaaaa aaaggcggca aaaacggtaa aaatcgtcgt aaccgtaaga      60
aaaaaaatcc tggtggtggt ggttctggag atcatccaca agctacacca gcacctgcac     120
cagatgctag cactgagctg ccagcaagca tgtctcaggc tcagcatctt gcagcaaata     180
cggctactga taattatcgc attccagcga ttacaaccgc tccgaatggt gatttactga     240
ttagctatga tgaacggccg aaggacaatg aaatggtgg ttccgatgcc ctaaccccga     300
atcatattgt tcagcgtcgc tccacagatg gcggtaaaac ttggagcgcg ccaacctata     360
ttcatcaggg tacggagact ggcaagaaag tgggatattc cgacccctct tatgtggtgg     420
atcatcaaac cggtacaatc ttcaattttc atgtgaaatc atacgatcag ggctggggag     480
gtagccgtgg gggaacagac ccggaaaacc gcgggattat tcaggcagag gtgtctacga     540
gcacggataa tggatggacg tggacacatc gcaccatcac cgcggatatt acgaaagata     600
aaccgtggac cgcgcgtttt gcggcgtccg gccaaggcat tcagatccag catgggccgc     660
atgccggccg tctggtgcaa cagtatacca ttcgtacggc cggtggagcg gtgcaggctg     720
tatcggttta ttccgatgat catgggaaaa cgtggcaggc tggcacccg attgggacgg     780
gtatggatga aaacaaagtt gtagagctgt ctgacggctc tctgatgctg aacagtcgtg     840
cgtcggacgg gagcggcttt cgtaaggttg cgcatagcac tgatggtggg cagacctggt     900
ccgaaccggt ttcggacaaa aatttgccgg attcggttga taatgcccag ataattcgtg     960
cgtttcctaa tgctgccccc gatgacccgc gcgcgaaagt acttcttctg agtcattccc    1020
caaatccacg tccgtggtcc cgggatcgtg gtacgataag catgtcatgt gatgacgggg    1080
cctcatggac cacttccaaa gttttttcacg aaccgtttgt gggctacacg actattgcag    1140
ttcagagtga tggaagcatc ggtctgctgt cggaggacgc gcacaatggc gctgattatg    1200
gtggcatctg gtatcgtaat tttacgatga actggctggg agaacaatgt ggacaaaaac    1260
ccgcggaata agctt                                                    1275
```

<210> SEQ ID NO 37
<211> LENGTH: 422

-continued

```
<212> TYPE: PRT
<213> ORGANISM: Artificial Sequence
<220> FEATURE:
<223> OTHER INFORMATION: Synthetically generated amino acid

<400> SEQUENCE: 37
```

Met Val Lys Arg Lys Lys Gly Gly Lys Asn Gly Lys Asn Arg Arg
1               5                   10                  15

Asn Arg Lys Lys Lys Asn Pro Gly Gly Gly Ser Gly Asp His Pro
                20                  25                  30

Gln Ala Thr Pro Ala Pro Ala Pro Asp Ala Ser Thr Glu Leu Pro Ala
                35                  40                  45

Ser Met Ser Gln Ala Gln His Leu Ala Ala Asn Thr Ala Thr Asp Asn
    50                  55                  60

Tyr Arg Ile Pro Ala Ile Thr Thr Ala Pro Asn Gly Asp Leu Leu Ile
65                  70                  75                  80

Ser Tyr Asp Glu Arg Pro Lys Asp Asn Gly Asn Gly Ser Asp Ala
                85                  90                  95

Pro Asn Pro Asn His Ile Val Gln Arg Arg Ser Thr Asp Gly Gly Lys
                100                 105                 110

Thr Trp Ser Ala Pro Thr Tyr Ile His Gln Gly Thr Glu Thr Gly Lys
                115                 120                 125

Lys Val Gly Tyr Ser Asp Pro Ser Tyr Val Val Asp His Gln Thr Gly
    130                 135                 140

Thr Ile Phe Asn Phe His Val Lys Ser Tyr Asp Gln Gly Trp Gly Gly
145                 150                 155                 160

Ser Arg Gly Gly Thr Asp Pro Glu Asn Arg Gly Ile Ile Gln Ala Glu
                165                 170                 175

Val Ser Thr Ser Thr Asp Asn Gly Trp Thr Trp Thr His Arg Thr Ile
                180                 185                 190

Thr Ala Asp Ile Thr Lys Asp Lys Pro Trp Thr Ala Arg Phe Ala Ala
                195                 200                 205

Ser Gly Gln Gly Ile Gln Ile Gln His Gly Pro His Ala Gly Arg Leu
    210                 215                 220

Val Gln Gln Tyr Thr Ile Arg Thr Ala Gly Ala Val Gln Ala Val
225                 230                 235                 240

Ser Val Tyr Ser Asp Asp His Gly Lys Thr Trp Gln Ala Gly Thr Pro
                245                 250                 255

Ile Gly Thr Gly Met Asp Glu Asn Lys Val Val Glu Leu Ser Asp Gly
                260                 265                 270

Ser Leu Met Leu Asn Ser Arg Ala Ser Asp Gly Ser Gly Phe Arg Lys
    275                 280                 285

Val Ala His Ser Thr Asp Gly Gly Gln Thr Trp Ser Glu Pro Val Ser
    290                 295                 300

Asp Lys Asn Leu Pro Asp Ser Val Asp Asn Ala Gln Ile Ile Arg Ala
305                 310                 315                 320

Phe Pro Asn Ala Ala Pro Asp Asp Pro Arg Ala Lys Val Leu Leu Leu
                325                 330                 335

Ser His Ser Pro Asn Pro Arg Pro Trp Ser Arg Asp Arg Gly Thr Ile
                340                 345                 350

Ser Met Ser Cys Asp Asp Gly Ala Ser Trp Thr Thr Ser Lys Val Phe
    355                 360                 365

His Glu Pro Phe Val Gly Tyr Thr Thr Ile Ala Val Gln Ser Asp Gly
                370                 375                 380

```
Ser Ile Gly Leu Leu Ser Glu Asp Ala His Asn Gly Ala Asp Tyr Gly
385                 390                 395                 400

Gly Ile Trp Tyr Arg Asn Phe Thr Met Asn Trp Leu Gly Glu Gln Cys
                405                 410                 415

Gly Gln Lys Pro Ala Glu
            420
```

<210> SEQ ID NO 38
<211> LENGTH: 416
<212> TYPE: PRT
<213> ORGANISM: Artificial Sequence
<220> FEATURE:
<223> OTHER INFORMATION: Synthetically generated amino acid

<400> SEQUENCE: 38

```
Met Lys Arg Lys Lys Gly Gly Lys Asn Gly Lys Asn Arg Arg Asn
1               5                   10                  15

Arg Lys Lys Lys Asn Pro Gly Asp His Pro Gln Ala Thr Pro Ala Pro
                20                  25                  30

Ala Pro Asp Ala Ser Thr Glu Leu Pro Ala Ser Met Ser Gln Ala Gln
            35                  40                  45

His Leu Ala Ala Asn Thr Ala Thr Asp Asn Tyr Arg Ile Pro Ala Ile
50                  55                  60

Thr Thr Ala Pro Asn Gly Asp Leu Leu Ile Ser Tyr Asp Glu Arg Pro
65                  70                  75                  80

Lys Asp Asn Gly Asn Gly Gly Ser Asp Ala Pro Asn Pro Asn His Ile
                85                  90                  95

Val Gln Arg Arg Ser Thr Asp Gly Gly Lys Thr Trp Ser Ala Pro Thr
                100                 105                 110

Tyr Ile His Gln Gly Thr Glu Thr Gly Lys Lys Val Gly Tyr Ser Asp
            115                 120                 125

Pro Ser Tyr Val Val Asp His Gln Thr Gly Thr Ile Phe Asn Phe His
130                 135                 140

Val Lys Ser Tyr Asp Gln Gly Trp Gly Gly Ser Arg Gly Gly Thr Asp
145                 150                 155                 160

Pro Glu Asn Arg Gly Ile Ile Gln Ala Glu Val Ser Thr Ser Thr Asp
                165                 170                 175

Asn Gly Trp Thr Trp Thr His Arg Thr Ile Thr Ala Asp Ile Thr Lys
            180                 185                 190

Asp Lys Pro Trp Thr Ala Arg Phe Ala Ala Ser Gly Gln Gly Ile Gln
        195                 200                 205

Ile Gln His Gly Pro His Ala Gly Arg Leu Val Gln Gln Tyr Thr Ile
    210                 215                 220

Arg Thr Ala Gly Gly Ala Val Gln Ala Val Ser Val Tyr Ser Asp Asp
225                 230                 235                 240

His Gly Lys Thr Trp Gln Ala Gly Thr Pro Ile Gly Thr Gly Met Asp
                245                 250                 255

Glu Asn Lys Val Val Glu Leu Ser Asp Gly Ser Leu Met Leu Asn Ser
            260                 265                 270

Arg Ala Ser Asp Gly Ser Gly Phe Arg Lys Val Ala His Ser Thr Asp
        275                 280                 285

Gly Gly Gln Thr Trp Ser Glu Pro Val Ser Asp Lys Asn Leu Pro Asp
    290                 295                 300

Ser Val Asp Asn Ala Gln Ile Ile Arg Ala Phe Pro Asn Ala Ala Pro
305                 310                 315                 320
```

```
Asp Asp Pro Arg Ala Lys Val Leu Leu Ser His Ser Pro Asn Pro
            325                 330                 335

Arg Pro Trp Ser Arg Asp Arg Gly Thr Ile Ser Met Ser Cys Asp Asp
        340                 345                 350

Gly Ala Ser Trp Thr Thr Ser Lys Val Phe His Glu Pro Phe Val Gly
            355                 360                 365

Tyr Thr Thr Ile Ala Val Gln Ser Asp Gly Ser Ile Gly Leu Leu Ser
    370                 375                 380

Glu Asp Ala His Asn Gly Ala Asp Tyr Gly Gly Ile Trp Tyr Arg Asn
385                 390                 395                 400

Phe Thr Met Asn Trp Leu Gly Glu Gln Cys Gly Gln Lys Pro Ala Glu
                405                 410                 415
```

<210> SEQ ID NO 39
<211> LENGTH: 421
<212> TYPE: PRT
<213> ORGANISM: Artificial Sequence
<220> FEATURE:
<223> OTHER INFORMATION: Synthetically generated amino acid

<400> SEQUENCE: 39

```
Val Lys Arg Lys Lys Gly Gly Lys Asn Gly Lys Asn Arg Arg Asn
 1               5                  10                  15

Arg Lys Lys Lys Asn Pro Gly Gly Gly Ser Gly Asp His Pro Gln
            20                  25                  30

Ala Thr Pro Ala Pro Ala Pro Asp Ala Ser Thr Glu Leu Pro Ala Ser
            35                  40                  45

Met Ser Gln Ala Gln His Leu Ala Ala Asn Thr Ala Thr Asp Asn Tyr
    50                  55                  60

Arg Ile Pro Ala Ile Thr Thr Ala Pro Asn Gly Asp Leu Leu Ile Ser
65                  70                  75                  80

Tyr Asp Glu Arg Pro Lys Asp Asn Gly Asn Gly Gly Ser Asp Ala Pro
                85                  90                  95

Asn Pro Asn His Ile Val Gln Arg Arg Ser Thr Asp Gly Gly Lys Thr
            100                 105                 110

Trp Ser Ala Pro Thr Tyr Ile His Gln Gly Thr Glu Thr Gly Lys Lys
            115                 120                 125

Val Gly Tyr Ser Asp Pro Ser Tyr Val Val Asp His Gln Thr Gly Thr
    130                 135                 140

Ile Phe Asn Phe His Val Lys Ser Tyr Asp Gln Gly Trp Gly Gly Ser
145                 150                 155                 160

Arg Gly Gly Thr Asp Pro Glu Asn Arg Gly Ile Ile Gln Ala Glu Val
                165                 170                 175

Ser Thr Ser Thr Asp Asn Gly Trp Thr Trp Thr His Arg Thr Ile Thr
            180                 185                 190

Ala Asp Ile Thr Lys Asp Lys Pro Trp Thr Ala Arg Phe Ala Ala Ser
            195                 200                 205

Gly Gln Gly Ile Gln Ile Gln His Gly Pro His Ala Gly Arg Leu Val
    210                 215                 220

Gln Gln Tyr Thr Ile Arg Thr Ala Gly Gly Ala Val Gln Ala Val Ser
225                 230                 235                 240

Val Tyr Ser Asp Asp His Gly Lys Thr Trp Gln Ala Gly Thr Pro Ile
                245                 250                 255

Gly Thr Gly Met Asp Glu Asn Lys Val Val Glu Leu Ser Asp Gly Ser
            260                 265                 270
```

```
Leu Met Leu Asn Ser Arg Ala Ser Asp Gly Ser Gly Phe Arg Lys Val
        275                 280                 285

Ala His Ser Thr Asp Gly Gly Gln Thr Trp Ser Glu Pro Val Ser Asp
        290                 295                 300

Lys Asn Leu Pro Asp Ser Val Asp Asn Ala Gln Ile Ile Arg Ala Phe
305                 310                 315                 320

Pro Asn Ala Ala Pro Asp Asp Pro Arg Ala Lys Val Leu Leu Leu Ser
                325                 330                 335

His Ser Pro Asn Pro Arg Pro Trp Ser Arg Asp Arg Gly Thr Ile Ser
                340                 345                 350

Met Ser Cys Asp Asp Gly Ala Ser Trp Thr Thr Ser Lys Val Phe His
        355                 360                 365

Glu Pro Phe Val Gly Tyr Thr Thr Ile Ala Val Gln Ser Asp Gly Ser
        370                 375                 380

Ile Gly Leu Leu Ser Glu Asp Ala His Asn Gly Ala Asp Tyr Gly Gly
385                 390                 395                 400

Ile Trp Tyr Arg Asn Phe Thr Met Asn Trp Leu Gly Glu Gln Cys Gly
                405                 410                 415

Gln Lys Pro Ala Glu
                420
```